US007595316B2

(12) United States Patent
Ohtake et al.

(10) Patent No.: US 7,595,316 B2
(45) Date of Patent: Sep. 29, 2009

(54) HETEROARYLOXY NITROGENOUS SATURATED HETEROCYCLIC DERIVATIVE

(75) Inventors: Norikazu Ohtake, Tsukuba (JP); Akira Naya, Tsukuba (JP); Yuji Haga, Tsukuba (JP); Makoto Jitsuoka, Moriya (JP); Takuya Suga, Tsukuba (JP); Ryo Yoshimoto, Tsukuba (JP); Shigeru Tokita, Tsukuba (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 271 days.

(21) Appl. No.: 10/561,115

(22) PCT Filed: Jun. 24, 2004

(86) PCT No.: PCT/JP2004/009272

§ 371 (c)(1),
(2), (4) Date: Dec. 15, 2005

(87) PCT Pub. No.: WO2005/007644

PCT Pub. Date: Jan. 27, 2005

(65) Prior Publication Data

US 2006/0178375 A1  Aug. 10, 2006

(30) Foreign Application Priority Data

Jun. 27, 2003  (JP)  ............... 2003-184879

(51) Int. Cl.
*A01N 43/58*  (2006.01)
*A61K 31/50*  (2006.01)
*C07D 239/00*  (2006.01)
*C07D 239/02*  (2006.01)

(52) U.S. Cl. ...................... 514/247; 544/242
(58) Field of Classification Search ........................ None
See application file for complete search history.

(56) References Cited

U.S. PATENT DOCUMENTS

| 6,313,127 | B1 | 11/2001 | Waterson et al. |
| 6,525,070 | B2 | 2/2003 | Rigby et al. |
| 6,562,847 | B1 | 5/2003 | Lee |
| 6,673,829 | B2 | 1/2004 | Dorwald et al. |
| 6,888,001 | B2 | 5/2005 | Lee |
| 6,903,115 | B2 | 6/2005 | Rigby et al. |
| 7,067,507 | B2 * | 6/2006 | Pulley et al. ............ 514/183 |
| 2005/0215559 | A1 | 9/2005 | Yoon et al. |

FOREIGN PATENT DOCUMENTS

WO  WO 02/06223  1/2002
WO  WO 2005/097111  * 10/2005

OTHER PUBLICATIONS

Fox et al. Behavioural Brain Research, 2002, 131, 151-161.*

"MeSH result", http://www.ncbi.nlm.nih.gov/sites/entrez?Db=mesh&Cmd=ShowDetailView&TermToSearch=68002318&ordinalpos=3&itool=EntrezSystem2.PEntrez.Mesh.Mesh_ResultsPanel.Mesh_RVFull, accessed Jun. 27, 2007.*
"Water-Electrolyte Imbalance", http://www.nlm.nih.gov/cig/mesh/2007/MB_cgi?mode=&term=Water-Electrolyte+Imbalance&field=entry, accessed Jun. 28, 2007.*
"Pituitary Diseases", http://www.nlm.nih.gov/cgi/mesh/2007/MB_cgi?mode=&term=Pituitary+Diseases&field=entry#TreeC19.700, accessed Jun. 28, 2007.*
Cumulative Trauma Disorders, http://www.nlm.nih.gov/cgi/mesh/2007/MB_cgi?mode=&index=11628&field=all&HM=&II=& PA=&form=&input=, accessed Jun. 27, 2007.*
"Motion Sickness", http://www.nlm.nih.gov/cgi/mesh/2007/MB_cgi, accessed Jun. 27, 2007.*
"Gait Disorders, Neurologic", http://www.nlm.nih.gov/cgi/mesh/2007/MB_cgi?mode=&index=18843&field=all&HM=&II=&PA=&form=&input=, accessed Jun. 27, 2007.*
Dorwald, F.Z. Side Reactions in Organic Synthesis, 2005, p. IX of preface.*
Supplementary European Search Report, Application No. EP 04746741 (dated Feb. 16, 2009).

* cited by examiner

*Primary Examiner*—James O Wilson
*Assistant Examiner*—Noble Jarrell
(74) *Attorney, Agent, or Firm*—J. Eric Thies; William Krovatin

(57) ABSTRACT

Compound of the formula: (I) [wherein each of $X^1$, $X^2$ and $X^3$ independently represents N or CH, W represents the formula (II):(II) or the formula (III):(III) and Y represents a group of the formula (IV):(IV)], or a pharmacologically acceptable salt thereof. This compound exhibits histamine receptor H3 antagonist or inverse agonist activity and is useful of the treatment and/or prevention of obesity, diabetes, hormonal secretion abnormality, sleep, disorder, etc.

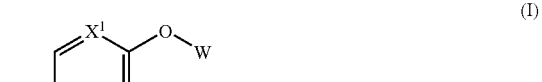

(I)

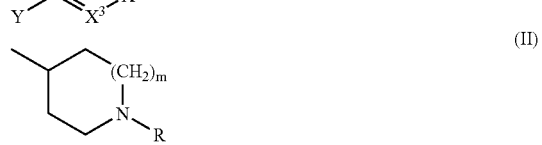

(II)

(III)

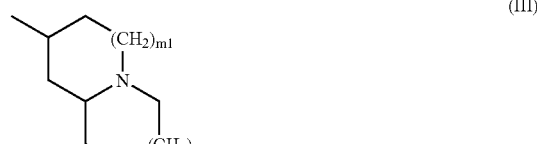

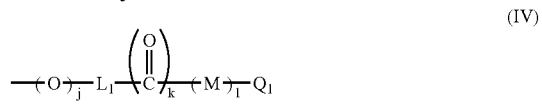

(IV)

8 Claims, No Drawings

US 7,595,316 B2

HETEROARYLOXY NITROGENOUS SATURATED HETEROCYCLIC DERIVATIVE

CROSS REFERENCE TO RELATED APPLICATIONS

This application is a U.S. National Phase application under 35 U.S.C. § 371 of PCT Application No. PCT/JP2004/009272, filed Jun. 24, 2004, which claims priority under 35 U.S.C. § 119 from Japanese Application No. JP2003-184879, filed Jun. 27, 2003.

TECHNICAL FIELD

The present invention relates to heteroaryloxy-nitrogen-containing saturated heterocyclic derivatives useful in the field of medicines. The compound act as a histamine-H3 receptor antagonist, and are useful for preventives or remedies for various circulatory system disorders, nervous system disorders, metabolic system disorders, etc.

BACKGROUND ART

It has been known that, in organisms such as typically mammals, histamine that is a physiologically-active endogenous factor functions as a neurotransmitter and has extensive pharmacological activities (for example, see *Life Science*, Vol. 17, 1975, p. 503). Immunohistochemical studies have made it clear that a histamine-agonistic (producing) cell body exists in the nodal papillary nucleus in a posterior hypothalamic region and that histamine nerve fibers project in an extremely broad range in the brain, which supports various pharmacological effects of histamine (for example, see *Journal of Comprehensive Neurology*, Vol. 273, p. 283).

The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see *Progress in Neurobiology*, Vol. 63, p. 637 (2001)).

The existence of projection to the brain region that relates to vigilance sustenance, for example, to cerebral cortex suggests the role in control of vigilance or vigilance-sleep cycle. The existence of projection to many peripheral structures such as hippocampus and amygdaloid complex suggests the role in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, histamine-H3 receptor, has been shown by various pharmacological and physiological studies (for example, see *Trends in Pharmacological Science*, Vol. 8, p. 24 (1986)); and recently, human and rodent histamine-H3 receptor genes have been identified and their existence has been made clear (for example, see *Molecular Pharmacology*, Vol. 55, p. 1101 (1999)).

It is suggested that histamine-H3 receptor exists in the presynaptic membrane of central or peripheral neurocytes and functions as a self-receptor, therefore controlling the release of histamine and controlling the release of other neurotransmitters. Specifically, it is reported that a histamine-H3 receptor agonist, or its antagonist or inverse-agonist controls the release of histamine, noradrenaline, serotonin, acetylcholine or dopamine from nerve ending. For example, the release of these neurotransmitters is inhibited by an agonist such as (R)-(α)-methylhistamine inhibits, and is promoted by an antagonist or inverse-agonist such as thioperamide (for example, see *Trends in Pharmacological Science*, Vol. 19, p. 177 (1998)).

Recent studies have shown that histamine-H3 receptor has extremely high homeostatic activities (endogenous agonistic factor, e.g., activity observed in the absence of histamine) in the receptor-expressing cells/tissues or in a membrane fraction derived from the expressing cells/tissues and even in living bodies (for example, see *Nature*, Vol. 408, p. 860). It is reported that these homeostatic activities are inhibited by an inverse-agonist. For example, a homeostatic self-receptor activity is inhibited by thioperamide or syproxyfan, and, as a result, the release of neurotransmitters from nerve ending, for example, the release and liberation of histamine from it is thereby promoted.

In animal experiments with rats, a high-level selective inhibitor of histamine synthase (histidine decarboxylase) inhibits the vigilance of rats, which suggests that histamine may function for controlling motive vigilance, Administration of a histamine-H3 receptor agonist, (R)-(α)-methylhistamine to cats increases their deep slow-wave sleep (for example, see *Brain Research*, Vol. 523, p. 325 (1990)). Contrary to this, a histamine-H3 receptor antagonist or inverse-agonist, thioperamide dose-dependently increase vigilance. In addition, thioperamide decreases slow-wave and REM sleep (for example, see *Life Science*, Vol. 48, p. 2397 (1991)).

A histamine-H3 receptor antagonist or inverse-agonist, thioperamide or GT-2331 decreases the emotional cataplexy and sleep of narcoleptic dogs (for example, see *Sleep*, Vol. 24, Summaries, A, p. 23 (2001)). These pieces of information suggest that the H3 receptor may participate in vigilance-sleep control and in diseases accompanied by sleep deficiency, further suggesting a possibility that a selective H3-agonist or its antagonist or inverse-agonist may be useful for remedy of sleep disorders and other various diseases accompanied by sleep disorders (for example, idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, shinzophrenia).

In animal experiments with rats, administration of a histamine-H3 receptor antagonist or inverse-agonist, thioperamide or GT-2331 to rats improved learning disorder (LD) and attention deficit hyperactivity disorder (ADHD) (for example, see *Behavioral Brain Research*, Vol. 131, p. 151 (2002)). These pieces of information suggest a possibility that that a selective H3-agonist or its antagonist or inverse-agonist may be useful for remedy and/or prevention of learning disorder or attention deficit hyperactivity disorder.

In animal experiments with rats, administration of histamine to the ventricle of rats inhibited their eating action, therefore suggesting that histamine may participate in control of eating action (for example, see *Brain Research*, Vol. 793, p. 279 (1998)).

A histamine-H3 receptor antagonist or inverse-agonist, thioperamide dose-dependently inhibits eating action. In addition, thioperamide promotes intracerebral histamine release (for example, see *Life Science*, Vol. 69, p. 469 (2001)). These pieces of information suggest that the H3 receptor may participate in eating action control, further suggesting a possibility that an H3 antagonist or inverse-agonist may be useful for prevention or remedy of metabolic diseases such as eating disorder, obesity, diabetes, emaciation, hyperlipemia.

In animal experiments with rats, administration of a histamine-H3 receptor agonist, (R)-(α)-methylhistamine to rats dose-dependently lowered their basal diastolic pressure. Its action was antagonized by a histamine-H3 receptor antagonist or inverse-agonist, thioperamide (for example, see *Journal of Physiology and Pharmacology*, Vol. 49, p. 191 (1998)). These pieces of information suggest that a histamine-H3 receptor may participate in control of blood pressure, heart beat and cardiac output, further suggesting a possibility that a histamine-H3 receptor agonist or its antagonist or inverse-agonist may be useful for prevention or remedy of circulatory system diseases such as hypertension and various cardiac disorders.

In animal experiments with rats, administration of a histamine-H3 receptor agonist, (R)-(α)-methylhistamine to rats lowered their object recognition and learning effects in the object recognition test and the passive turnout test with them. On the other hand, in the scopolamine-induced amnesia test with them, a histamine-H3 receptor antagonist or inverse-agonist, thioperamide dose-dependently relieved their amnesia induced by the chemical (for example, see *Behavioural Brain Research*, Vol. 104, p. 147 (1999). These pieces of information suggest a possibility that a histamine-H3 receptor antagonist or inverse-agonist may be useful for prevention or remedy of various diseases accompanied by memory and learning disorder, for example, Alzheimer's disease, Parkinson's disease or attention deficit/hyperactivity disorder.

It is shown that, in animal experiments with rats, a histamine-H3 receptor antagonist or inverse-agonist, thioperamide dose-dependently inhibited the spasm induced by electric shock or the epileptoid seizure induced by pentylene tetrazole (PTZ) (for example, see *European Journal of Pharmacology*, Vol. 234, p. 129 (1993) and *Pharmacology Biochemistry and Behavior*, Vol. 68, p. 735 (2001)). These pieces of information suggests a possibility that a histamine-H3 receptor antagonist or inverse-agonist may be useful for prevention or remedy of epilepsy or central spasm.

In addition to the above-mentioned thioperamide or cycloxyfan, for example, a compound of the following formula (A):

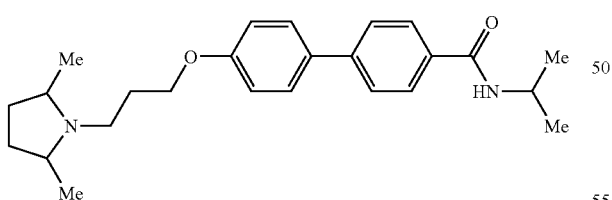

is described as a histamine-H3 receptor-antagonistic or inverse-agonistic compound (WO02/40461).

The compound of formula (A) has a propylene group between the pyrrolidinyl group and the oxygen atom therein, and it differs from compounds (I) of the present invention in that the oxygen atom directly bonds to the pyrrolidinyl group in the latter. Further, they differ in that, in the compound of formula (A), a phenyl group bonds to the oxygen atom, but in the compounds of the present invention, a group of the following formula (I-1)

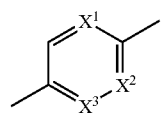

wherein the symbols have the same meanings as above, bonds to the oxygen atom, and at least one of $X^1$, $X^2$ and $X^3$ in the ring is a nitrogen atom.

A compound of the following formula (B):

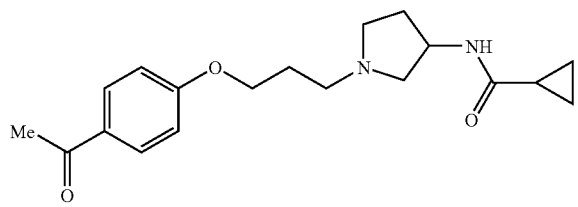

is described as a histamine-H3 receptor antagonistic compound (for example, WO02/06223).

The compound of formula (B) has a 4-acetyl-phenoxy group and a pyrrolidinyl group that are a part of the constitutive elements of the compounds of the present invention, but its structure differs from that of the compounds of the present invention in that a propylene group exists between the 4-acetyl-phenoxy group and the pyrrolidinyl group in the former. In addition, the position of the nitrogen atom in the pyrrolidinyl group in formula (B) differs from that in the compounds of the present invention.

A compound of the following formula (C):

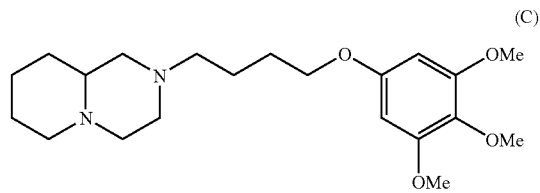

is described as a histamine-H3 receptor antagonistic compound (for example, JP-A 2003-064081).

The compound of formula (C) has an octahdyropyrido[1,2-a]pyrazinyl group, but this differs from the compounds of the present invention in that the moiety Y in a formula (I) representing the latter is a monocyclic or bicyclic group having one nitrogen atom in the ring, such as a pyrrolidinyl group or an octahydroquinolidinyl group. In addition, they essentially differ in the point of their structures in that, in formula (C), the octahdyropyrido[1,2-a]pyrazinyl group bonds to the oxygen atom via a propylene group therebetween, but in the compounds of the present invention, the corresponding groups bond directly to each other with no alkylene group therebetween.

A compound having an N-isopropyl-piperidin-4-yl group of the following formula (D):

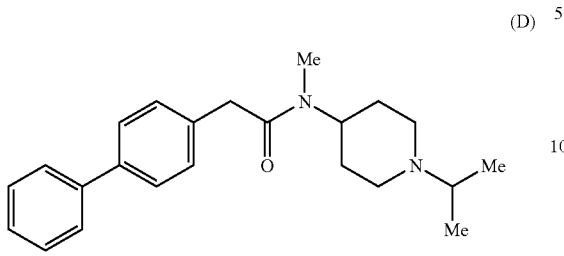

is described as a compound that strongly and selectively bind to a histamine-H3 receptor (for example, see WO03/024929). The compound of formula (D) corresponds to the compounds of the present invention in that it has an N-isopropylpiperidin-4-yl group, but they differ in the following points: The compounds of formula (I) of the present invention do not have a biphenyl group; and in the compound of formula (D), the biphenyl group bonds to the N-isopropylpiperidin-4-yl group via a carbamoylmethyl group therebetween, but in the compounds of formula (I) of the present invention, the substituted piperidinyl group bonds to a group of formula (I-1):

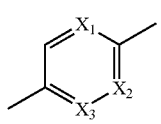

wherein the symbols have the same meanings as above, via an oxygen atom therebetween.

A compound having an N-benzylhomopiperidin-3-yloxy group of the following formula (E):

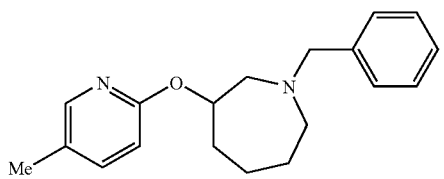

is described (for example, WO01/19817).

The compound of formula (E) differs from the compounds of the present invention in the point of the position of N of homopiperidine. Further, the compound of formula (E) has the property of a nicotinic acetylcholine receptor ligand, but the compounds of the present invention have the property of a histamine-H3 receptor antagonist or inverse-agonist. In addition, WO01/19817 does neither have a description to say that the compound of formula (E) may act as a histamine-H3 receptor antagonist or inverse-agonist, nor have a description to suggest it.

A compound having an N-ethylpyrrolidin-3-yloxypyrazinyl group of the following formula (F):

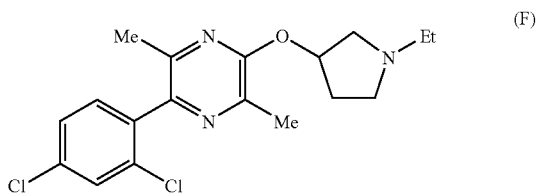

is described (for example, WO01/60806). The structure of the compound of formula (F) differs from that of the compounds of the present invention in that the former has a methyl group at the 3- and 6-positions of the pyrazine ring in formula (F). Regarding its use, the compound of formula (F) is a CRF receptor ligand, and WO01/60806 does neither have a description to say that the compound may act as a histamine-H3 receptor antagonist or inverse-agonist, nor have a description to suggest it.

The present invention is to provide a heteroaryloxy-nitrogen-containing saturated heterocyclic derivative that has an action of antagonizing histamine to bond to a histamine-H3 receptor, or has an activity of inhibiting the homeostatic activity of a histamine-H3 receptor, and to provide a preventive or a remedy comprising it for metabolic system diseases such as obesity, diabetes, hormone secretion disorder, hyperlipemia, gout, fatty liver; circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder; and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

DISCLOSURE OF THE INVENTION

We, the present inventors have assiduously studied for the purpose of developing a compound that prevents histamine from binding to a histamine-H3 receptor and, as a result, have found that the compounds of the invention, heteroaryloxy-cycloalkylamine derivatives characterized by having an action as a histamine-H3 receptor antagonist and/or inverse-agonist are novel substances not described in publications, and have found that specific compounds including the compounds are effective as a histamine-H3 receptor antagonist or inverse-agonist. On the basis of these findings, we have completed the present invention.

Specifically, the invention relates to the following:

(1) A compound of the following formula (I) or its pharmaceutically-acceptable salt:

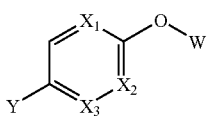
(I)

[wherein $X^1$, $X^2$ and $X^3$ each independently represent N or CH (provided that all of $X^1$, $X^2$ and $X^3$ are not CH at the same time); W represents a group of the following formula (II):

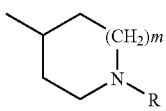
(II)

(wherein m indicates an integer of from 0 to 3; R represents a linear or branched lower alkyl group (excepting a methyl group), a cycloalkyl group having from 3 to 9 carbon atoms, an aralkyl group or a heterocyclic group having from 3 to 8 carbon atoms (the hetero ring has 1 or 2 nitrogen atoms or oxygen atoms), which may be substituted with a group selected from a class consisting of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbonyl group and a trifluoromethyl group), or represents a group of a formula (III):

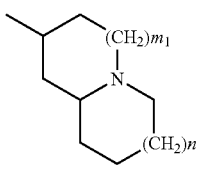
(III)

(wherein m1 indicates an integer of from 0 to 3; n indicates an integer of from 0 to 2); Y represents a group of a formula (IV):

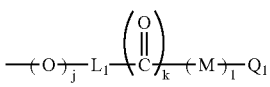
(IV)

(wherein j, k and l each independently indicate 0 or 1; $L_1$ represents a lower alkylene group having from 1 to 4 carbon atoms, or a single bond; M represents an oxygen atom or a group of a formula (V):

(V)

(wherein $R^0$ represents a lower alkyl group having from 1 to 4 carbon atoms); $Q_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have from 1 to 3 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a group of a formula (V-1):

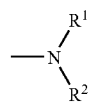
(V-1)

(wherein $R^1$ and $R^2$ are the same or different, each representing a lower alkyl group or a mono- or di-lower alkylcarbamoyl group, or $R^1$ and $R^2$ together form, along with the adjacent nitrogen atom, a 3- to 9-membered lactam ring, a heterocyclic group having from 3 to 8 carbon atoms (the group has 1 or 2 nitrogen atoms or oxygen atoms as the constitutive atoms thereof), a 5-membered heteroaryl group, or a condensed-cyclic heteroaryl group)].

(2) The compound or its pharmaceutically-acceptable salt of above (1), wherein R in formula (II) is a cycloalkyl group having from 3 to 9 carbon atoms or a heterocyclic group having from 3 to 8 carbon atoms (the hetero ring has 1 or 2 nitrogen atoms or oxygen atoms), which may be substituted with a group selected from a class consisting of a cyano group, a hydroxy group, a lower alkyl group (the lower alkyl group may be substituted with a hydroxy group, a halogen atom or an amino group), a lower alkoxy group, a mono-lower alkylaminocarbonyloxy group and a di-lower alkylaminocarbonyloxy group, or a represents a group of a formula (III):

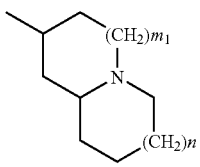

(III)

(wherein the symbols have the same meanings as above).

(3) The compound or its pharmaceutically-acceptable salt of above (1) or (2), wherein the group of formula (IV-1):

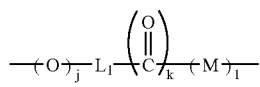

(IV-1)

(wherein the symbols have the same meanings as above) in the formula (IV):

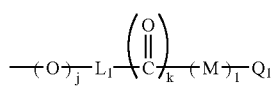

(IV)

(wherein the symbols have the same meanings as above) is a $C_{1-4}$ lower alkylene group, a carbonyl group, —C(O)—O—, a —$C_{1-4}$ lower alkylene-C(O)—, a —$C_{1-4}$ lower alkylene-C(O)—O—, a —$C_{1-4}$ lower alkylene-C(O)—N(R°)—, —C(O)—N(R°)—, —O—$C_{1-4}$ lower alkylene-, or a single bond.

(4) The compound of above (3), wherein $Q_1$ is a linear or branched lower alkyl group, a cycloalkyl group having from 3 to 9 carbon atoms, a phenyl group or a naphthyl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a 5- or 6-membered heteroaryl group having from 1 to 3 hetero atoms selected from a group consisting of an oxygen atom, a sulfur atom and a nitrogen atom, a heterocyclic group having from 3 to 8 carbon atoms and having from 1 to 3 nitrogen atoms or oxygen atoms in the ring, or a mono- to tri-cyclic condensed-cyclic heteroaryl group optionally having from 1 to 3 hetero atoms selected from a group consisting of an oxygen atom, a sulfur atom and a nitrogen atom in each ring.

(5) The compound or its pharmaceutically-acceptable salt of above (3), wherein $Q_1$ of the formula (V-1) is a group of a formula (V-10):

(V-10)

(wherein $R^{10}$ and $R^{20}$ together form, along with the adjacent nitrogen atom, a 3- to 9-membered lactam ring, a heterocyclic ring having from 3 to 8 carbon atoms ($R^{10}$ and $R^{20}$ may have, apart from the adjacent nitrogen atom, 1 or 2 nitrogen atoms or oxygen atoms in the ring as the constitutive atoms of the hetero ring), a 5-membered heteroaryl group having from 1 to 4 nitrogen atoms in the ring, or a bicyclic condensed-cyclic heteroaryl group having from 1 to 3 nitrogen atoms or oxygen atoms in each ring).

(6) The compound or its pharmaceutically-acceptable salt of above (1), wherein —Y in formula (I) is a phenyl group, a pyridyl group, a pyridazinyl group or a pyrimidinyl group, which may be substituted with a group selected from a class consisting of a hydroxyl group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group).

(7) The compound or its pharmaceutically-acceptable salt of above (1), wherein —Y in formula (I) is a bi- or tri-cyclic condensed ring having at least one phenyl group or pyridyl group in the ring, which may have therein 1 or 2 substituents selected from a class consisting of a hydroxyl group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group).

(8) The compound or its pharmaceutically-acceptable salt of above (1), wherein —Y in formula (I) is a furyl group, a thienyl group, a pyrrolyl group, an imidazolyl group, a pyrazolyl group, a thiazolyl group, a thiadiazolyl group, an isothiazolyl group, an oxazolyl group, an isoxazolyl group, a pyridyl group, a pyridazinyl group, a pyrimidinyl group or a pyrazinyl group, which may have in the ring thereof, 1 or 2 substituents selected from a class consisting of a hydroxyl group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group).

(9) The compound or its pharmaceutically-acceptable salt of above (1), wherein —Y in formula (I) is an oxetanyl group, a tetrahydrofuranyl group, a tetrahydropyranyl group, a pyrrolidinyl group, a piperidinyl group, a homopiperidinyl group, a morpholinyl group or a homomorpholinyl group, which may have in the ring thereof, 1 or 2 substituents selected from a class consisting of a hydroxyl group, a lower alkyl group (the lower alkyl group may be substituted with a hydroxy group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group).

(10) The compound or its pharmaceutically-acceptable salt of above (1), wherein —Y in the formula (I) is a group of a formula (IV-2):]

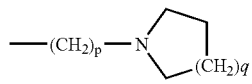

(IV-2)

(wherein p indicates an integer of from 1 to 3; q indicates an integer of from 1 to 4).

(11) The compound or its pharmaceutically-acceptable salt of above (1) to (10), wherein at least one of $X^1$ and $X^2$ in the group of formula (I-1) of the formula (I):

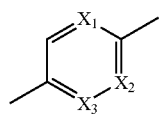

(I-1)

(wherein the symbols have the same meanings as above) is a nitrogen atom, or both $X^2$ and $X^3$ therein are nitrogen atoms.

(12) The compound or its pharmaceutically-acceptable salt of formula (I), which includes 2-(1-cyclopentylpiperidin-4-yloxy)-5-(4-cyanophenyl)pyrimidine, 2-(1-isopropylpiperidin-4-yloxy)-5-(4-cyanophenyl)pyrimidine, 2-(1-(cyclopentylpyrrolidin-3-yloxy)-5-(4-carbamoylphenyl)pyrimidine, 2-(1-cyclopentylpyrrolidin-3-yloxy)-5-(4-cyanophenyl)pyrimidine, 2-(1-cyclopentylpiperidin-4-yloxy)-5-{(3-methyl-1,2,4-oxadiazol-5-yl)phenyl}pyrimidine, 2-(1-cyclopentylpiperidin-4-yloxy)-5-(4-cyanophenyl)pyrimidine, 2-(1-(cyclobutylpiperidin-4-yloxy)-5-(4-cyanophenyl)pyrimidine, 2-(1-cyclohexylpiperidin-4-yloxy)-5-(4-cyanophenyl)pyrimidine, 2-(1-cyclopropylpiperidin-4-yloxy)-5-(4-cyanophenyl)pyrimidine, 2-(1-ethylpiperidin-4-yloxy)-5-(4-cyanophenyl)pyrimidine, 2-(1-cyclopentylpiperidin-4-yloxy)-5-{4-(pyrrolidin-1-ylcarbonyl)phenyl}piperidine, 2-(1-cyclopentylpiperidin-4-yloxy)-5-{4-(dimethylcarbamoyl)phenyl}pyrimidine, 2-(1-cyclopentylpiperidin-4-yloxy)-5-{4-(morpholin-4-ylcarbonyl)phenyl}pyrimidine, 2-(1-cyclopentylpiperidin-4-yloxy)-5-{4-(phenoxy)phenyl}pyrimidine, 2-(1-cyclopentylpiperidin-4-yloxy)-5-(3-quinolinyl)piperidine, 2-(1-cyclopentylpiperidin-4-yloxy)-5-{5-indolyl}pyrimidine, 2-(1-cyclopentylpiperidin-4-yloxy)-5-(1H-pyridin-2-on-1-yl)pyrimidine, 2-(1-cyclopentylpiperidin-4-yloxy)-5-(piperidin-2-on-1-yl)pyrimidine, 2-(1-cyclopentylpiperidin-4-yloxy)-5-(8-quinolinyl)pyrimidine, 2-(1-cyclopentylpiperidin-4-yloxy)-5-(4-phenyl-4-hydroxypiperidin-1-yl)pyrimidine, 2-(1-cyclopentylpiperidin-4-yloxy)-5-(2-methoxypyridin-5-yl)pyrimidine, 2-(1-cyclopentylpiperidin-4-yloxy)-5-(4-chlorophenyl)pyrimidine, 2-(1-cyclopentylpiperidin-4-yloxy)-5-(4-trifluoromethylphenyl)pyrimidine, 2-(1-cyclopentylpiperidin-4-yloxy)-5-(pyridin-3-yl)pyrimidine, 2-(1-cyclopentylpiperidin-4-yloxy)-5-(4-methoxyphenyl)pyrimidine, 2-(1-cyclopentylpiperidin-4-yloxy)-5-(dibenzofuran-4-yl)pyrimidine, 2-(1-cyclopentylpiperidin-4-yloxy)-5-(2-cyclopentyloxypyridin-5-yl)pyrimidine, 2-(1-cyclopentylpiperidin-4-yloxy)-5-(1H-pyridin-2-on-5-yl)pyrimidine, 2-(1-cyclopentylpiperidin-4-yloxy)-5-(1-cyclopentyl-1H-pyridin-2-on-3-yl)pyrimidine, 2-(1-cyclopentylpiperidin-4-yloxy)-5-{2-(pyrrolidin-1-ylcarbonyl)pyridin-5-yl}pyrimidine, 2-(1-cyclopentylpiperidin-4-yloxy)-5-(2-cyano-5-thenyl)pyrimidine, 2-(1-cyclopentylpiperidin-4-yloxy)-5-{4-(morpholin-3-on-4-yl)phenyl}pyrimidin, 2-(1-cyclopentylpiperidin-4-yloxy)-5-{4-(2-oxazolidin-3-yl)phenyl}pyrimidine, 2-(1-cyclopentylpiperidin-4-yloxy)-5-(2-methylpyridin-5-yl)pyrimidin,
2-(1-cyclopentylpiperidin-4-yloxy)-5-(2-fluoropyridin-5-yl)pyrimidine,
2-(1-cyclopentylpiperidin-4-yloxy)-5-{4-(1H-pyridin-2-on-1-yl)phenyl}pyrimidine,
2-(1-cyclopentylpiperidin-4-yloxy)-5-{4-(methylsulfonyl)phenyl}pyrimidine,
2-(1-cyclopentylpiperidin-4-yloxy)-5-{4-acetylphenyl}pyrimidine,
2-(1-cyclopentylpiperidin-4-yloxy)-5-(4-trifluoromethoxyphenyl)pyrimidine,
2-(1-cyclopentylpiperidin-4-yloxy)-5-{4-(2-hydroxy-2-propyl)phenyl}pyrimidine,
2-(1-cyclopentylpiperidin-4-yloxy)-5-(2-ethylpyridin-5-yl)pyrimidine,
2-(1-cyclopentylpiperidin-4-yloxy)-5-(4-cyanophenyl)pyrazine,
5-(1-cyclopentylpiperidin-4-yloxy)-2-(4-cyanophenyl)pyridine,
2-(1-cyclopentylpiperidin-4-yloxy)-5-(4-cyanophenyl)pyridazine,
2-(1-cyclopentylpiperidin-4-yloxy)-5-(piperidin-1-ylcarbonyl)pyrimidine,
2-(1-cyclopentylpiperidin-4-yloxy)-5-(piperidin-1-ylmethyl)phenyl}pyrimidine,
2-(1-cyclopentylpiperidin-4-yloxy)-5-(4-phenylpiperazin-1-ylmethyl)pyrimidine,
2-(1-cyclopentylpiperidin-4-yloxy)-5-(2-cyanopyrimidin-5-yl)pyrimidine,
2-(1-cyclopentylpiperidin-4-yloxy)-5-(1H-pyridin-2-on-4-yl)pyrimidine,
2-(1-cyclopentylpiperidin-4-yloxy)-5-(1-methyl-1H-pyridin-2-on-4-yl)pyrimidine,
2-(1-cyclopentylpiperidin-4-yloxy)-5-(2-difluoromethoxypyridin-4-yl)pyrimidine,
2-(1-cyclopentylpiperidin-4-yloxy)-5-(1-difluoromethyl-1H-pyridin-2-on-4-yl)pyrimidine,
2-(1-cyclopentylpiperidin-4-yloxy)-5-{4-(N-methyl-N-methoxycarbonylamino)phenyl}pyrimidine,
2-(1-cyclopentylpiperidin-4-yloxy)-5-(1-ethyl-1H-pyridin-2-on-4-yl)pyrimidine,
2-(1-cyclopentylpiperidin-4-yloxy)-5-(1-methyl-1H-pyridin-2-on-5-yl)pyrimidine,
2-(1-cyclopentylpiperidin-4-yloxy)-5-(1-ethyl-1H-pyridin-2-on-5-yl)pyrimidine,
2-(1-cyclopentylpiperidin-4-yloxy)-5-(2-methylimidazo[1,2,a]pyridin-6-yl)pyrimidine,
2-(1-cyclopentylpiperidin-4-yloxy)-5-(2-carbamoylpyridin-5-yl)pyrimidine,
2-(1-cyclopentylpiperidin-4-yloxy)-5-{1-(2,2-difluoroethyl)-1H-pyridin-2-on-4-yl}pyrimidine,
2-(1-cyclopentylpiperidin-4-yloxy)-5-(1,2,4-triazolo[4,3,a]pyridin-7-yl)pyrimidine,
2-(1-cyclopentylpiperidin-4-yloxy)-5-(1,2,4-triazolo[4,3,a]pyridin-6-yl)pyrimidine,
2-(1-cyclopentylpiperidin-4-yloxy)-5-(1-methyl-1H-pyridin-2-on-5-yl)pyridine,
2-(1-cyclopentylpiperidin-4-yloxy)-5-(1-difluoromethyl-1H-pyridin-2-on-5-yl)pyridine,
2-(1-cyclobutylpiperidin-4-yloxy)-5-(1-difluoromethyl-1H-pyridin-2-on-4-yl)pyrimidine,
2-(1-cyclobutylpiperidin-4-yloxy)-5-(1-methyl-1H-pyridin-2-on-5-yl)pyridine,
2-(1-cyclobutylpiperidin-4-yloxy)-5-{1-(2-fluoroethyl)-1H-pyridin-2-on-4-yl}pyridine,
2-(1-cyclopentylpiperidin-4-yloxy)-5-{1-(2-fluoroethyl)-1H-pyridin-2-on-4-yl}pyrimidine,
2-(1-isopropylpiperidin-4-yloxy)-5-(1-methyl-1H-pyridin-2-on-5-yl)pyridine,
2-(1-cyclobutylpiperidin-4-yloxy)-5-{1-(2-fluoroethyl)-1H-pyridin-2-on-5-yl}pyridine,
2-(1-cyclobutylpiperidin-4-yloxy)-5-{1-(2-fluoroethoxy-1H-pyridin-2-on-5-yl}pyridine,
2-(1-cyclobutylpiperidin-4-yloxy)-5-{1-(2-fluoroethyl-1H-pyridin-2-on-4-yl}pyridine,
2-(1-cyclobutylpiperidin-4-yloxy)-5-(3-chloro-1-methyl-1H-pyridin-2-on-5-yl)pyridine,
2-(1-cyclobutylpiperidin-4-yloxy)-5-(1-ethyl-1H-pyridin-2-on-5-yl)pyridine,
2-(1-isopropylpiperidin-4-yloxy)-5-(1-ethyl-1H-pyridin-2-on-5-yl)pyridine.

(13) A histamine-H3 receptor antagonist or inverse-agonist containing, as the active ingredient thereof, a compound of any of above (1) to (12).

(14) A histamine-H3 receptor antagonist containing, as the active ingredient thereof, a compound of any of above (1) to (12).

(15) A histamine-H3 receptor inverse-agonist containing, as the active ingredient thereof, a compound of any of above (1) to (12).

(16) A preventive or remedy comprising, as the active ingredient thereof, a compound of any of above (1) to (7), which is for metabolic system diseases such as obesity, diabetes, hormone secretion disorder, hyperlipemia, gout, fatty liver; circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder; and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

(17) A method for producing a compound of a general formula (I-2) or a compound of a general formula (I-3) or a salt thereof, which comprises reacting a compound of a general formula (IV):

(VI)

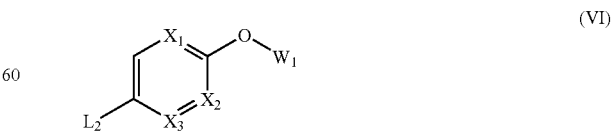

[wherein $X^1$, $X^2$ and $X^3$ each independently represent N or CH (provided that all of $X^1$, $X^2$ and $X^3$ are not CH at the same time); $W^1$ represents a group of the following formula (II-1):

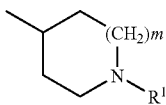

(II-1)

(wherein m indicates an integer of from 0 to 3; $R^1$ represents a linear or branched lower alkyl group (excepting a methyl group), a cycloalkyl group having from 3 to 9 carbon atoms, an aralkyl group or a heterocyclic group having from 3 to 8 carbon atoms (the hetero ring has 1 or 2 nitrogen atoms or oxygen atoms), which may be substituted with a group selected from a class consisting of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbonyl group and a trifluoromethyl group, or represents a group corresponding to R but having a protective group suitably introduced into the substituent which R has), or represents a group or a formula (III):

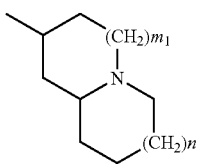

(III)

(wherein m1 indicates an integer of from 0 to 3; n indicates an integer of from 0 to 2); and L3 represents a leaving group], with a compound of a general formula (XI):

Met-$Y^{1p}$ (XI)

[wherein Met represents a general organic metal atom; $Y^{1p}$ represents a group of a formula (IV):

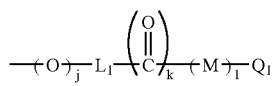

(IV)

(wherein j, k and l each independently indicate 0 or 1; L1 represents a lower alkylene group having from 1 to 4 carbon atoms, or a single bond; M represents an oxygen atom or a group of a formula (V):

(V)

(wherein $R^0$ represents a lower alkyl group having from 1 to 4 carbon atoms); $Q_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have 1 or 2 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a group corresponding to $Q^1$ but having a protective group optionally introduced into the substituent which $Q^1$ has, or represents a group of a formula (V-1):

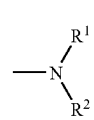

(V-1)

(wherein $R^1$ and $R^2$ are the same or different, each representing a lower alkyl group or a mono- or di-lower alkylcarbamoyl group, or $R^1$ and $R^2$ together form, along with the adjacent nitrogen atom, a 3- to 9-membered lactam ring, a heterocyclic group having from 3 to 8 carbon atoms (the group has 1 or 2 nitrogen atoms or oxygen atoms in the ring thereof), a 5-membered heteroaryl group or a condensed-cyclic heteroaryl group), or represents a group corresponding to —Y but having a protective group optionally introduced into the substituent which —Y has], in the presence of a catalyst, to give a compound of a general formula (VIII):

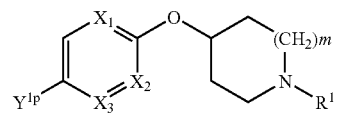

(VIII)

(wherein $X^1$, $X^2$, $X^3$, m, $R^1$ and $Y^{1p}$ have the same meanings as above), or a compound of a general formula (IX):

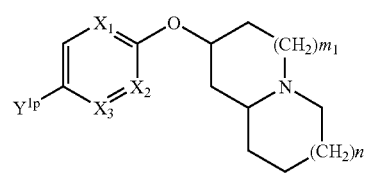

(IX)

(wherein $X^1$, $X^2$, $X^3$, $m^1$, n and $Y^{1p}$ have the same meanings as above), and optionally removing the protective group to give a compound of a general formula (I-2):

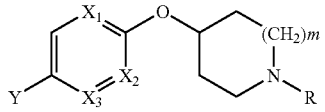
(I-2)

(wherein $X^1$, $X^2$, $X^3$, m, R and Y have the same meanings as above), or a compound of a general formula (I-3):

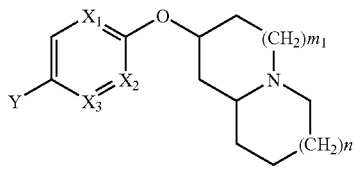
(I-3)

(wherein $X^1$, $X^2$, $X^3$, $m^1$, n and Y have the same meanings as above), or a salt thereof.

(18) A method for producing a compound of a general formula (I-2) or a compound of a general formula (I-3) or a salt thereof, which comprises reacting a compound of a general formula (X):

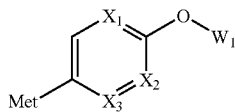
(X)

[wherein $X^1$, $X^2$ and $X^3$ each independently represent N or CH (provided that all of $X^1$, $X^2$ and $X^3$ are not CH at the same time); $W^1$ represents a group of the following formula (II-1):

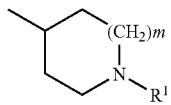
(II-1)

(wherein m indicates an integer of from 0 to 3; $R^1$ represents a linear or branched lower alkyl group (excepting a methyl group), a cycloalkyl group having from 3 to 9 carbon atoms, an aralkyl group or a heterocyclic group having from 3 to 8 carbon atoms (the hetero ring has 1 or 2 nitrogen atoms or oxygen atoms), which may be substituted with a group selected from a class consisting of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbonyl group and a trifluoromethyl group), or represents a group corresponding to R but having a protective group suitably introduced into the substituent which R has, or represents a group or a formula (III):

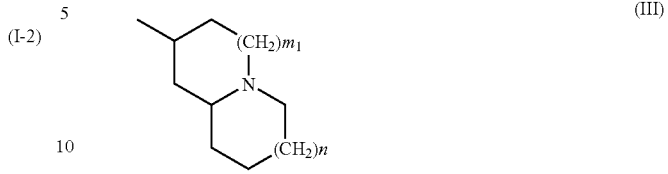
(III)

(wherein m1 indicates an integer of from 0 to 3; n indicates an integer of from 0 to 2); and Met represents a general organic metal atom], with a compound of a general formula (XI):

$$L_2\text{-}Y^{1p}$$ (XI)

[wherein $L_2$ represents a leaving group; $Y^{1p}$ represents a group of a formula (IV):

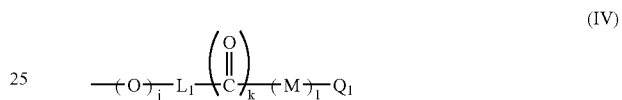
(IV)

(wherein j, k and l each independently indicate 0 or 1; $L_1$ represents a lower alkylene group having from 1 to 4 carbon atoms, or a single bond; M represents an oxygen atom or a group of a formula (V):

(V)

(wherein $R^0$ represents a lower alkyl group having from 1 to 4 carbon atoms); $Q_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have 1 or 2 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a group corresponding to $Q^1$ but having a protective group optionally introduced into the substituent which $Q^1$ has, or represents a group of a formula (V-1):

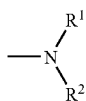
(V-1)

(wherein $R^1$ and $R^2$ are the same or different, each representing a lower alkyl group or a mono- or di-lower alkylcarbamoyl group, or $R^1$ and $R^2$ together form, along with the adjacent nitrogen atom, a 3- to 9-membered lactam ring, a heterocyclic group having from 3 to 8 carbon atoms (the group has 1 or 2 nitrogen atoms or oxygen atoms in the ring thereof), a 5-membered heteroaryl group or a condensed-cyclic heteroaryl group), or represents a group corresponding to —Y but having a protective group optionally introduced into the substituent which —Y has], in the presence of a catalyst, to give a compound of a general formula (XII):

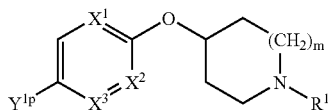
(XII)

(wherein $X^1$, $X^2$, $X^3$, m, $R^1$ and $Y^{1p}$ have the same meanings as above), or a compound of a general formula (XIII):

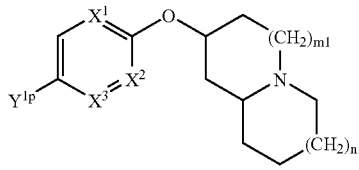
(XIII)

(wherein $X^1$, $X^2$, $X^3$, $m^1$, n and $Y^{1p}$ have the same meanings as above), and optionally removing the protective group to give a compound of a general formula (I-2):

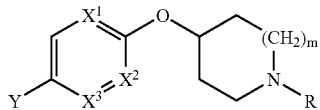
(I-2)

(wherein $X^1$, $X^2$, $X^3$, m, R and Y have the same meanings as above), or a compound of a general formula (I-3):

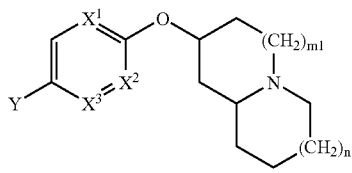
(I-3)

(wherein $X^1$, $X^2$, $X^3$, $m^1$, n and Y have the same meanings as above), or a salt thereof.

(19) A method for producing a compound (I) of the invention, which comprises reacting a compound of a general formula (XIV):

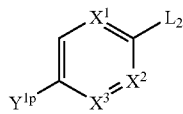
(XIV)

[wherein $X^1$, $X^2$ and $X^3$ each independently represent N or CH (provided that all of $X^1$, $X^2$ and $X^3$ are not CH at the same time); $Y^{1p}$ represents a group of a formula (IV):

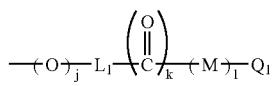
(IV)

((wherein j, k and l each independently indicate 0 or 1; $L_1$ represents a lower alkylene group having from 1 to 4 carbon atoms, or a single bond; M represents an oxygen atom or a group of a formula (V):

(V)

(wherein $R^0$ represents a lower alkyl group having from 1 to 4 carbon atoms); $Q_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have 1 or 2 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a group corresponding to $Q^1$ but having a protective group optionally introduced into the substituent which $Q^1$ has, or represents a group of a formula (V-1):

 (V-1)

(wherein R¹ and R² are the same or different, each representing a lower alkyl group or a lower alkylcarbamoyl group having from 1 to 6 carbon atoms, or R¹ and R² together form, along with the adjacent nitrogen atom, a 3- to 9-membered lactam ring, a heterocyclic group having from 3 to 8 carbon atoms (the group has 1 or 2 nitrogen atoms or oxygen atoms in the ring thereof), a 5-membered heteroaryl group or a condensed-cyclic heteroaryl group), or represents a group corresponding to —Y but having a protective group optionally introduced into the substituent which —Y has; $L_2$ represents a leaving group], with a compound of a general formula (XV):

 (XV)

[wherein $W^1$ represents a group of the following formula (II-p):

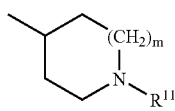 (II-p)

(wherein $R^{11}$ is $R^1$ or an amino-protective group; and the other symbols have the same meanings as above), or represents a group of a formula (III):

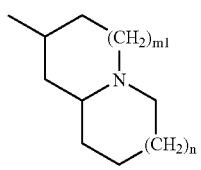 (III)

(wherein the symbols have the same meanings as above)] or its salt to give a compound of a general formula (XVI):

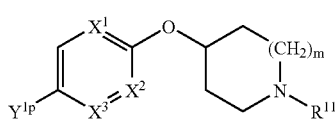 (XVI)

[wherein $X^1$, $X^2$, $X^3$, $Y^{1p}$, m and $R^{11}$ have the same meanings as above], and when the compound and $R^{11}$ have a protective group for the amino group therein, then removing the amino-protective group, and thereafter further reacting it with a precursor aldehyde or ketone corresponding to $R^1$ or with a compound of a general formula (XVII):

 (XVII)

(wherein the symbols have the same meanings as above), and optionally removing the protective group to give a compound (I) of the invention:

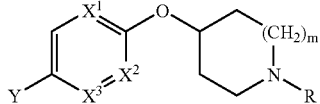 (I)

(wherein the symbols have the same meanings as above].

The meanings of the terms used herein are mentioned below, and the compounds of the invention are described in more detail hereinunder.

"Aryl group" includes a hydrocarbon-cyclic aryl having from 6 to 14 carbon atoms, for example, a phenyl group, a naphthyl group, a biphenyl group, an anthryl group.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Alkylene group" means a linear or branched alkylene group having from 1 to 6 carbon atoms, including, for example, a methylene group, an ethylene group, a trimethylene group, a tetramethylene group, a pentamethylene group.

"Cycloalkyl group having from 3 to 9 carbon atoms" includes, for example, a cyclopropyl group, a cyclobutyl group, a cyclopentyl group, a cyclohexyl group, a cycloheptyl group, a cyclooctyl group, a cyclononyl group.

"Alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Alkylsulfonyl group" means a group comprising a sulfonyl group bonding to the above-mentioned alkyl group, including, for example, a methylsulfonyl group, an ethylsulfonyl group, a propylsulfonyl group, an isopropylsulfonyl group, a butylsulfonyl group.

"Alkylsulfonylamino group" means an amino group of which one hydrogen atom is substituted with the above-mentioned alkylsulfonyl group, including, for example, a methylsulfonylamino group, an ethylsulfonylamino group, a propylsulfonylamino group, an isopropylsulfonylamino group, a butylsulfonylamino group, a sec-butylsulfonylamino group, a tert-butylsulfonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulfonylamino group, an N-methyl-sec-butylsulfonylamino group, an N-methyl-tert-butylsulfonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulfonylamino group, an N-ethyl-sec-butylsulfonylamino group, an N-ethyl-tert-butylsulfonylamino group.

"Cyclo-lower alkylsulfonyl group" means a group comprising a sulfonyl group bonding to the above-mentioned "cycloalkyl group having from 3 to 9 carbon atoms", including, for example, a cyclopropylsulfonyl group, a cyclobutylsulfonyl group, a cyclopentylsulfonyl group, a cyclohexylsulfonyl group, a cycloheptylsulfonyl group, a cyclooctylsulfonyl group, a cyclononylsulfonyl group.

"Aralkyl group" means the above-mentioned alkyl group having the above-mentioned aryl group, including, for example, a benzyl group, a 1-phenylethyl group, a 2-phenylethyl group, a 1-naphthylmethyl group, a 2-naphthylmethyl group.

"Hetero-aryl group" means a 5- to 7-membered monocyclic group having therein from 1 to 3 hetero atoms selected from a group consisting of an oxygen atom, a sulfur atom and a nitrogen atom, or a bicyclic hetero-aryl group comprising the mono-cyclic heteroaryl group condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, a quinoxalinyl group, a cinnolinyl group, a benzimidazolyl group, an imidazopyridyl group, a triazolopyridine group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group.

"Halogen atom" means, for example, a fluorine atom, a chlorine atom, a bromine atom, an iodine atom.

"Alkoxycarbonylamino group" means an amino group of which one hydrogen atom is substituted with the above-mentioned alkoxycarbonyl group, including, for example, a methoxycarbonylamino group, an ethoxycarbonylamino group, a propoxycarbonylamino group, an isopropoxycarbonylamino group, a butoxycarbonylamino group, a sec-butoxycarbonylamino group, a tert-butoxycarbonylamino group, a pentyloxycarbonylamino group, an (N-methyl)methoxycarbonylamino group, an (N-methyl)ethoxycarbonylamino group, an (N-methyl)propoxycarbonylamino group, an (N-methyl)isopropoxycarbonylamino group, an (N-methyl)butoxycarbonylamino group, an (N-methyl)-sec-butoxycarbonylamino group, an (N-methyl)-tert-butoxycarbonylamino group, an (N-ethyl)methoxycarbonylamino group, an (N-ethyl)ethoxycarbonylamino group, an (N-ethyl)propoxycarbonylamino group, an (N-ethyl)isopropoxycarbonylamino group, an (N-ethyl)butoxycarbonylamino group, an (N-ethyl)-sec-butoxycarbonylamino group, an (N-ethyl)-tert-butoxycarbonylamino group.

"Hydroxyalkyl group" means a group derived from the above-mentioned alkyl group by substituting one hydrogen atom thereof with a hydroxyl group, including, for example, a hydroxymethyl group, a hydroxyethyl group, a 1-hydroxypropyl group, a 1-hydroxyethyl group, a 2-hydroxypropyl group, a 2-hydroxy-1-methylethyl group.

"Mono-lower alkylcarbamoyl group" means a carbamoyl group mono-substituted with the above-mentioned lower alkyl group, including, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group.

"Di-lower alkylcarbamoyl group" means a carbamoyl group di-substituted with the above-mentioned, same or different lower alkyl groups, and the "di-lower alkylcarbamoyl group" includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

"Di-lower alkylcarbamoyl group" includes a 5- to 8-membered monocyclic group formed by the nitrogen atom constituting the carbamoyl group and the same or different lower alkyl groups bonding to the nitrogen atom, or includes a bicyclic group comprising the monocyclic group and a benzene ring or a pyridine ring bonding thereto. Concretely, for example, it includes the following groups:

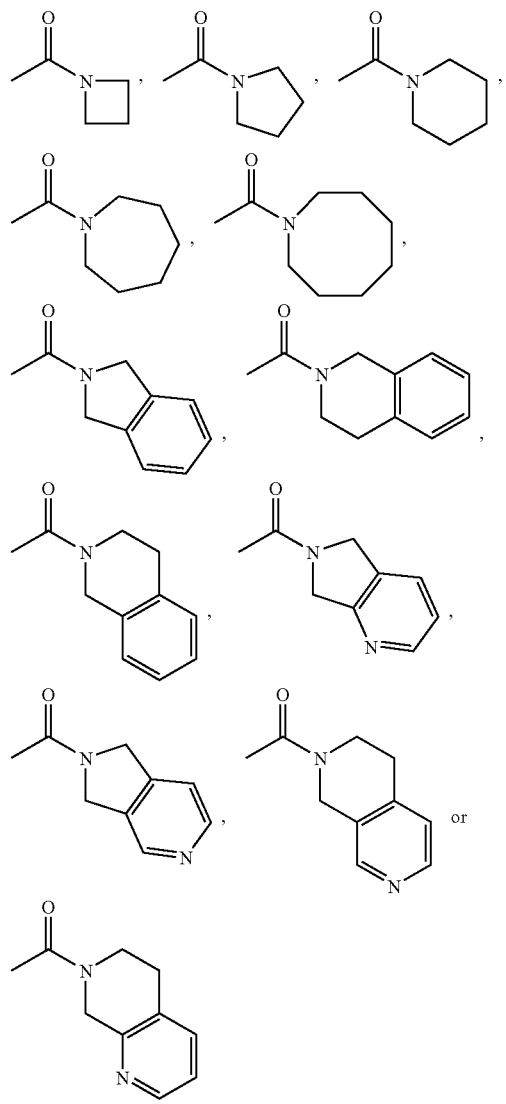

"Alkylamino group" means an amino group mono-substituted with the above-mentioned lower alkyl group, including, for example, a methylamino group, an ethylamino group, a propylamino group, an isopropylamino group, a butylamino group, a sec-butylamino group, a tert-butylamino group.

"Dialkylamino group" means an amino group di-substituted with the above-mentioned, same or different lower alkyl groups, including, for example, a dimethylamino group, a diethylamino group, a dipropylamino group, a methylpropylamino group, a diisopropylamino group.

"Aminoalkyl group" means a group derived from the above-mentioned alkyl group by substituting one hydrogen atom constituting it with an amino group, including, for example, an aminomethyl group, an aminoethyl group, an aminopropyl group.

"Alkanoyl group" means a group comprising a carbonyl group bonding to the above-mentioned alkyl group, including, for example, a methylcarbonyl group, an ethylcarbonyl group, a propylcarbonyl group, an isopropylcarbonyl group.

"Alkanoylamino group" means a group comprising an amino group bonding to the above-mentioned alkanoyl group, including, for example, an acetylamino group, a propanoylamino group, a butanoylamino group, a pentanoylamino group, an N-methyl-acetylamino group, an N-methyl-propanoylamino group, an N-methyl-butanoylamino group, an N-methyl-pentanoylamino group, an N-ethyl-acetylamino group, an N-ethyl-propanoylamino group, an N-ethyl-butanoylamino group, an N-ethyl-pentanoylamino group.

"Mono-lower alkylaminocarbonyloxy group" means a carbonyloxy group mono-substituted with the above-mentioned lower alkyl group, including, for example, a methylaminocarbonyloxy group, an ethylaminocarbonyloxy group, a propylaminocarbonyloxy group, an isopropylaminocarbonyloxy group.

"Di-lower alkylaminocarbonyloxy group" means a carbonyloxy group di-substituted with the above-mentioned lower alkyl group, including, for example, a dimethylaminocarbonyloxy group, a diethylaminocarbonyloxy group, a diisopropylaminocarbonyloxy group, an ethylmethylaminocarbonyloxy group.

For more concretely disclosing the compounds of formula (I) of the invention, various symbols used in formula (I) are mentioned below with reference to their specific examples.

Group of formula (I-1):

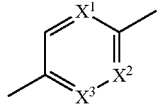
(I-1)

[wherein $X^1$, $X^2$ and $X^3$ each independently represent N or CH (provided that all of $X^1$, $X^2$ and $X^3$ are not CH at the same time)].

Of $X^1$, $X^2$ and $X^3$, it is desirable that at least one of $X^1$ or $X^2$ is a nitrogen atom or both $X^2$ and $X^3$ are nitrogen atoms.

Accordingly, preferred examples of formula (I-1) are more concretely as follows:

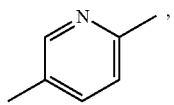
(I-10)

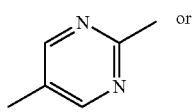
(I-11) or

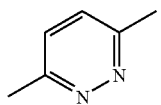
(I-12)

W in formula (I) means a group of a formula (II):

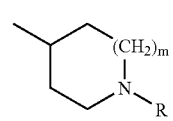
(II)

[wherein the symbols have the same meanings as above], or a group of a formula (III):

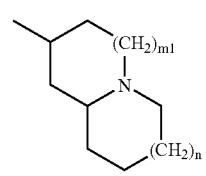
(III)

[wherein the symbols have the same meanings as above].

m in formula (II) is an integer of from 0 to 3.

R in formula (II) is a linear or branched lower alkyl group (excepting a methyl group), a cycloalkyl group having from 3 to 9 carbon atoms, an aralkyl group or a heterocyclic group having from 3 to 8 carbon atoms (the ring has 1 or 2 nitrogen atoms or oxygen atoms), which may be substituted with a group selected from a class consisting of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbonyl group and a trifluoromethyl group.

"Linear or branched lower alkyl group" represented by R in formula (II) has the same meaning as the above-defined lower alkyl group (excepting a methyl group), and includes, for example, an ethyl group, a propyl group, a butyl group, an isopropyl group, an isobutyl group, a tert-butyl group, a pentyl group, an isoamyl group, a neopentyl group, a 1,1-dimethylpropyl group, a 1-methylbutyl group, a 2-methylbutyl group, a hexyl group, an isohexyl group, a 1-methylpentyl group, a 1,1-dimethylbutyl group. Of these, preferred are a propyl group, a butyl group, an isopropyl group, an isobutyl group, a tert-butyl group, a pentyl group, an isoamyl group, a neopentyl group, a 1,1-dimethylpropyl group, a 1-methylbutyl group, a hexyl group and an isohexyl group; and of those, more preferred are an isopropyl group, an isobutyl group, a tert-butyl group, a pentyl group, an isoamyl group, a neopentyl group, a 1,1-dimethylpropyl group and a 1-methylbutyl group.

When R is a "linear or branched lower alkyl group", then the substituent that the lower alkyl group may have is preferably a cyano group, a hydroxyl group, a lower alkoxy group (the lower alkoxy group may be substituted with a halogen atom), a halogen atom, a di-lower alkylaminocarbonyloxy group, a di-lower alkylcarbamoyl group or a trifluoromethyl group of the substituents mentioned above, and more preferably a hydroxyl group, a lower alkoxy group (the lower alkoxy group may be substituted with a halogen atom) or a trifluoromethyl group.

"Lower alkyl group substituted with a cyano group" represented by R includes more concretely, for example, a 1-cyanoethyl group, a 2-cyanoethyl group, a 2-cyano-1,1-dimethyl-ethyl group, a 5-cyanopentyl group, a 4-cyanopentyl group, a 3-cyanopentyl group, a 2-cyanopentyl group, a 2-cyanopentyl group, a 1-cyanopentyl group, a 3-cyano-1-methylpropyl group, a 2-cyano-1-methylethyl group, a 1-cyanomethylpropyl group.

"Lower alkyl group substituted with a hydroxy group" represented by R includes more concretely, for example, a 1-hydroxyethyl group, a 2-hydroxyethyl group, a 1-hydroxypropyl group, a 2-hydroxypropyl group, a 5-hydroxypentyl group, a 4-hydroxypentyl group, a 3-hydroxypentyl group, a 2-hydroxypentyl group, a 1-hydroxypentyl group, a 1-hydroxyethyl group, a 2-hydroxyethyl group, a 2-hydroxy-1-methylethyl group, a 2-hydroxy-1-methylethyl group, a 3-hydroxy-1-methylpropyl group, a 1-hydroxymethylpropyl group, a 1,1-dimethyl-2-hydroxyethyl group.

"Lower alkyl group substituted with an alkoxy group (the alkoxy group may be substituted with a halogen atom)" represented by R includes more concretely, for example, a 2-(2-chloroethoxy)ethyl group, a 2-(chloromethoxy)ethyl group, a 1-methoxyethyl group, a 2-methoxyethyl group, a 2-methoxy-1-methylethyl group, a 2-chloromethoxy-1-methylethyl group, a 3-methoxy-1-methylpropyl group, a 1-(methoxymethyl)propyl group, a 3-(chloromethoxy)-1-methylpropyl group, a 1-(chloromethoxymethyl)propyl group, a 1,1-dimethyl-2-methoxyethyl group, a 2-(chloromethoxy)-1,1-dimethylethyl group, a 5-methoxypentyl group, a 4-methoxypentyl group, a 3-methoxypentyl group, a 2-methoxypentyl group, a 1-methoxypentyl group.

"Lower alkyl group substituted with a halogen atom" represented by R includes more concretely, for example, a 1-fluoroethyl group, a 2-fluoroethyl group, a 2-fluoro-1-methylethyl group, a 3-fluoro-1-methylpropyl group, a 2,2-difluoroethyl group, a 2,2,2-trifluoroethyl group, a 1-fluoromethylpropyl group, a 3,3-difluoropropyl group, a 3,3,3-trifluoropropyl group, a 2-fluoro-1,1-dimethylethyl group, a 1-chloroethyl group, a 2-chloroethyl group, a 2-chloro-1-methylethyl group, a 3-chloro-1-methylpropyl group, a 1-chloromethylpropyl group, a 2-chloro-1,1-dimethylethyl group.

"Lower alkyl group substituted with a mono-lower alkylaminocarbonyloxy group" represented by R includes more concretely, for example, a 2-(ethylaminocarbonyloxy)ethyl group, a 2-(propylaminocarbonyloxy)ethyl group, a 2-(isopropylaminocarbonyloxy)ethyl group.

"Lower alkyl group substituted with a dialkylaminocarbonyloxy group" represented by R includes more concretely, for example, a 1-(dimethylaminocarbonyloxy)ethyl group, a 2-(dimethylaminocarbonyloxy)ethyl group, a 1-(diethylaminocarbonyloxy)ethyl group, a 2-(diethylaminocarbonyloxy)ethyl group, a 1-(diisopropylaminocarbonyloxy)ethyl group, a 2-(dimethylaminocarbonyloxy)-1-methyl-ethyl group, a 2-(diethylcarbonyloxy)-1-methylethyl group, a 2-(diisopropylaminocarbonyloxy)-1-methylethyl group.

"Lower alkyl group substituted with a dialkylcarbamoyl group" represented by R includes more concretely, for example, a 2-(methylcarbamoyl)ethyl group, a 1-(methylcarbamoyl)ethyl group.

"Lower alkyl group substituted with a carbamoyl group" represented by R includes more concretely, for example, a 2-carbamoylethyl group, a 3-carbamoylethyl group, a 2-carbamoyl-1-methylethyl group.

"Lower alkyl group substituted with a trifluoromethyl group" represented by R includes more concretely, for example, a 3,3,3-trifluoropropyl group, a 2,2,2-trifluoro-1-methylethyl group, a 4,4,4-trifluorobutyl group, a 3,3,3-trifluoro-1-methylpropyl group.

"Lower alkyl group substituted with a lower alkylsulfonyl group" represented by R includes more concretely, for example, a 2-methanesulfonylethyl group, a 1-methanesulfonylethyl group, a 2-ethanesulfonylethyl group, a 2-methanesulfonyl-1-methylethyl group.

"Lower alkyl group substituted with a cyclo-lower alkylsulfonyl group" represented by R includes more concretely, for example, a 2-cyclopropanesulfonylethyl group, a 1-cyclopropanesulfonylethyl group, a 3-cyclobutanesulfonylpropyl group, a 2-cyclobutanesulfonylpropyl group.

"Cycloalkyl group having from 3 to 9 carbon atoms" for R is described below.

"Cycloalkyl group having from 3 to 9 carbon atoms" represented by R in formula (II) has the same meaning as defined hereinabove, including, for example, a cyclopropyl group, a cyclobutyl group, a cyclopentyl group, a cyclohexyl group, a cycloheptyl group, a cyclooctyl group. Of those, preferred are a cyclopropyl group, a cyclobutyl group, a cyclopentyl group and a cyclohexyl group; and more preferred are a cyclopropyl group, a cyclobutyl group and a cyclopentyl group.

When R is a "cycloalkyl group having from 3 to 9 carbon atoms", then the substituent that the cycloalkyl group having from 3 to 9 carbon atoms may have is preferably a cyano group, a hydroxyl group, a lower alkoxy group (the lower alkoxy group may be substituted with a halogen atom), a lower alkyl group (the alkoxy group may be substituted with a halogen atom), a halogen atom, a di-lower alkylaminocarbonyloxy group, a di-lower alkylcarbamoyl group or a trifluoromethyl group of the substituents mentioned above, and more preferably a cyano group, a hydroxyl group, a lower alkoxy group (the lower alkoxy group may be substituted with a halogen atom), a halogen atom or a trifluoromethyl group.

The cycloalkyl group having from 3 to 9 carbon atoms may have one or two and the same or different groups of these substituents at any bondable position.

"Cycloalkyl group substituted with a lower alkyl group" represented by R includes more concretely, for example, a 1-methylcyclopropyl group, a 1-ethylcyclopropyl group, a 1-methylcyclobutyl group, a 1-ethylcyclobutyl group, a 1-methylcyclopentyl group, a 1-ethylcyclopentyl group, a 1-methylcyclohexyl group, a 1-ethylcyclohexyl group, a 1-methylcycloheptyl group, a 1-ethylcycloheptyl group, a 1-methylcyclooctyl group, a 1-ethylcyclooctyl group.

"Cycloalkyl group substituted with a cyano group" represented by R includes more concretely, for example, a 2-cyanocyclopropyl group, a 3-cyanocyclopropyl group, a 2-cyanocyclobutyl group, a 2-cyanocyclopentyl group, a 3-cyanocyclopentyl group, a 2-cyanocyclohexyl group, a 3-cyanocyclohexyl group, a 4-cyanocyclohexyl group, a 2-cyanocycloheptyl group, a 3-cyanocycloheptyl group, a 4-cyanocycloheptyl group, a 2-cyanocyclooctyl group, a 3-cyanocyclooctyl group, a 4-cyanocyclooctyl group, a 5-cyanocyclooctyl group.

"Cycloalkyl group substituted with a hydroxyl group" represented by R includes more concretely, for example, a 2-hydroxycyclopropyl group, a 3-hydroxycyclobutyl group, a 2-hydroxycyclobutyl group, a 2-hydroxycyclopentyl group, a 3-hydroxycyclopentyl group, a 2-hydroxycyclohexyl group, a 3-hydroxycyclohexyl group, a 4-hydroxycyclohexyl group, a 2-hydroxycycloheptyl group, a 3-hydroxycycloheptyl group, a 4-hydroxycycloheptyl group, a 2-hydroxycyclooctyl group, a 3-hydroxycyclooctyl group, a 4-hydroxycyclooctyl group, a 5-hydroxycyclooctyl group.

"Cycloalkyl group substituted with an alkoxy group (the alkoxy group may be substituted with a halogen atom)" represented by R includes more concretely, for example, a 2-chloromethoxycyclopropyl group, a 2-methoxycyclopropyl group, a 2-ethoxycyclopropyl group, a 2-(chloromethoxy)cyclobutyl group, a 3-methoxycyclobutyl group, a 2-(chloromethoxy)cyclopentyl group, a 2-methoxycyclopentyl group, a 3-methoxycyclopentyl group, a 2-(chloromethoxy)cyclohexyl group, a 2-methoxycyclohexyl group, a 3-methoxycyclohexyl group, a 4-methoxycyclohexyl group, a 2-(chloromethoxy)cycloheptyl group, a 2-methoxycycloheptyl group, a 3-methoxycycloheptyl group, a 4-methoxycycloheptyl group, a 2-(chloromethoxy)cyclooctyl group, a 2-methoxycyclooctyl group, a 3-methoxycyclooctyl group, a 4-methoxycyclooctyl group, a 5-methoxycyclooctyl group.

"Cycloalkyl group substituted with a halogen atom" represented by R includes more concretely, for example, a 2-fluorocyclopropyl group, a 3-fluorocyclobutyl group, a 2-fluorocyclobutyl group, a 2-fluorocyclopentyl group, a 3-fluorocyclopentyl group, a 2-fluorocyclohexyl group, a 3-fluorocyclohexyl group, a 4-fluorocyclohexyl group, a 2-fluorocyclopentyl group, a 3-fluorocycloheptyl group, a 4-fluorocycloheptyl group, a 2-fluorocyclooctyl group, a 3-fluorocyclooctyl group, a 4-fluorocyclooctyl group, a 5-fluorocyclooctyl group, a 2-chlorocyclopropyl group, a 3-chlorocyclobutyl group, a 2-chlorocyclobutyl group, a 2-chlorocyclopentyl group, a 3-chlorocyclopentyl group, a 2-chlorocyclohexyl group, a 3-chlorocyclohexyl group, a 4-chlorocyclohexyl group, a 2-chlorocycloheptyl group, a 3-chlorocycloheptyl group, a 4-chlorocycloheptyl group, a 2-chlorocyclooctyl group, a 3-chlorocyclooctyl group, a 4-chlorocyclooctyl group, a 5-chlorocyclooctyl group.

"Cycloalkyl group substituted with a mono-lower alkylaminocarbonyloxy group" represented by R includes more concretely, for example, a 2-(methylcarbamoyloxy)cyclopropyl group, a 3-(methylcarbamoyloxy)cyclobutyl group, a 2-(methylcarbamoyloxy)cyclobutyl group, a 2-(methylcarbamoyloxy)cyclopentyl group, a 3-(methylcarbamoyloxy)cyclopentyl group, a 2-(methylcarbamoyloxy)cyclohexyl group, a 3-(methylcarbamoyloxy)cyclohexyl group, a 4-(methylcarbamoyloxy)cyclohexyl group, a 2-(methylcarbamoyloxy)cycloheptyl group, a 3-(methylcarbamoyloxy)cycloheptyl group, a 4-(methylcarbamoyloxy)cycloheptyl group, a 2-(methylcarbamoyloxy)cyclooctyl group, a 3-(methylcarbamoyloxy)cyclooctyl group, a 4-(methylcarbamoyloxy)cyclooctyl group, a 5-(methylcarbamoyloxy)cyclooctyl group.

"Cycloalkyl group substituted with a di-lower alkylaminocarbonyloxy group" represented by R includes more concretely, for example, a 2-(dimethylcarbamoyloxy)cyclopropyl group, a 3-(dimethylcarbamoyloxy)cyclobutyl group, a 2-(dimethylcarbamoyloxy)cyclobutyl group, a 2-(dimethylcarbamoyloxy)cyclopentyl group, a 3-(dimethylcarbamoyloxy)cyclopentyl group, a 2-(dimethylcarbamoyloxy)cyclohexyl group, a 3-(dimethylcarbamoyloxy)cyclohexyl group, a 4-(dimethylcarbamoyloxy)cyclohexyl group, a 2-(dimethylcarbamoyloxy)cycloheptyl group, a 3-(dimethylcarbamoyloxy)cycloheptyl group, a 4-(dimethylcarbamoyloxy)cycloheptyl group, a 2-(dimethylcarbamoyloxy)cyclooctyl group, a 3-(dimethylcarbamoyloxy)cyclooctyl group, a 4-(dimethylcarbamoyloxy)cyclooctyl group, a 5-(dimethylcarbamoyloxy)cyclooctyl group.

"Cycloalkyl group substituted with a dialkylcarbamoyl group" represented by R includes more concretely, for example, a 2-(dimethylcarbamoyl)cyclopropyl group, a 3-(dimethylcarbamoyl)cyclobutyl group, a 2-(dimethylcarbamoyl)cyclobutyl group, a 2-(dimethylcarbamoyl)cyclopentyl group, a 3-(dimethylcarbamoyl)cyclopentyl group, a 2-(dimethylcarbamoyl)cyclohexyl group, a 3-(dimethylcarbamoyl)cyclohexyl group, a 4-(dimethylcarbamoyl)cyclohexyl group, a 2-(dimethylcarbamoyl)cycloheptyl group, a 3-(dimethylcarbamoyl)cycloheptyl group, a 4-(dimethylcarbamoyl)cycloheptyl group, a 2-(dimethylcarbamoyl)cyclooctyl group, a 3-(dimethylcarbamoyl)cyclooctyl group, a 4-(dimethylcarbamoyl)cyclooctyl group, a 5-(dimethylcarbamoyl)cyclooctyl group.

"Cycloalkyl group substituted with an alkylcarbamoyl group" represented by R includes more concretely, for example, a 2-(methylcarbamoyl)cyclopropyl group, a 3-(methylcarbamoyl)cyclobutyl group, a 2-(methylcarbamoyl)cyclobutyl group, a 2-(methylcarbamoyl)cyclopentyl group, a 3-(methylcarbamoyl)cyclopentyl group, a 2-(methylcarbamoyl)cyclohexyl group, a 3-(methylcarbamoyl)cyclohexyl group, a 4-(methylcarbamoyl)cyclohexyl group, a 2-(methylcarbamoyl)cycloheptyl group, a 3-(methylcarbamoyl)cycloheptyl group, a 4-(methylcarbamoyl)cycloheptyl group, a 2-(methylcarbamoyl)cyclooctyl group, a 3-(methylcarbamoyl)cyclooctyl group, a 4-(methylcarbamoyl)cyclooctyl group, a 5-(methylcarbamoyl)cyclooctyl group.

"Cycloalkyl group substituted with a carbamoyl group" represented by R includes more concretely, for example, a 2-carbamoylcyclopropyl group, a 3-carbamoylcyclobutyl group, a 2-carbamoylcyclobutyl group, a 2-carbamoylcyclopentyl group, a 3-carbamoylcyclopentyl group, a 2-carbamoylcyclohexyl group, a 3-carbamoylcyclohexyl group, a 4-carbamoylcyclohexyl group, a 2-carbamoylcycloheptyl group, a 3-carbamoylcycloheptyl group, a 4-carbamoylcycloheptyl group, a 2-carbamoylcyclooctyl group, a 3-carbamoylcyclooctyl group, a 4-carbamoylcyclooctyl group, a 5-carbamoylcyclooctyl group.

"Cycloalkyl group substituted with a trifluoromethyl group" represented by R includes more concretely, for example, a 2-(trifluoromethyl)cyclopropyl group, a 2-(trifluoromethyl)cyclobutyl group, a 3-(trifluoromethyl)cyclobutyl group, a 2-(trifluoromethyl)cyclopentyl group, a 3-(trifluoromethyl)cyclopentyl group, a 2-(trifluoromethyl)cyclohexyl group, a 3-(trifluoromethyl)cyclohexyl group, a 4-(trifluoromethyl)cyclohexyl group, a 2-(trifluoromethyl)cycloheptyl group, a 3-(trifluoromethyl)cycloheptyl group, a 4-(trifluoromethyl)cycloheptyl group, a 2-(trifluoromethyl)cyclooctyl group, a 3-(trifluoromethyl)cyclooctyl group, a 4-(trifluoromethyl)cyclooctyl group, a 5-(trifluoromethyl)cyclooctyl group.

"Cycloalkyl group substituted with a lower alkylsulfonyl group" represented by R includes more concretely, for example, a 2-methanesulfonylcyclopropyl group, a 2-methanesulfonylcyclobutyl group, a 3-methanesulfonylcyclobutyl group, a 2-methanesulfonylcyclopentyl group, a 3-methanesulfonylcyclopentyl group, a 2-methanesulfonylcyclohexyl group, a 3-methanesulfonylcyclohexyl group, a 4-methanesulfonylcyclohexyl group, a 2-methanesulfonylcycloheptyl group, a 3-methanesulfonylcycloheptyl group, a 4-methanesulfonylcycloheptyl group, a 2-methanesulfonylcyclooctyl group, a 3-methanesulfonylcyclooctyl group, a 4-methanesulfonylcyclooctyl group, a 5-methanesulfonylcyclooctyl group.

"Cycloalkyl group substituted with a cyclo-lower alkylsulfonyl group" represented by R includes more concretely, for example, a 2-cyclopropanesulfonylcyclopropyl group, a 2-cyclopropanesulfonylcyclobutyl group, a 3-cyclopropanesulfonylcyclobutyl group, a 2-cyclopropanesulfonylcyclopentyl group, a 3-cyclopropanesulfonylcyclopentyl group, a 2-cyclopropanesulfonylcyclohexyl group, a 3-cyclopropanesulfonylcyclohexyl group, a 4-cyclopropanesulfonylcyclohexyl group, a 2-cyclopropanesulfonylcycloheptyl group, a 3-cyclopropanesulfonylcycloheptyl group, a 4-cyclopropanesulfonylcycloheptyl group, a 2-cyclopropanesulfonylcyclooctyl group, a 3-cyclopropanesulfonylcyclooctyl group, a 4-cyclopropanesulfonylcyclooctyl group, a 5-cyclopropanesulfonylcyclooctyl group.

"Aralkyl group" for R is described.

"Aralkyl group" represented by R in formula (II) means an alkyl group such as that mentioned above but having a hydrocarbon-cyclic aryl group with from 6 to 14 carbon atoms such as a phenyl group, a naphthyl group or a biphenyl group, and it includes, for example, a benzyl group, a 2-phenylethyl group, a 1-phenylethyl group, a 1-naphthylmethyl group, a 2-naphthylmethyl group, a 1-naphthalene-1-ethyl group, a 1-naphthalen-2-ylethyl group. Of those, preferred are a benzyl group, a 2-phenylethyl group, a 1-phenylethyl group, a 1-naphthylmethyl group and a 2-naphthylmethyl group; and more preferred are a benzyl group, a 2-phenylethyl group, a 1-phenylethyl group and a 1-naphthylmethyl group.

When R is an "aralkyl group", then the substituent that the aralkyl group may have is preferably a cyano group, a hydroxyl group, a lower alkoxy group (the lower alkoxy group may be substituted with a halogen atom), a halogen atom, a di-lower alkylaminocarbonyloxy group, a di-lower alkylcarbamoyl group or a trifluoromethyl group of the substituents mentioned above, and more preferably a cyano group, a hydroxyl group, a lower alkoxy group (the lower alkoxy group may be substituted with a halogen atom), a halogen atom or a trifluoromethyl group.

The aralkyl group may have one or two and the same or different groups of these substituents at any bondable position.

"Aralkyl group substituted with a cyano group" represented by R includes more concretely, for example, a 4-cyanobenzyl group, a 1-(4-cyanophenyl)ethyl group, a 2-(4-cyanophenyl)ethyl group.

"Aralkyl group substituted with a hydroxyl group" represented by R includes more concretely, for example, a 4-hydroxybenzyl group, a 1-(4-hydroxyphenyl)ethyl group, a 2-(4-hydroxyphenyl)ethyl group.

"Aralkyl group substituted with an alkoxy group (the alkoxy group may be substituted with a halogen atom" represented by R includes more concretely, for example, a 2-methoxybenzyl group, a 3-methoxybenzyl group, a 4-methoxybenzyl group, a 2-chloromethoxybenzyl group, a 2-(4-methoxyphenyl)ethyl group, a 2-(3-methoxyphenyl)ethyl group, a 2-(2-methoxyphenyl)ethyl group, a 1-(4-methoxyphenyl)ethyl group, a 1-(3-methoxyphenyl)ethyl group, a 1-(2-methoxyphenyl)ethyl group.

"Aralkyl group substituted with halogen atom" represented by R includes more concretely, for example, a 4-chlorobenzyl group, a 1-(4-chlorophenyl)ethyl group, a 2-(4-chlorophenyl)ethyl group.

"Aralkyl group substituted with an alkylaminocarbonyloxy group" represented by R includes more concretely, for example, a 4-(methylcarbamoyloxy)benzyl group, a 4-(ethylcarbamoyloxy)benzyl group, a 4-(methylcarbamoyloxy)benzyl group, a 4-(cyclopropylcarbamoyloxy)benzyl group.

"Aralkyl group substituted with a dialkylaminocarbonyloxy group" represented by R includes more concretely, for example, a 4-(dimethylaminocarbonyloxy)benzyl group, a 4-(ethylmethylcarbamoyloxy)benzyl group, a 4-(diethylcarbamoyloxy)benzyl group.

"Aralkyl group substituted with a dialkylcarbamoyl group" represented by R includes more concretely, for example, a 4-dimethylcarbamoylbenzyl group, a 4-(ethylmethylcarbamoyl)benzyl group, a 2-(3-dimethylcarbamoylphenyl)ethyl group.

"Aralkyl group substituted with an alkylcarbamoyl group" represented by R includes more concretely, for example, a 4-(methylcarbamoyl)benzyl group, a 3-(methylcarbamoyl)benzyl group, a 2-(methylcarbamoyl)benzyl group, a 2-(3-ethylcarbamoylphenyl)ethyl group, a 2-(4-methylcarbamoylphenyl)ethyl group.

"Aralkyl group substituted with a carbamoyl group" represented by R includes more concretely, for example, a 4-carbamoylbenzyl group, a 3-carbamoylbenzyl group, a 2-carbamoylbenzyl group, a 2-(3-carbamoylphenyl)ethyl group, a 2-(4-carbamoylphenyl)ethyl group.

"Aralkyl group substituted with a trifluoromethyl group" represented by R includes more concretely, for example, a 4-(trifluoromethyl)benzyl group, a 3-(trifluoromethyl)benzyl group, a 2-(trifluoromethyl)benzyl group, a 2-(3-trifluoromethylphenyl)ethyl group, a 2-(3-trifluoromethylphenyl)ethyl group, a 2-(4-trifluoromethylphenyl)ethyl group.

"Aralkyl group substituted with a lower alkylsulfonyl group" represented by R includes more concretely, for example, a 4-methanesulfonylbenzyl group, a 3-methanesulfonylbenzyl group, a 2-methanesulfonylbenzyl group, a 4-ethanesulfonylbenzyl group, a 3-ethanesulfonylbenzyl group, a 2-ethanesulfonylbenzyl group, a 2-(3-methanesulfonylphenyl)ethyl group, a 2-(3-methanesulfonylphenyl)ethyl group, 2-(4-methanesulfonylphenyl)ethyl group.

"Aralkyl group substituted with a cyclo-lower alkylsulfonyl group" represented by R includes more concretely, for example, a 4-cyclopropanemethanesulfonylbenzyl group, a 3-cyclopropanemethanesulfonylbenzyl group, a 2-cyclopropanemethanesulfonylbenzyl group, a 2-(3-cyclopropanesulfonylphenyl)ethyl group, a 2-(3-cyclopropanesulfonylphenyl)ethyl group, a 2-(4-cyclopropanesulfonylphenyl)ethyl group.

"3- to 8-membered hetero ring" for R is described below.

"3 to 8-membered heterocyclic ring" represented by R in formula (II) means a 3- to 8-membered hetero ring having 1 or 2 hetero atoms of nitrogen or oxygen atoms in the ring. When the hetero ring has 2 oxygen atoms or nitrogen atoms therein, then the hetero atoms may be the same or different.

The 3- to 8-membered heterocyclic group includes, for example, an oxetanyl group, a tetrahydrofuranyl group, a tetrahydropyranyl group, an azetidinyl group, a pyrrolidinyl group, a piperidinyl group, a homopiperidinyl group, a morpholinyl group, a homomorpholinyl group, a piperazinyl group, a homopiperazinyl group. Of those, preferred are an oxetanyl group, a tetrahydrofuranyl group, a tetrahydropyranyl group, a pyrrolidinyl group, a piperidinyl group, a homopiperidinyl group, a morpholinyl group, a homomorpholinyl group; and more preferred are an oxetanyl group, a tetrahydrofuranyl group, a tetrahydropyranyl group, a piperidinyl group, a homopiperidinyl group.

When R is a "3- to 8-membered hetero ring", then the substituent that the hetero ring may have is preferably a cyano group, a hydroxyl group, a lower alkoxy group (the lower alkoxy group may be substituted with a halogen atom), a lower alkyl group (the lower alkoxy group may be substituted with a halogen atom), a halogen atom, a di-lower alkylaminocarbonyloxy group, a di-lower alkylcarbamoyl group or a trifluoromethyl group of the substituents mentioned above, and more preferably a cyano group, a hydroxyl group, a lower alkoxy group (the lower alkoxy group may be substituted with a halogen atom), a lower alkyl group (the lower alkoxy group may be substituted with a halogen atom), a halogen atom or a trifluoromethyl group.

The 3- to 8-membered hetero ring may have one or two and the same or different groups of these substituents at any bondable position.

"3- to 8-membered hetero ring substituted with a cyano group" represented by R includes more concretely, for example, a 4-cyanooxetan-2-yl group, a 4-cyanotetrahydrofuran-3-yl group, a 3-cyanopiperidin-4-yl group, a 6-cyanoazepan-4-yl group.

"3- to 8-membered hetero ring substituted with a lower alkyl group" represented by R includes more concretely, for example, a 2-methyl-oxetan-3-yl group, a 2-chloromethyloxetan-3-yl group, a 4-methyloxetan-2-yl group, a 5-methyltetrahydrofuran-3-yl group, a 5-chloromethyltetrahydrofuran-3-yl group, a 4-methyltetrahydrofuran-2-yl group, a 2-methyltetrahydropyran-4-yl group, a 5-methylpyrrolidin-3-yl group, a 4-methylpyrrolidin-3-yl group, a 2-methylpiperidin-4-yl group, a 3-methylpiperidin-4-yl group, a 7-methylazepan-4-yl group.

"3- to 8-membered hetero ring substituted with a hydroxyl group" represented by R includes more concretely, for example, a 4-hydroxyoxetan-2-yl group, a 4-hydroxytetrahydrofuran-3-yl group, a 3-hydroxypiperidin-4-yl group, a 6-hydroxyazepan-4-yl group.

"3- to 8-membered hetero ring substituted with a halogen atom" represented by R includes more concretely, for example, a 4-fluorooxetan-2-yl group, a 3-fluorooxetan-2-yl group, a 2-fluorooxetan-3-yl group, a 4-fluorotetrahydrofuran-3-yl group, a 3-fluoropiperidin-4-yl group, a 6-fluoroazepan-4-yl group, a 4-fluorooxetan-2-yl group, a 3-fluorooxetan-2-yl group, a 2-chlorooxetan-3-yl group, a 4-chlorotetrahydrofuran-3-yl group, a 3-chloropiperidin-4-yl group, a 6-chloroazepan-4-yl group.

"3- to 8-membered hetero ring substituted with an alkylaminocarbonyloxy group" represented by R includes more concretely, for example, a 4-(methylcarbamoyloxy)oxetan-2-yl group, a 3-(methylcarbamoyloxy)oxetan-2-yl group, a 2-(ethylcarbamoyloxy)oxetan-3-yl group, a 4-(methylcarbamoyloxy)tetrahydrofuran-3-yl group, a 3-(methylcarbamoyloxy)piperidin-4-yl group, a 6-(methylcarbamoyloxy)azepan-4-yl group.

"3- to 8-membered hetero ring substituted with a dialkylaminocarbonyloxy group" represented by R includes more concretely, for example, a 4-(dimethylcarbamoyloxy)oxetan-2-yl group, a 3-(dimethylcarbamoyloxy)oxetan-2-yl group, a 2-(diethylcarbamoyloxy)oxetan-3-yl group, a 4-(ethylcabamoyloxy)tetrahydrofuran-3-yl group, a 3-(dimethylcarbamoyloxy)piperidin-4-yl group, a 6-(dimethylcarbamoyloxy)azepan-4-yl group.

"3- to 8-membered hetero ring substituted with an alkylcarbamoyl group" represented by R includes more concretely, for example, a 4-(methylcarbamoyl)oxetan-2-yl group, a 3-(methylcarbamoyl)oxetan-2-yl group, a 4-(ethylcarbamoyl)tetrahydrofuran-3-yl group, a 3-(methylcarbamoyl)piperidin-4-yl group, a 6-(dimethylcarbamoyl)azepan-4-yl group.

"3- to 8-membered hetero ring substituted with a carbamoyl group" represented by R includes more concretely, for example, a 4-carbamoyloxetan-2-yl group, a 3-carbamoyloxetan-2-yl group, a 4-carbamoyltetrahydrofuran-3-yl group, a 3-carbamoylpiperidin-4-yl group, a 6-carbamoylazepan-4-yl group.

"3- to 8-membered hetero ring substituted with a trifluoromethyl group" represented by R includes more concretely, for example, a 4-(trifluuoromethyl)oxetan-2-yl group, a 3-(trifluoromethyl)oxetan-2-yl group, a 4-(trifluoromethyl)tetrahydrofuran-3-yl group, a 3-(trifluoromethyl)piperidin-4-yl group, a 6-(trifluoromethyl)azepan-4-yl group.

"3- to 8-membered hetero ring substituted with a lower alkylsulfonyl group" represented by R includes more concretely, for example, a 4-(methylsulfonyl)oxetan-2-yl group, a 3-(ethylsulfonyl)oxetan-2-yl group, a 4-(ethylsulfonyl)tetrahydrofuran-3-yl group, a 3-(methylsulfonyl)piperidin-4-yl group, a 6-(methylsulfonyl)azepan-4-yl group.

"3- to 8-membered hetero ring substituted with a cyclo-lower alkylsulfonyl group" represented by R includes more concretely, a 4-(cyclopropylsulfonyl)oxetan-2-yl group, a 3-(cyclopropylsulfonyl)oxetan-2-yl group, a 4-(cyclopropylsulfonyl)tetrahydrofuran-3-yl group, a 3-(cyclopropyl)piperidin-4-yl group, a 6-(cyclopropylsulfonyl)azepan-4-yl group.

When W represents a group of a formula (III):

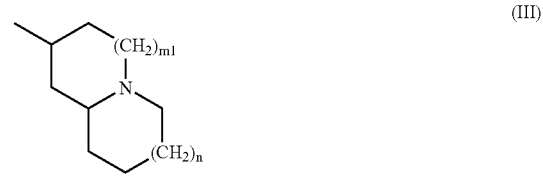

(III)

(wherein the symbols have the same meanings as above), m1 and n are independent of each other, and m indicates an integer of from 0 to 3 and n indicates an integer of from 0 to 2.

Specific examples of the group of formula (III) are the following formula (III-1):

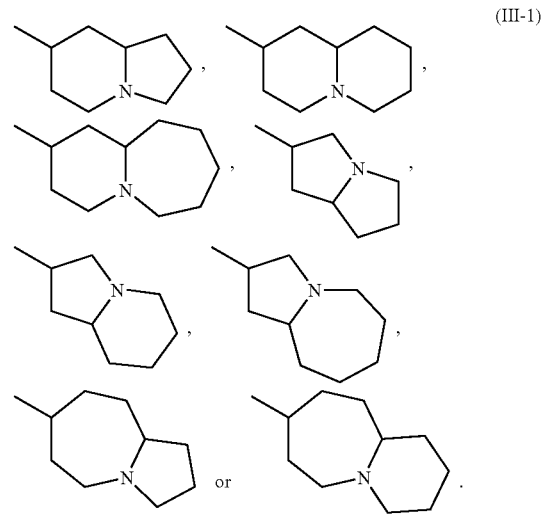

(III-1)

Of those, preferred are the following formula (III-2):

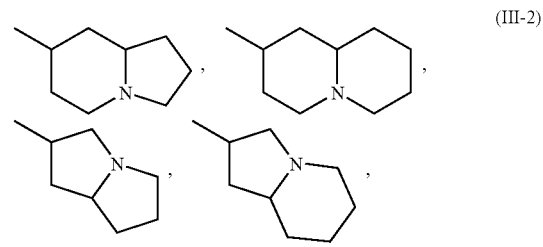

(III-2)

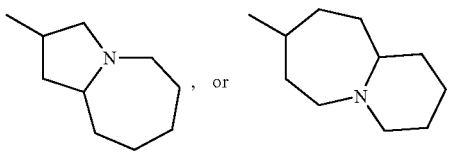

More preferred are the following formula (III-3):

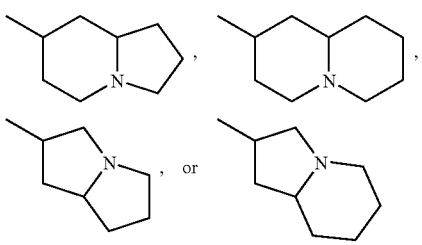

In formula (II) or (III), when m or n in —(CH$_2$)$_m$— and —(CH$_2$)$_n$— is 0, then —(CH$_2$)$_m$— and —(CH$_2$)$_n$— mean a single bond.

Y in formula (I) is described below.
Y means a group of a formula (IV):

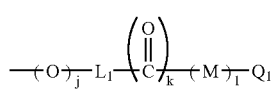

In formula (IV), j, k and l each independently indicate 0 or 1.

When j is 0, then —(O)$_j$— means a single bond.
When k is 0, then —(C(O))$_k$— means a single bond.
When l is 0, then -(M)$_l$- means a single bond.

L$_1$ represents a lower alkyl group having from 1 to 4 carbon atoms, or a single bond. Of those, L$_1$ is preferably a lower alkyl group having from 1 to 3 carbon atoms, or a single bond, more preferably a lower alkyl group having 1 or 2 carbon atoms, or a single bond.

M represents an oxygen atom, or a group of a formula (V):

In formula (V), R$^0$ represents a lower alkyl group having from 1 to 4 carbon atoms. R$^0$ includes, for example, a methyl group, an ethyl group, a propyl group, an n-butyl group, an isopropyl group, an isobutyl group, a tert-butyl group. Of those, preferred are a methyl group, an ethyl group, a propyl group, an n-butyl group, an isopropyl group; and more preferred are a methyl group, an ethyl group, a propyl group, an isopropyl group.

Of the above-mentioned formula (IV), the group of the following formula (IV-1):

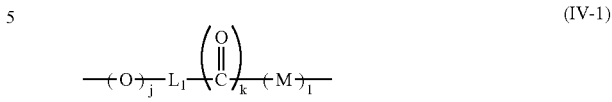

(wherein the symbols have the same meanings as above) is preferably a C$_{1-4}$ lower alkylene group, a carbonyl group, —C(O)—O—, —C$_{1-4}$ lower alkylene-C(O)—, —C$_{1-4}$ lower alkylene-C(O)—O—, —C$_{1-4}$ lower alkylene-C(O)—N(R$^0$)—, —C(O)—N(R$^0$)—, —O—C$_{1-4}$ lower alkylene-, or a single bond, more preferably a C$_{1-4}$ lower alkylene group, —C(O)—O—, —C$_{1-4}$ lower alkylene-C(O)—O—, —C$_{1-4}$ lower alkylene-C(O)—N(R$^0$)—, —C(O)—N(R$^0$)—, —O—C$_{1-4}$ lower alkylene-, or a single bond. In these, R$^0$ has the same meaning as above.

More concretely, the group of formula (IV-1) includes, for example, a methylene group, an ethylene group, a trimethylene group, a tetramethylene group, a carbonyl group, —C(O)—O—, —CH$_2$—C(O)—, —(CH$_2$)$_2$—C(O)—, —CH$_2$—C(O)—O—, —(CH$_2$)$_2$—C(O)—O—, —C(O)—NH—, —C(O)—N(Me)-, —CH$_2$—C(O)—NH—, —CH$_2$—C(O)—N(Me)-, —O—CH$_2$—, —O—(CH$_2$)—, a single bond. Of those, preferred are a methylene group, an ethylene group, a carbonyl group, —C(O)—O—, —CH$_2$—C(O)—, —C(O)—N(Me)-, a single bond.

Q$_1$ is described below.

Q$_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have from 1 to 3 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group, an alkanoyl group, an alkoxycarbonylamino group (the nitrogen atom in the group may be substituted with a lower alkyl group), an alkanoylamino group (the nitrogen atom in the group may be substituted with a lower alkyl group) and an alkylsulfonylamino group (the nitrogen atom in the group may be substituted with a lower alkyl group), or represents a group of a formula (V):

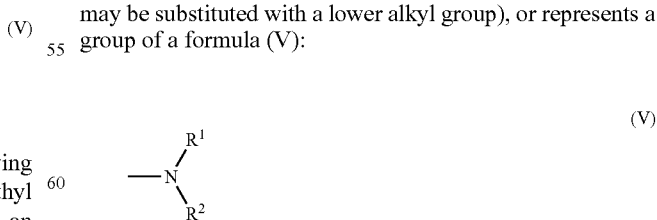

(wherein R$^1$ and R$^2$ are the same or different, each representing a lower alkyl group or a mono- or di-lower alkylcarbamoyl group, or R$^1$ and R$^2$ together form, along with the adjacent nitrogen atom, a 3- to 9-membered lactam ring, a heterocyclic group having from 3 to 8 carbon atoms (the group has 1 or 2 nitrogen atoms or oxygen atoms as the constitutive atoms thereof), a 5-membered heteroaryl group, or a condensed-cyclic heteroaryl group).

"Linear or branched lower alkyl group" represented by $Q_1$ may be the same as the lower alkyl group defined hereinabove. Of those, preferred are a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group; and more preferred are a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a hexyl group, an isohexyl group.

—Y in which $Q_1$ is a "linear or branched lower alkyl group" is more concretely, for example, preferably a methyl group, an ethyl group, a propyl group, an isopropyl group, a butyl group, an isobutyl group, a sec-butyl group, a tert-butyl group, a pentyl group, an isoamyl group, a neopentyl group, a hexyl group, an isohexyl group, a heptyl group, an octyl group, a nonanyl group, a decanyl group, a methoxy group, an ethoxy group, a propoxy group, an isopropoxy group, a butoxy group, a sec-butoxy group, a tert-butoxy group, a pentyloxy group, an isoamyloxy group, a neopentyloxy group, a hexyloxy group, an isohexyloxy group, a heptyloxy group, an octyloxy group, a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isoamyloxycarbonyl group, a neopentyloxycarbonyl group, a hexyloxycarbonyl group, a methoxycarbonylmethoxy group, an ethoxycarbonylmethoxy group, a propoxycarbonylmethoxy group, an isopropoxycarbonylmethoxy group, a butoxycarbonylmethoxy group, an isobutoxycarbonylmethoxy group, a sec-butoxycarbonylmethoxy group, a tert-butoxycarbonylmethoxy group, a pentyloxycarbonylmethoxy group, an isoamyloxycarbonylmethoxy group, a neopentyloxycarbonylmethoxy group, a hexyloxycarbonylmethoxy group, a methoxycarbonylpropoxy group, an ethoxycarbonylpropoxy group, a propoxycarbonylpropoxy group, an isopropoxycarbonylpropoxy group, a butoxycarbonylpropoxy group, an isobutoxycarbonylpropoxy group, a sec-butoxycarbonylpropoxy group, a tert-butoxycarbonylpropoxy group, a pentyloxycarbonylpropoxy group, an isoamyloxycarbonylpropoxy group, a neopentyloxycarbonylpropoxy group, a hexyloxycarbonylpropoxy group; more preferably a an isopropyl group, a butyl group, a isobutyl group, a pentyl group, an isoamyl group, a neopentyl group, a hexyl group, an isohexyl group, a heptyl group, an octyl group, a nonanyl group, a decanyl group, an isopropoxy group, a butoxy group, a sec-butoxy group, a tert-butoxy group, a pentyloxy group, an isoamyloxy group, a neopentyloxy group, a hexyloxy group, an isohexyloxy group, a heptyloxy group, an octyloxy group.

When $Q_1$ is a "linear or branched alkyl group", the substituent which the alkyl group may have is preferably any of a cyano group, a hydroxyl group, a lower alkoxy group (the lower alkoxy group may be substituted with a halogen atom), a halogen atom, a di-lower alkylaminocarbonyloxy group, a di-lower alkylcarbamoyl group and a trifluoromethyl group of the substituents which $Q_1$ may have; more preferably a hydroxyl group, a lower alkoxy group (the lower alkoxy group may be substituted with a halogen atom) or a trifluoromethyl group.

—Y in which $Q_1$ is a "linear or branched lower alkyl group substituted with a cyano group" includes more concretely, for example, a 3-cyanopropyl group, a 4-cyanobutyl group, a 2-cyanobutyl group, a 5-cyanopentyl group, a 4-cyanopentyl group, a 6-cyanohexyl group, a 5-cyanohexyl group, a 4-cyanohexyl group, a 7-cyanoheptyl group, a 6-cyanoheptyl group, a 5-cyanoheptyl group, a 8-cyanooctyl group, a 7-cyanooctyl group, a 6-cyanooctyl group, a 5-cyanooctyl group, a 3-cyanopropoxy group, a 4-cyanobutoxy group, a 3-cyanobutoxy group, a 5-cyanopentyloxy group, a 4-cyanopentyloxy group, a 6-cyanohexyloxy group, a 5-cyanohexyloxy group, a 4-cyanohexyloxy group, a 7-cyanoheptyloxy group, a 6-cyanoheptyloxy group, a 5-cyanoheptyloxy group, a 8-cyanooctyloxy group, a 7-cyanooctyloxy group, a 6-cyanooctyloxy group, a 5-cyanooctyloxy group.

—Y in which $Q_1$ is a "linear or branched lower alkyl group substituted with a hydroxy group" includes more concretely, for example, a 3-hydroxypropyl group, a 4-hydroxybutyl group, a 2-hydroxybutyl group, a 5-hydroxypentyl group, a 4-hydroxypentyl group, a 6-hydroxyhexyl group, a 5-hydroxyhexyl group, a 4-hydroxyhexyl group, a 7-hydroxyheptyl group, a 6-hydroxyheptyl group, a 5-hydroxyheptyl group, a 8-hydroxyoctyl group, a 7-hydroxyoctyl group, a 6-hydroxyoctyl group, a 5-hydroxyoctyl group, a 3-hydroxypropoxy group, a 4-hydroxybutoxy group, a 3-hydroxybutoxy group, a 5-hydroxypentyloxy group, a 4-hydroxypentyloxy group, a 6-hydroxyhexyloxy group, a 5-hydroxyhexyloxy group, a 4-hydroxyhexyloxy group, a 7-hydroxyheptyloxy group, a 6-hydroxyheptyloxy group, a 5-hydroxyheptyloxy group, a 8-hydroxyoctyloxy group, a 7-hydroxyoctyloxy group, a 6-hydroxyoctyloxy group, a 5-hydroxyoctyloxy group.

—Y in which $Q_1$ is a "linear or branched lower alkyl group substituted with a halogen atom" includes more concretely, for example, a 3-fluoropropyl group, a 4-fluorobutyl group, a 2-fluorobutyl group, a 5-fluoropentyl group, a 4-fluoropentyl group, a 6-fluorohexyl group, a 5-fluorohexyl group, a 4-fluorohexyl group, a 7-fluoroheptyl group, a 6-fluoroheptyl group, a 5-fluoroheptyl group, a 8-fluorooctyl group, a 7-fluorooctyl group, a 6-fluorooctyl group, a 5-fluorooctyl group, a 3-fluoropropoxy group, a 4-fluorobutoxy group, a 3-fluorobutoxy group, a 5-fluoropentyloxy group, a 4-fluoropentyloxy group, a 6-fluorohexyloxy group, a 5-fluorohexyloxy group, a 4-fluorohexyloxy group, a 7-fluoroheptyloxy group, a 6-fluoroheptyloxy group, a 5-fluoroheptyloxy group, a 8-fluorooctyloxy group, a 7-fluorooctyloxy group, a 6-fluorooctyloxy group, a 5-fluorooctyloxy group, a 3-chloropropyl group, a 4-chloropropyl group, a 2-chlorobutyl group, a 5-chloropentyl group, a 4-chloropentyl group, a 6-chlorohexyl group, a 5-chlorohexyl group, a 4-chlorohexyl group, a 7-chloroheptyl group, a 6-chloroheptyl group, a 5-chloroheptyl group, a 8-chlorooctyl group, a 7-chlorooctyl group, a 6-chlorooctyl group, a 5-chlorooctyl group, a 3-chloropropoxy group, a 4-chlorobutoxy group, a 3-chlorobutoxy group, a 5-chloropentyloxy group, a 4-chloropentyloxy group, a 6-chlorohexyloxy group, a 5-chlorohexyloxy group, a 4-chlorohexyloxy group, a 7-chloroheptyloxy group a 6-chloroheptyloxy group, a 5-chloroheptyloxy group, a 8-chlorooctyloxy group, a 7-chlorooctyloxy group, a 6-chlorooctyloxy group, a 5-chlorooctyloxy group.

—Y in which $Q_1$ is a "linear or branched lower alkyl group substituted with a mono-lower alkylaminocarbonyloxy group" includes more concretely, for example, a 3-(methylcarbamoyloxy)propyl group, a 4-(methylcarbamoyloxy)butyl group, a 3-(methylcarbamoyloxy)butyl group, a 5-(methylcarbamoyloxy)pentyl group, a 4-(methylcarbamoyloxy) pentyl group, a 6-(methylcarbamoyloxy)hexyl group, a 5-(methylcarbamoyloxy)hexyl group, a 4-(methylcarbamoyloxy)hexyl group, a 7-(methylcarbamoyloxy)heptyl group, a 6-(methylcarbamoyloxy)heptyl group, a 5-(methylcarbamoyloxy)heptyl group, a 8-(methylcarbamoyloxy)octyl group, a 7-(methylcarbamoyloxy)octyl group, a 6-(methylcarbamoyloxy)octyl group, a 5-(methylcarbamoyloxy)octyl group.

—Y of formula (IV) in which $Q_1$ is a "linear or branched lower alkyl group substituted with a di-lower alkylaminocarbonyloxy group" includes more concretely, for example, a 3-(dimethylcarbamoyloxy)propyl group, a 4-(dimethylcarbamoyloxy)butyl group, a 3-(dimethylcarbamoyloxy)butyl group, a 5-(dimethylcarbamoyloxy)pentyl group, a 4-(dimethylcarbamoyloxy)pentyl group, a 6-(dimethylcarbamoyloxy)hexyl group, a 5-(dimethylcarbamoyloxy)hexyl group, a 4-(dimethylcarbamoyloxy)hexyl group, a 2-(dimethylcarbamoyloxy)cycloheptyl group, a 7-(dimethylcarbamoyloxy) heptyl group, a 6-(dimethylcarbamoyloxy)heptyl group, a 8-(dimethylcarbamoyloxy)octyl group, a 7-(dimethylcarbamoyloxy)octyl group, a 6-(dimethylcarbamoyloxy)octyl group, a 5-(dimethylcarbamoyloxy)octyl group.

—Y of formula (IV) in which $Q_1$ is a "linear or branched lower alkyl group substituted with a dialkylcarbamoyl group" includes more concretely, for example, a 3-dimethylcarbamloylpropyl group, a 4-dimethylcarbamoylbutyl group, a 3-dimethylcarbamoylbutyl group, a 5-dimethylcarbamoylpentyl group, a 4-dimethylcabamoylpentyl group, a 6-dimethylcarbamoylhexyl group, a 5-dimethylcarbamoylhexyl group, a 4-dimethylcarbamoylhexyl group, a 7-dimethylcarbamoylheptyl group, a 6-dimethylcarbamoylheptyl group, a 5-dimethylcarbamoylheptyl group, a 8-dimethylcarbamoyloctyl group, a 7-dimethylcarbamoyloctyl group, a 6-dimethylcarbamoyloctyl group, a 5-dimethylcarbamoyloctyl group.

—Y of formula (IV) in which $Q_1$ is a "linear or branched lower alkyl group substituted with a trifluoromethyl group" includes more concretely, for example, a 3-(trifluoromethyl) propyl group, a 4-(trifluoromethyl)butyl group, a 2-(trifluoromethyl)butyl group, a 5-(trifluoromethyl)pentyl group, a 4-(trifluoromethyl)pentyl group, a 6-(trifluoromethyl)hexyl group, a 5-(trifluoromethyl)hexyl group, a 4-(trifluoromethyl)hexyl group, a 7-(trifluoromethyl)heptyl group, a 6-(trifluoromethyl)heptyl group, a 5-(trifluoromethyl)heptyl group, a 8-(trifluoromethyl)octyl group, a 7-(trifluoromethyl)octyl group, a 6-(trifluoromethyl)octyl group, a 5-(trifluoromethyl)octyl group, a 3-(trifluoromethyl)propoxy group, a 4-(trifluoromethyl)butoxy group, a 3-(trifluoromethyl)butoxy group, a 5-(trifluoromethyl)pentyloxy group, a 4-(trifluoromethyl)pentyloxy group, a 6-(trifluoromethyl)hexyloxy group, a 5-(trifluoromethyl)hexyloxy group, a 4-(trifluoromethyl)hexyloxy group, a 7-(trifluoromethyl)heptyloxy group, a 6-(trifluoromethyl)heptyloxy group, a 5-(trifluoromethyl) heptyloxy group, a 8-(trifluoromethyl)octyloxy group, a 7-(trifluoromethyl)octyloxy group, a 6-(trifluoromethyl)octyloxy group, a 5-(trifluoromethyl)octyloxy group.

"Cycloalkyl group having from 3 to 9 carbon atoms" represented by $Q_1$ may be the same as the cycloalkyl group having from 3 to 9 carbon atoms mentioned hereinabove, more concretely including, for example, a cyclopropyl group, a cyclobutyl group, a cyclopentyl group, a cyclohexyl group, a cycloheptyl group, a cyclooctyl group, a cyclopropylmethyl group, a cyclopropylethyl group, a cyclopropylpropyl group, a cylopropylbutyl group, a cyclobutylmethyl group, a cyclobutylethyl group, a cyclobutylpropyl group, a cyclobutylbutyl group, a cyclopentylmethyl group, a cyclopentylethyl group, a cyclopentylpropyl group, a cyclopentylbutyl group, a cyclohexylmethyl group, a cyclohexylethyl group, a cyclohexylpropyl group, a cycloheptylmethyl group, a cycloheptylethyl group, a cycloheptylpropyl group, a cycloheptylbutyl group, a cyclopropylmethoxy group, a cyclopropylethoxy group, a cyclopropylpropoxy group, a cyclopropylbutoxy group, a cyclobutylmethoxy group, a cyclobutylethoxy group, a cyclobutylpropoxy group, a cyclobutylbutoxy group, a cyclopentylmethoxy group, a cyclopentylethoxy group, a cyclopentylpropoxy group, a cyclopentylbutoxy group, a cyclohexylmethoxy group, a cyclohexylethoxy group, a cyclohexylpropoxy group, a cyclohexylbutoxy group. Of those, preferred are a cyclopropyl group, a cyclobutyl group, a cyclopentyl group, a cyclohexyl group, a cycloheptyl group; and more preferred are a cyclopropyl group, a cyclobutyl group, a cyclopentyl group, a cyclohexyl group.

When $Q_1$ is a "cycloalkyl group having from 3 to 9 carbon atoms", the substituent which the cycloalkyl group may have is, for example, preferably any of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group of the substituents which $Q_1$ may have; more preferably a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The cycloalkyl group may have one or two such substituents at the bondable position thereof. When the group has two such substituents, then they may be the same or different.

—Y of formula (IV) in which $Q_1$ is a "cycloalkyl group having from 3 to 9 carbon atoms" substituted with any of these substituents includes more concretely, for example, a 2-fluoropropyl group, a 2-chlorocyclopropyl group, a 2,2-difluorocyclopropyl group, a 2-(methoxycarbonyl)cyclopropyl group, a 2-(ethoxycarbonyl)cyclopropyl group, a 2-(propoxycarbonyl)cyclopropyl group, a 2-(tert-butoxycarbonyl) cyclopropyl group, a 2-(methylcarbamoyl)cyclopropyl group, a 2-(ethylcarbamoyl)cyclopropyl group, a 2-(propylcarbamoyl)cyclopropyl group, a 2-(isopropylcarbamoyl)cyclopropyl group, a 2-(dimethylcarbamoyl)cyclopropyl group, a 2-(diethylcarbamoyl)cyclopropyl group, a 2-(azetidin-1-ylcarbonyl)cyclopropyl group, a 2-(pyrrolidin-1-ylcarbonyl)cyclopropyl group, a 2-(piperidin-1-ylcarbonyl)cyclopropyl group, a 2-(2-oxopyrrolidin-1-yl)cyclopropyl group, a 2-(2-oxopiperidin-1-yl)cyclopropyl group, a cyclopentyl group, a 2-fluorocyclobutyl group, a 2-chlorocyclobutyl group, a 3-fluorocyclobutyl group, a 3-chlorocyclobutyl group, a 3,3-difluorocyclobutyl group, a 3-(methoxycarbonyl)cyclobutyl group, a 3-(ethoxycarbonyl)cyclobutyl group, a 3-(propoxycarbonyl)cyclobutyl group, a 3-(tert-butyloxycarbonyl)cyclobutyl group, a 3-(methylcarbamoyl)cyclobutyl group, a 3-(ethylcarbamoyl)cyclobutyl group, a 3-(propylcarbamoyl)cyclobutyl group, a 3-(isopropylcarbamoyl) cyclobutyl group, a 3-(dimethylcarbamoyl)cyclobutyl group, a 3-(diethylcarbamoyl)cyclobutyl group, a 3-(azetidin-1-yl-carbonyl)cyclobutyl group, a 3-(pyrrolidin-1-ylcarbonyl)cyclobutyl group, a 3-(piperidin-1-ylcarbonyl)cyclobutyl group, a 3-(2-oxopyrrolidin-1-yl)cyclobutyl group, a 3-(2-oxopiperidin-1-yl)cyclobutyl group, a 3-fluorocyclopentyl group, a 3-chlorocyclopentyl group, a 3,3-difluorocyclopentyl group, a 3-(methoxycarbonyl)cyclopentyl group, a 3-(ethoxycarbonyl)cyclopentyl group, a 3-(propoxycarbonyl)cyclopentyl group, a 3-(tert-butoxycarbonyl)cyclopentyl group, a 3-(methylcarbamoyl)cyclopentyl group, a 3-(ethylcarbamoyl)cyclopentyl group, a 3-(propylcarbamoyl)cyclopentyl group, a 3-(isopropylcarbamoyl)cyclopentyl group, a 3-(dimethylcarbamoyl)cyclopentyl group, a 3-(diethylcarbamoyl)cyclopentyl group, a 3-(azetidin-1-ylcarbonyl)cyclopentyl group, a 3-(pyrrolidin-1-ylcarbonyl)cyclopentyl group, a 3-(piperidin-1-ylcarbonyl)cyclopentyl group, a 3-(2-oxopyrrolidin-1-yl)cyclopentyl group, a 3-(2-oxopiperidin-1-yl)cyclopentyl group.

When $Q_1$ is a "phenyl group", the substituent which the phenyl group may have is, for example, preferably any of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group, an alkanoyl group, an alkoxycarbonylamino group (in which the nitrogen atom may be substituted with a lower alkyl group), an alkanoylamino group (in which the nitrogen atom may be substituted with a lower alkyl group) and an alkylsulfonylamino group (in which the nitrogen atom may be substituted with a lower alkyl group) of the substituents which $Q_1$ may have; more preferably a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The phenyl group may have one or two such substituents at the bondable position thereof.

—Y of formula (IV) in which $Q_1$ is a phenyl group that may be substituted with any of these substituents includes more concretely, for example, a phenyl group, a 4-cyanophenyl group, a 3-cyanophenyl group, a 2-cyanophenyl group, a 4-methoxyphenyl group, a 3-methoxyphenyl group, a 2-methoxyphenyl group, a 4-(dimethylcarbamoyl)phenyl group, a 3-(dimethylcarbamoyl)phenyl group, a 2-(dimethylcarbamoyl)phenyl group, a 4-(methylcarbamoyl)phenyl group, a 3-(methylcarbamoyl)phenyl group, a 2-(methylcarbamoyl)phenyl group, a 4-carbamoylphenyl group, a 3-carbamoylphenyl group, a 2-carbamoylphenyl group, a 4-(cyclopropylcarbamoyl)phenyl group, a 3-(cyclopropylcarbamoyl)phenyl group, a 2-(cyclopropylcarbamoyl)phenyl group, a 4-(pyrrolidine-1-carbonyl)phenyl group, a 3-(pyrrolidine-1-carbonyl)phenyl group, a 2-(pyrrolidine-1-carbonyl)phenyl group, a 4-(piperidine-1-carbonyl)phenyl group, a 3-(piperidine-1-carbonyl)phenyl group, a 2-(piperidine-1-carbonyl)phenyl group, a 4-(morpholine-1-carbonyl)phenyl group, a 3-(morpholine-1-carbonyl)phenyl group, a 2-(morpholine-1-carbonyl)phenyl group, a 4-chlorophenyl group, a 3-chlorophenyl group, a 2-chlorophenyl group, a 4-hydroxyphenyl group, a 3-hydoxyphenyl group, a 2-hydroxyphenyl group, a 4-methylphenyl group, a 3-methylphenyl group, a 2-methylphenyl group, a 4-(trifluoromethyl)phenyl group, a 3-(trifluoromethyl)phenyl group, a 2-(trifluoromethyl)phenyl group, a 4-(2-oxo-2H-pyridin-1-yl)phenyl group, a 4-(3-oxomorphlin-4-yl)phenyl group, a 4-(2-oxo-oxazolidin-1-yl)phenyl group, 4-tert-butylphenyl group, a 3-tert-butylphenyl group, a 2-tert-butylphenyl group, a 4-(trifluoromethoxy)phenyl group, a 3-(trifluoromethoxy)phenyl group, a 2-(trifluoromethyl)phenyl group, a 4-(difluoromethoxy)phenyl group, a 3-(difluoromethoxy)phenyl group, a 4-hydroxyphenyl group, a 3-hydroxyphenyl group, a 2-hydroxyphenyl group, a 4-(2-hydroxypropan-2-yl)phenylmethyl group, a 3-(2-hydroxypropan-2-yl)phenylmethyl group, a 4-(methylamino)phenyl group, a 3-(methylamino)phenyl group, a 2-(methylamino)phenyl group, a 4-(dimethylamino)phenyl group, a 3-(dimethylamino)phenyl group, a 2-(dimethylamino)phenyl group, a 4-acetylphenyl group, a 3-acetylphenyl group, a 2-acetylphenyl group, a 4-methanesulfonylphenyl group, a 3-methanesulfonylphenyl group, a 2-methanesulfonylphenyl group, a 4-(acetylamino)phenyl group, a 3-(acetylamino)phenyl group, a 2-(acetylamino)phenyl group, a 4-(N-acetyl-N-methylamino)phenyl group, a 3-(N-acetyl-N-methylamino)phenyl group, a 4-cyano-3-fluorophenyl group, a 4-(methoxycarbonylamino)phenyl group, a 3-(methoxycarbonylamino)phenyl group, a 2-(methoxycarbonylamino)phenyl group, a 4-(ethoxycarbonylamino)phenyl group, a 3-(ethoxycarbonylamino)phenyl group, a 2-(ethoxycarbonylamino)phenyl group, a 4-(propoxycarbonylamino)phenyl group, a 3-(propoxycarbonylamino)phenyl group, a 2-(propoxycarbonylamino)phenyl group, a 4-(isopropoxycarbonylamino)phenyl group, a 3-(isopropoxycarbonylamino)phenyl group, a 2-(isopropoxycarbonylamino)phenyl group, a 4-{(N-methyl)methoxycarbonylamino}phenyl group, a 3-{(N-methyl)methoxycarbonylamino}phenyl group, a 2-{(methyl)methoxycarbonylamino}phenyl group, a 4-{(N-methyl)ethoxycarbonylamino}phenyl group, a 3-{(N-methyl)ethoxycarbonylamino}phenyl group, a 2-{(N-methyl)ethoxycarbonylamino}phenyl group, a 4-{(methyl)ethoxycarbonylamino}phenyl group, a 3-{(N-methyl)ethoxycarbonylamino}phenyl group, a 2-{(N-methyl)ethoxycarbonylamino}phenyl group, a 4-{(N-methyl)propoxycarbonylamino}phenyl group, a 3-{(N-methyl)propoxycarbonylamino}phenyl group, a 2-{(N-methyl)propoxycarbonylamino}phenyl group, a 4-{(N-methyl)methoxycarbonylamino}phenyl group, a 3-{(N-methyl)methoxycarbonylamino}phenyl group, a 2-{(N-methyl)methoxycarbonylamino}phenyl group, a 4-{(N-methyl)isopropoxycarbonylamino}phenyl group, a 3-{(N-methyl)isopropoxycarbonylamino}phenyl group, a 2-{(N-methyl)isopropoxycarbonylamino}phenyl group, a 4-{(N-ethyl)methoxycarbonylamino}phenyl group, a 3-{(N-ethyl)methoxycarbonylamino}phenyl group, a 2-{(N-ethyl)methoxycarbonylamino}phenyl group, a 4-(acetylamino)phenyl group, a 3-(acetylamino)phenyl group, a 2-(acetylamino)phenyl group, a 4-(propanoylamino)phenyl group, a 3-(propanoylamino)phenyl group, a 2-(propanoylamino)phenyl group, a 4-{(N-methyl)acetylamino}phenyl group, a 3-{(N-methyl)acetylamino}phenyl group, a 2-{(N-methyl)acetylamino}phenyl group, a 4-{(N-ethyl)propanoylamino}phenyl group, a 3-{(N-methyl)propanoylamino}phenyl group, a 2-{(methyl)propanoylamino}phenyl group, a 4-{(N-ethyl)propanoylamino}phenyl group, a 3-{(N-ethyl)acetylamino}phenyl group, a 2-{(N-ethyl)

acetylamino}phenyl group, a 4-{(M-ethyl)propanoylamino}phenyl group, a 3-{(N-ethyl)propanoylamino}phenyl group, a 2-{(N-ethyl)propanoylamino}phenyl group, a 4-(methylsulfonylamino)phenyl group, a 3-(methylsulfonylamino)phenyl group, a 2-(methylsulfonylamino)phenyl group, a 4-(ethylsulfonylamino)phenyl group, a 3-(ethylsulfonylamino)phenyl group, a 2-(ethylsulfonylamino)phenyl group, a 4-(propylsulfonylamino)phenyl group, a 3-(propylsulfonylamino)phenyl group, a 2-(propylsulfonylamino)phenyl group, a 4-(isopropylsulfonylamino)phenyl group, a 3-(isopropylsulfonylamino)phenyl group, a 2-(isopropylsulfonylamino)phenyl group, a 4-{(N-methyl)methylsulfonylamino}phenyl group, a 3-{(N-methyl)methylsulfonylamino}phenyl group, a 2-{(N-methyl)methylsulfonylamino}phenyl group, a 4-{(N-methyl)ethylsulfonylamino}phenyl group, a 3-{(N-methyl)ethylsulfonylamino}phenyl group, a 2-{(N-methyl)ethylsulfonylamino}phenyl group, a 4-{(N-ethyl)methylsulfonylamino}phenyl group, a 3-{(N-ethyl)methylsulfonylamino}phenyl group, a 2-{(N-ethyl)methylsuflonylamino}phenyl group, a 4-{(N-ethyl)ethylsulfonylamino}phenyl group a 3-{(N-ethyl)ethylsulfonylamino}phenyl group, a 2-{(N-ethyl)ethylsulfonylamino}phenyl group, a 4-{(N-ethyl)propylsulfonylamino}phenyl group, a 3-{(N-ethyl)propylsulfonylamino}phenyl group, a 2-{(N-ethyl)propylsulfonylamino}phenyl group, a 4-(2-oxazolidin-3-yl)phenyl group, a 3-(2-oxazolidin-3-yl)phenyl group, a 2-(oxazolidin-3-yl)phenyl group, a phenylmethyl group, a 4-cyanophenylmethyl group, a 3-cyanophenylmethyl group, a 4-dimethylcarbamoylphenylmethyl group, a 3-dimethylcarbamoylphenylmethyl group, a 2-dimethylcarbamoylphenylmethyl group, a 4-methylcarbamoylphenylmethyl group, a 3-methylcarbamoylphenylmethyl group, a 2-methylcarbamoylphenylmethyl group, a 4-cyclopropylcarbamoylphenylmethyl group, a 3-cyclopropylcarbamoylphenylmethyl group, a 2-cyclopropylcarbamoylphenylmethyl group, a 4-(pyrrolidine-1-carbonyl)phenylmethyl group, a 3-(pyrrolidine-1-carbonyl)phenylmethyl group, a 2-(pyrrolidine-1-carbonyl)phenylmethyl group, a 4-(piperidine-1-carbonyl)phenylmethyl group, a 3-(piperidine-1-carbonyl)phenylmethyl group, a 2-(piperidine-1-carbonyl)phenylmethyl group, a 4-(morpholine-1-carbonyl)phenylmethyl group, a 3-(morpholine-1-carbonyl)phenylmethyl group, a 2-(morpholine-1-carbonyl)phenylmethyl group, a 4-chlorophenylmethyl group, a 3-chlorophenylmethyl group, a 2-chlorophenylmethyl group, a 4-hydroxyphenylmethyl group, a 3-hydroxyphenylmethyl group, a 2-hydroxyphenylmethyl group, a 4-methylphenylmethyl group, a 3-methylphenylmethyl group, a 2-methylphenylmethyl group, a 4-(trifluoromethyl)phenylmethyl group, a 3-(trifluoromethyl)phenylmethyl group, a 2-(trifluoromethyl)phenylmethyl group, a 4-(2-oxo-2H-pyridin-1-yl)phenylmethyl group, a 4-(3-oxomorpholin-4-yl)phenylmethyl group, a 4-(2-oxo-oxazolidin-3-yl)phenylmethyl group, a 4-tert-butylphenylmethyl group, a 3-tert-butylphenylmethyl group, a 2-tert-butylphenylmethyl group, a 4-(trifluoromethoxy)phenylmethyl group, a 3-(trifluoromethoxy)phenylmethyl group, a 2-(trifluoromethyl)phenylmethyl group, a 4-(difluoromethoxy)phenylmethyl group, a 3-(difluoromethoxy)phenylmethyl group, a 4-hydroxyphenylmethyl group, a 3-hydroxyphenylmethyl group, a 2-hydroxyphenylmethyl group, a 4-(2-hydroxypropan-2-yl)phenylmethyl group, a 3-(2-hydroxypropan-2-yl)phenylmethyl group, a 4-(methylamino)phenylmethyl group, a 3-(methylamino)phenylmethyl group, a 2-(methylamino)phenylmethyl group, a 4-(dimethylamino)phenylmethyl group, a 3-(dimethylamino)phenylmethyl group, a 2-(dimethylamino)phenylmethyl group, a 4-(N-acetyl-N-methylamino)phenylmethyl group, a 3-(N-acetyl-N-methylamino)phenylmethyl group, a 4-cyano-3-fluorophenylmethyl group, a 2-phenylethyl group, a 2-(2-dimethylcarbamoylphenyl)ethyl group, a 2-(4-methylcarbamoylphenyl)ethyl group, a 2-(3-methylcarbamoylphenyl)ethyl group, a 2-(2-methylcarbamoylphenyl)ethyl group, a 2-(4-cyclopropylcarbamoylphenyl)ethyl group, a 2-(3-cyclopropylcarbamoylphenyl)ethyl group, a 2-(2-cyclopropylcarbamoylphenyl)ethyl group, a 2-{4-(pyrrolidine-1-carbonyl)phenyl}ethyl group, a 2-{3-(pyrrolidine-1-carbonyl)phenyl}ethyl group, a 2-{2-(pyrrolidine-1-carbonyl)phenyl}ethyl group, a 2-{4-(piperidine-1-carbonyl)phenyl}ethyl group, a 2-{3-piperidine-1-carbonyl)phenyl}ethyl group, a 2-{2-(piperidine-1-carbonyl)phenyl}ethyl group, a 2-{4-(morpholine-1-carbonyl)phenyl}ethyl group, a 2-{3-(morpholine-1-carbonyl)phenyl}ethyl group, a 2-{2-(morpholine-1-carbonyl)phenyl}ethyl group, a 2-(4-chlorophenyl)ethyl group, a 2-(3-chlorophenyl)ethyl group, a 2-(2-chlorophenyl)ethyl group, a 2-(4-hydroxyphenyl)ethyl group, a 2-(3-hydroxyphenyl)ethyl group, a 2-(2-hydroxyphenyl)ethyl group, a 2-(4-methylphenyl)ethyl group, a 2-(3-methylphenyl)ethyl group, a 2-(2-methylphenyl)ethyl group, a 2-{4-(trifluoromethyl)phenyl}ethyl group, a 2-{3-(trifluoromethyl)phenyl}ethyl group, a 2-{2-(trifluoromethyl)phenyl}ethyl group, a 2-{4-(2-oxo-2H-pyridin-1-yl)phenyl}ethyl group, a 2-{4-(3-oxomorpholin-4-yl)phenyl}ethyl group, a 2-{4-(2-oxo-oxazolidin-3-yl)phenyl}ethyl group, a 2-(4-tert-butylphenyl)ethyl group, a 2-(3-tert-butylphenyl)ethyl group, a 2-(2-tert-butylphenyl)ethyl group, a 2-{4-(trifluoromethoxy)phenyl}ethyl group, a 2-{3-(trifluoromethoxy)phenyl}ethyl group, a 2-{2-(trifluoromethyl)phenyl}ethyl group, a 2-{4-(difluoromethoxy)phenyl}ethyl group, a 2-{3-(difluoromethoxy)phenyl}ethyl group, a 2-(4-hydroxyphenyl)ethyl group, a 2-(3-hydroxyphenyl)ethyl group, a 2-(2-hydroxyphenyl)ethyl group, a 2-{4-(2-hydroxypropan-2-yl)phenyl}ethyl group, a 2-{3-(2-hydroxypropan-2-yl)phenyl}ethyl group, a 2-{4-(methylamino)phenyl}ethyl group, a 2-{3-(methylamino)phenyl}ethyl group, a 2-{2-(methylamino)phenyl}ethyl group, a 2-{4-(dimethylamino)phenyl}ethyl group, a 2-{3-(dimethylamino)phenyl}ethyl group, a 2-{2-(dimethylamino)phenyl}ethyl group, a 2-(4-acetylphenyl)ethyl group, a 2-(3-acetylphenyl)ethyl group, a 2-(2-acetylphenyl)ethyl group, a 2-(4-methanesulfonylphenyl)ethyl group, a 2-(3-methanesulfonylphenyl)ethyl group, a 2-(2-methanesulfonylphenyl)ethyl group, a 2-{4-(acetylamino)phenyl}ethyl group, a 2-{3-(acetylamino)phenyl}ethyl group, a 2-{2-(acetylamino)phenyl}ethyl group, a 4-(N-acetyl-N-methylamino)phenylmethyl group, a 2-{3-(N-acetyl-N-methylamino)phenyl}ethyl group, a 2-(4-cyano-3-fluorophenyl)ethyl group, a phenoxymethyl group, a 4-cyanophenoxymethyl group, a 3-cyanophenoxymethyl group, a 4-dimethylcarbamoylphenoxymethyl group, a 3-dimethylcarbamoylphenoxymethyl group, a 2-dimethylcarbamoylphenoxymethyl group, a 4-methylcarbamoylphenoxymethyl group, a 3-methylcarbamoylphenoxy group, a 2-methylcarbamoylphenoxymethyl group, a 4-cyclopropylcarbamoylphenoxymethyl group, a 3-cyclopropylcarbamoylphenoxymethyl group, a 2-cyclopropylcarbamoylphenoxymethyl group, a 4-(pyrrolidine-1-carbonyl)phenoxymethyl group, a 3-(pyrrolidine-1-carbonyl)

phenoxymethyl group, a 2-(pyrrolidine-1-carbonyl)phenoxymethyl group, a 4-(piperidine-1-carbonyl)phenoxymethyl group, a 3-(piperidine-1-carbonyl)phenoxymethyl group, a 2-(piperidine-1-carbonyl)phenoxymethyl group, a 4-(morpholine-1-carbonyl)phenoxymethyl group, a 3-(morpholine-1-carbonyl)phenoxymethyl group, a 2-(morpholine-1-carbonyl)phenoxymethyl group, a 4-chloro-phenoxymethyl group, a 3-chlorophenoxymethyl group, a 2-chlorophenoxymethyl group, a 4-hydroxyphenylmethyl group, a 3-hydroxyphenylmethyl group, a 2-hydroxyphenoxymethyl group, a 4-methylphenoxymethyl group, a 3-methylphenoxymethyl group, a 2-methylphenoxymethyl group, a 4-(trifluuoromethyl)phenoxymethyl group, a 3-(trifluuoromethyl)phenoxymethyl group, a 2-(trifluoromethyl)phenoxymethyl group, a 4-(2-oxo-2H-pyridin-1-yl)phenoxymethyl group, a 4-(3-oxomorpholin-4-yl)phenoxymethyl group, a 4-(2-oxo-oxazolidin-3-yl)phenoxymethyl group, a 4-tert-butylphenoxymethyl group, a 3-tert-butylphenoxymethyl group, a 2-tert-butylphenoxymethyl group, a 4-(trifluoromethoxy)phenoxymethyl group, a 3-(trifluoromethoxy)phenoxymethyl group a 2-(trifluoromethyl)phenoxymethyl group, a 4-(difluoromethoxy)phenoxymethyl group, a 3-(difluoromethoxy)phenoxymethyl group, a 4-hydroxyphenoxymethyl group, a 3-hydroxyphenoxymethyl group, a 2-hydroxyphenoxymethyl group, a 4-(2-hydroxypropan-2-yl)phenoxymethyl group, a 3-(2-hydroxypropan-2-yl)phenoxymethyl group, a 4-(methylamino)phenoxymethyl group, a 3-(methylamino)phenoxymethyl group, a 2-(methylamino)phenoxymethyl group, a 4-(dimethylamino)phenoxymethyl group, a 3-(dimethylamino)phenoxymethyl group, a 2-(dimethylamino)phenoxymethyl group, a 4-acetylphenylmethyl group, a 3-acetylphenylmethyl group, a 2-acetylphenoxymethyl group, a 4-methanesulfonylphenoxymethyl group, a 3-methanesulfonylphenoxymethyl group, a 2-methanesulfonylphenoxymethyl group, a 4-(acetylamino)phenoxymethyl group, a 3-(acetylamino)phenoxymethyl group, a 2-(acetylamino)phenoxymethyl group, a 4-(N-acetyl-N-methylamino)phenoxymethyl group, a 2-(N-acetyl-N-methylamino)phenoxymethyl group, a 4-cyano-3-fluorophenoxymethyl group.

"5- or 6-membered heteroaryl group" represented by $Q_1$ means a 5- or 6-membered monocyclic group having from 1 to 3 hetero atoms in the ring, selected from a group consisting of a nitrogen atom, a sulfur atom and an oxygen atom, including, for example, a furyl group, a thienyl group, a pyrrolyl group, an imidazolyl group, a pyrazolyl group, a thiazolyl group, a thiadiazolyl group, an isothiazolyl group, an oxazolyl group, an isoxazolyl group, a pyridyl group, a pyrimidinyl group, a pyrazinyl group. Of those, preferred are a furyl group, a thienyl group, a pyrrolyl group, a pyrazolyl group, a thiazolyl group, a thiadiazolyl group, an isothiazolyl group, an oxazolyl group, an isoxazolyl group, a pyridyl group, a pyrimidinyl group, a pyrazyl group; and more preferred are a pyrazolyl group, a thiazolyl group, a thiadiazolyl group, an isothiazolyl group, an oxazolyl group, an isoxazolyl group, a pyridyl group, a pyrimidinyl group, a pyrazinyl group.

When $Q_1$ is a "5- or 6-membered heteroaryl group", the substituent which the heteroaryl group may have is, for example, preferably any of a cyano group, a hydroxyl group, a lower alkyl group (the lower alkyl group may be substituted with a hydroxyl group, a halogen atom or an amino group), a lower alkyl group, a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group of the substituents which $Q_1$ may have; more preferably a hydroxyl group, a lower alkyl group (the lower alkyl group may be substituted with a hydroxyl group, a halogen atom or an amino group), a lower alkyl group, a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The heteroaryl group may have one or two such substituents at the bondable position thereof.

—Y of formula (IV) in which $Q_1$ is a "5- or 6-membered heteroaryl group" that may be substituted with any of these substituents includes more concretely, for example, a furyl group, a thienyl group, a pyrrolyl group, an imidazolyl group, a pyrazolyl group, a thiazolyl group, a thiadiazolyl group, an isothiazolyl group, an oxazolyl group, an isoxazolyl group, a pyridyl group, a pyrimidinyl group, a pyrazinyl group, a 6-(pyrrolidine-1-carbonyl)pyridin-3-yl group, a 5-(pyrrolidine-1-carbonyl)pyridin-2-yl group, a 6-(piperidine-1-carbonyl)pyridin-3-yl group, a 5-(piperidine-1-carbonyl)pyridin-2-yl group, a 5-(piperidine-1-carbonyl)pyridin-2-yl group, a 6-methylpyridin-3-yl group, a 5-methylpyridin-2-yl group, a 6-ethylpyridin-3-yl group, a 5-ethylpyridin-2-yl group, a 6-isopropylpyridin-3-yl group, a 5-isopropylpyridin-2-yl group, a 6-cyclopropylpyridin-3-yl group, a 5-cyclopropylpyridin-2-yl group, a 6-fluoropyridin-3-yl group, a 5-fluoropyridin-2-yl group, a 6-(cyclopentyloxy)pyridin-3-yl group, a 5-(cyclopentyloxy)pyridin-2-yl group, a 6-(trifluoromethoxy)pyridin-3-yl group, a 5-(trifluoromethoxy)pyridin-2-yl group, a 6-(difluoromethoxy)pyridin-3-yl group, a 5-(difluoromethoxy)pyridin-2-yl group, a 2-cyanopyridin-5-yl group, a 5-cyanothiophen-2-yl group, a 3-methyl-[1,2,4]oxadiazol-5-yl group.

"Heterocyclic group having from 3 to 8 carbon atoms" for $Q_1$ is described below.

"Heterocyclic group having from 3 to 8 carbon atoms" represented by $Q_1$ means a 3- to 8-membered monocyclic group having 1 or 2 nitrogen atoms or oxygen atoms in the ring. The heterocyclic group may be the same as the heterocyclic group having from 3 to 8 carbon atoms represented by R which $Q_1$ may have, or it may be a group of the following formula ($Q_1$-1):

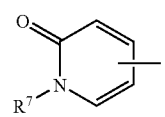

($Q_1$-1)

[wherein $R^7$ represents a hydrogen atom, a lower alkyl group, a cyclo-lower alkyl group, a halo-lower alkyl group, or an aralkyl group].

When $Q_1$ is a "heterocyclic group having from 3 to 8 carbon atoms", the substituent which the heterocyclic group may have is, for example, preferably any of a cyano group, a hydroxyl group, a lower alkyl group (the lower alkyl group may be substituted with a hydroxyl group, a halogen atom or an amino group), a cyclo-lower alkyl group, a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group of the substituents which $Q_1$ may have; more preferably a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The heterocyclic group may have one or two such substituents at the bondable position thereof.

—Y of formula (IV) in which $Q_1$ is a "heterocyclic group having from 3 to 8 carbon atoms" that may be substituted with any of these substituents includes more concretely, for example, a 1H-pyridin-2-on-4-yl group, a 1H-pyridin-2-on-4-yl group, a 1-methyl-1H-pyridin-2-on-4-yl group, a 1-ethyl-1H-pyridin-2-on-4-yl group, a 1-isopropyl-1H-pyridin-2-on-4-yl group, a 1-difluoromethyl-1H-pyridin-2-on-4-yl group, a 1-(2-fluoroethyl)-1H-pyridin-2-on-4-yl group, a 1-(2,2-difluoroethyl)-1H-pyridin-2-on-4-yl group, a 1-(2,2,2-trifluoroethyl)-1H-pyridin-2-on-4-yl group, a 1-(2-fluoroethoxy)-1H-pyridin-2-on-4-yl group, a 1-cyclopropyl-1H-pyridin-2-on-4-yl group, a 1-cyclobutyl-1H-pyridin-2-on-4-yl group, a 1-cyclopentyl-1H-pyridin-2-on-4-yl group, a 1-methyl-1H-pyridin-2-on-5-yl group, a 1-ethyl-1H-pyridin-2-on-5-yl group, a 1-ethyl-1H-pyridin-2-on-5-yl group, a 1-isopropyl-1H-pyridin-2-on-5-yl group, a 1-(2-fluoroethyl)-1H-pyridin-2-on-5-yl group, a 1-difluoromethyl-1H-pyridin-2-on-5-yl group, a 1-(2,2-difluoroethyl)-1H-pyridin-2-on-5-yl group, a 1-(2,2,2-trifluoroethyl)-1H-pyridin-2-on-5-yl group, a 1-(2-fluoroethoxy)-1H-pyridin-2-on-5-yl group, a 1-cyclopropyl-1H-pyridin-2-on-5-yl group, a 1-cyclobutyl-1H-pyridin-2-on-5-yl group, a 1-cyclopropyl-1H-pyridin-2-on-5-yl group, a 1-cyclobutyl-1H-pyridin-2-on-5-yl group, a 1-cyclopentyl-1H-pyridin-2-on-5-yl group, a 1-methyl-1H-pyridin-2-on-3-yl group, a 1-ethyl-1H-pyridin-2-on-3-yl group, a 1-cyclopentyl-1H-pyridin-2-on-3-yl group, a 1-cyclopentyl-1H-pyridin-2-on-3-yl group.

When $Q_1$ is a "naphthyl group", the substituent which the naphthyl group may have is, for example, preferably any of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group of the substituents which $Q_1$ may have; more preferably a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The naphthyl group may have one or two such substituents at the bondable position thereof.

—Y of formula (IV) in which $Q_1$ is a "naphthyl group" that may be substituted with any of these substituents includes more concretely, for example, a 5-cyanonaphthalen-1-yl group, a 6-cyanonaphthalen-1-yl group, a 7-cyanonaphthalen-1-yl group, a 5-cyanonaphthalen-2-yl group, a 6-cyanonaphthalen-2-yl group, a 7-cyanonaphthalen-2-yl group, a 5-fluoronaphthalen-1-yl group, a 6-fluoronaphthalen-1-yl group, a 7-fluoronaphthalen-1-yl group, a 5-fluoronaphthalen-2-yl group, a 6-fluoronaphthalen-2-yl group, a 7-fluoronaphthalen-2-yl group, a 5-methoxynaphthalen-1-yl group, a 6-methoxynaphthalen-1-yl group, a 7-methoxynaphthalen-1-yl group, a 5-methoxynaphthalen-2-yl group, a 6-methoxynaphthalen-2-yl group, a 7-methoxynaphthalen-2-yl group, a 5-hydroxynaphthalen-1-yl group, a 6-hydroxynaphthalen-1-yl group, a 7-hydroxynaphthalen-1-yl group, a 5-hydroxynaphthalen-2-yl group, a 6-hydroxynaphthalen-2-yl group, a 7-hydroxynaphthalen-2-yl group, a 5-methylsulfonylnaphthalen-1-yl group, a 6-methylsulfonylnaphthalen-1-yl group, a 7-methylsulfonylnaphthalen-1-yl group, a 5-methylsulfonylnaphthalen-2-yl group, a 6-methylsulfonylnaphthalen-2-yl group, a 7-methylsuflonynaphthalen-2-yl group, a 5-trifluoromethylnaphthalen-1-yl group, a 6-trifluoromehtylnaphthalen-1-yl group, a 7-trifluoromehtylnaphthalen-1-yl group, a 5-trifluoromethylnaphthalen-2-yl group, a 6-trifluoromethylnaphthalen-2-yl group, a 7-trifluoromethylnaphthalen-2-yl group.

"Condensed-cyclic heteroaryl group" represented by $Q_1$ means a bicyclic group formed through condensation of a benzene or pyridine ring with a 5- to 7-membered monocyclic ring having from 1 to 3 hetero atoms selected from a group consisting of an oxygen atom, a sulfur atom and a nitrogen atom, or means a tricyclic group that comprises the bicyclic ring and a benzene or pyridine ring bonding thereto.

"Condensed-cyclic heteroaryl group" represented by $Q_1$ includes, for example, a benzofuranyl group, an indolyl group, a quinolinyl group, an isoquinolinyl group, a benzoxazolyl group, a benzimidazolyl group, a phthalazinyl group, a naphthyridinyl group, a quinoxalinyl group, a quinazolinyl group, a cinnolinyl group, an imidazopyridinyl group, a triazolopyridinyl group. Of those, preferred are a benzofuranyl group, an indolyl group, a quinolinyl group, an isoquinolinyl group, a benzoxazolyl group, a benzimidazolyl group, a phthalazinyl group, a naphthyridinyl group, a quinoxalinyl group, a quinazolinyl group, a cinnolinyl group, an imidazopyridinyl group, a triazolopyridyl group; and more preferred are a quinolinyl group, an isoquinolinyl group, a benzoxazolyl group, a benzimidazolyl group, a phthalazinyl group, a naphthyridinyl group, a quinoxalinyl group, a quinazolinyl group, a cinnolinyl group, an imidazopyridinyl group, triazolopyridinyl group.

When $Q_1$ is a "condensed-cyclic heteroaryl group", the substituent which the condensed-cyclic heteroaryl group may have is, for example, preferably any of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group of the substituents which $Q_1$ may have; more preferably a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group or an alkanoyl group. The condensed-cyclic heteroaryl group may have one or two such substituents at the bondable position thereof.

—Y of formula (IV) in which $Q_1$ is a "naphthyl group" that may be substituted with any of these substituents includes more concretely, for example, a quinolin-3-yl group, a quinolin-2-yl group, a 1H-indol-6-yl group, a 1H-indol-7-yl group, an indolin-2-on-6-yl group, an indolin-2-on-7-yl group, a 1-methylindolin-2-on-6-yl group, a 1-methylindolin-2-on-7-yl group, a 1-ethylindolin-2-on-6-yl group, a 1-ethylindolin-2-on-7-yl group, a 1-(difluoromethyl)indolin-2-on-6-yl group, a 1-(difluoromethyl)indolin-2-on-7-yl group, a quinolin-8-yl group, a quinolin-7-yl group, a dibenzofuran-3-yl group, a dibenzothiophen-3-yl group.

When $Q_1$ is a linear or branched lower alkyl group, a phenyl group, a 5- or 6-membered heteroaryl group, a heterocyclic group having from 3 to 8 carbon atoms (in which the hetero ring has 1 or 2 nitrogen atoms or oxygen atoms), a naphthyl group or a condensed-cyclic heteroaryl group, which may be substituted, and when the substituent which $Q_1$ may have is a "lactam ring", the lactam ring means a 3- to 9-membered monocyclic group having a group of —N($R^3$)—C(O)— in the ring, and it may have 1 or 2 carbon-carbon double bonds. (In this, $R^3$ represents a hydrogen atom or a lower alkyl group.)

Except the nitrogen atom that constitutes —N—C(O)— in the lactam ring, the ring may have 1 or 2 oxygen atoms or nitrogen atoms. The position of the lactam ring that bonds to $Q_1$ is not specifically defined, and the ring may bond to it at any bondable position thereof.

More concretely, the lactam ring includes, for example, those of the following formulae:

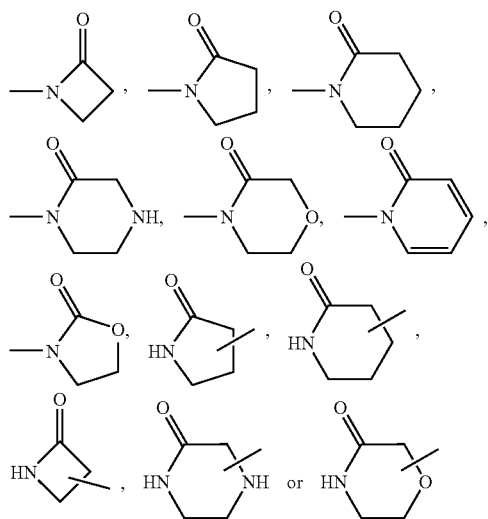

When $Q_1$ is a group of the above-mentioned formula (V-1):

(wherein the symbols have the same meanings as above), the group is described below.

Of the group of formula (V-1), $Q_1$ is preferably a group of a formula (V-10):

(wherein the symbols have the same meanings as above).

"Alkyl group having from 1 to 6 carbon atoms" represented by $R^1$ and $R^2$ in formula (V-1) for $Q_1$ may be the same linear or branched alkyl group as that mentioned hereinabove. Of those, the lower alkyl group is preferably a methyl group, an ethyl group, a propyl group, an isopropyl group, a butyl group, an isobutyl group, a sec-butyl group, a tert-butyl group, a pentyl group, an isoamyl group, a neopentyl group, a hexyl group or an isohexyl group, more preferably a methyl group, an ethyl group, a propyl group, an isopropyl group, a butyl group, an isobutyl group, a pentyl group, an isoamyl group, a neopentyl group or a hexyl group.

—Y of formula (IV) in which $Q_1$ is a group of formula (V-1) and $R^1$ and $R^2$ are the same or different, each representing a lower alkyl group, includes more concretely, for example, an N,N-diethylamino group, an N,N-dipropylamino group, an N,N-diisopropylamino group, an N,N-dibutylamino group, an N,N-dipentylamino group, an N,N-dihexylamino group, an N,N-diheptylamino group, an N-methyl-N-ethylamino group, an N-methyl-N-propylamino group, an N-methyl-N-isopropylamino group, an N-methyl-N-butylamino group, an N-methyl-N-pentylamino group, an N-methyl-N-hexylamino group, an N-methyl-N-heptylamino group, an N-ethyl-N-propylamino group, an N-ethyl-N-isopropylamino group, an N-ethyl-N-butylamino group, an N-ethyl-N-pentylamino group, an N-ethyl-N-hexylamino group, an N-ethyl-N-heptylamino group.

"Mono-lower alkylcarbamoyl group" represented by $R^1$ and $R^2$ in formula (V-1) for $Q_1$ may have the same meaning as the above-defined "mono-lower alkylcarbamoyl group". Of those, preferred are a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group; and more preferred are a methylcarbamoyl group, an ethylcarbamoyl group, a propylcarbamoyl group, an isopropylcarbamoyl group, a tert-butylcarbamoyl group.

"Di-lower alkylcarbamoyl group" represented by $R^1$ and $R^2$ in formula (V-1) for $Q_1$ means a carbamoyl group di-substituted with the above-mentioned, same or different lower alkyl groups. "Di-lower alkylcarbamoyl group" includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

The "di-lower alkylcarbamoyl group" may include a 5- to 8-membered monocyclic structure formed by the nitrogen atom of the carbamoyl group and the same or different lower alkyl groups bonding to the nitrogen atom, and may include a bicyclic structure formed through condensation of the monocyclic structure and a benzene or pyridine ring. Concretely, it may include groups of the following formulae:

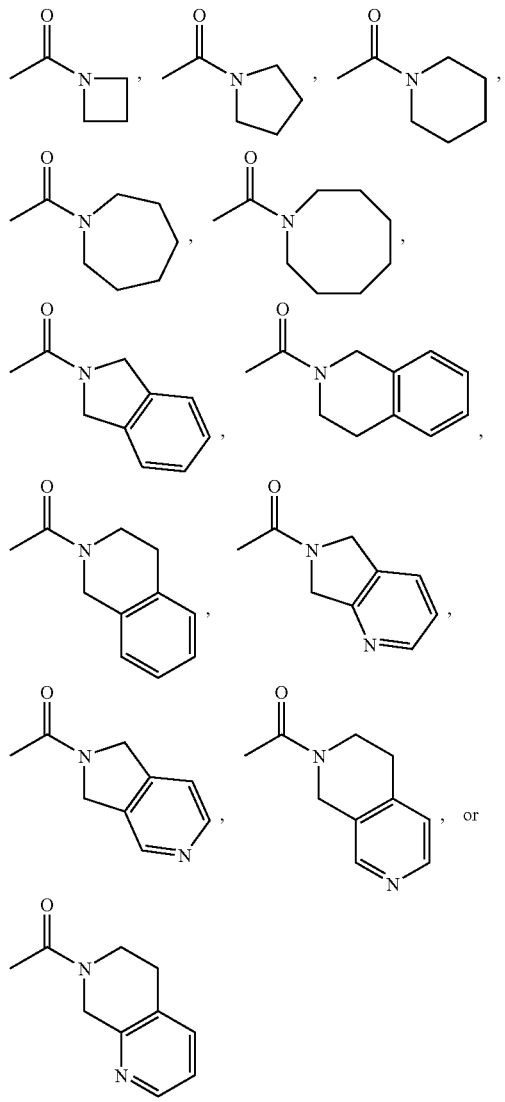

When $R_1$ and $R_2$ in formula (V-1) for $Q^1$ each represents "a lower alkyl group or a mono- or di-lower alkylcarbamoyl group", they may be the same or different.

—Y of formula (IV) in which $Q_1$ is a group of formula (V-1) and $R^1$ and $R^2$ are the same or different, each representing a lower alkyl group or a mono- or di-lower alkylcarbamoyl group, includes more concretely, for example, an N-methyl-N-(dimethylcarbamoylmethyl)amino group, an N-methyl-N-(dimethylcarbamoylethyl)amino group, an N-methyl-N-(diethylcarbamoylmethyl)amino group, an N-methyl-N-(diethylcarbamoylethyl)amino group, an N-methyl-N-(dimethylcarbamoylmethyl)aminomethyl group, an N-methyl-N-(dimethylcarbamoylethyl)aminomethyl group, an N-methyl-N-(dimethylcarbamoylmethyl)aminoethyl group, an N-methyl-N-(diethylcarbamoylmethyl)aminoethyl group.

When $Q_1$ is a group of formula (V-1) and when $R^1$ and $R^2$ form, along with the nitrogen atom adjacent thereto, a 3- to 9-membered lactam ring, then the "3- to 9-membered lactam ring" means a 3- to 9-membered group containing a group of —N—C(O)— in the ring, and it may have 1 or 2 oxygen atoms or nitrogen atoms in addition to the nitrogen atom that constitutes the group of —N—C(O)— in the lactam ring. The lactam ring includes, for example, groups of the following formula ($Q_1$-2):

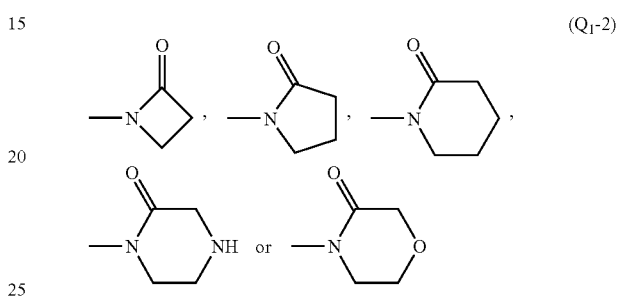

Of those, preferred are groups of the following formula ($Q_1$-20):

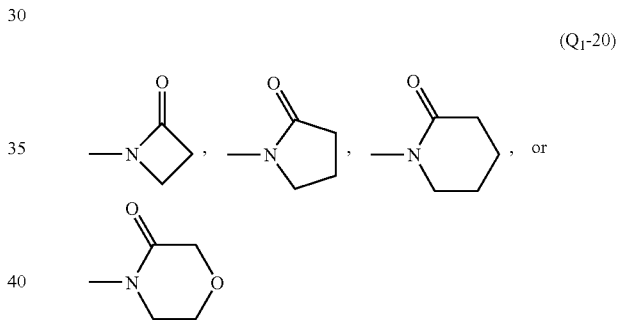

—Y of formula (IV) in which $Q_1$ i a group of formula (V-1) and $R^1$ and $R^2$ are the same or different, each representing a lower alkylcarbamoyl group, includes more concretely, for example, a 1H-pyridin-2-on-1-yl group, a pyrrolidin-2-on-1-yl group, a piperidin-2-on-1-yl group, a homopiperidin-2-on-1-yl group, a heptamethylenimin-2-on-1-yl group, a morpholin-2-on-1-yl group, a homomorpholin-2-on-1-yl group, a 1H-pyridin-2-on-1-ylmethyl group, a pyrrolidin-2-on-1-ylmethyl group, a piperidin-2-on-1-ylmethyl group, a homopiperidin-2-on-1-ylmethyl group, a heptamethylenimin-2-on-1-ylmethyl group, a morpholin-2-on-1-ylmethyl group, a homomorpholin-2-on-1-ylmethyl group, a 1H-pyridin-2-on-1-yl group, a pyrrolidin-2-on-1-yl group, a piperidin-2-on-1-ylethyl group, a homopiperidin-2-on-1-ylethyl group, a heptamethylenimin-2-on-1-ylethyl group, a morpholin-2-on-1-ylethyl group, a homomorpholin-2-on-1-ylethyl group.

When $Q_1$ is a group of formula (V-1) and when $R^1$ and $R^2$ form, along with the nitrogen atom adjacent thereto, a heterocyclic group having from 3 to 8 carbon atoms, the "heterocyclic group having from 3 to 8 carbon atoms" means a 3- to 8-membered heterocyclic group having 1 or 2 nitrogen atoms or oxygen atoms as the constitutive atoms of the hetero ring, and it includes, for example, an azetidinyl group, a pyrrolidinyl group, a piperidinyl group, a homopiperidinyl group, a heptamethyleniminyl group, a morpholinyl group, a homomorpholinyl group. Of those, preferred are a piperidinyl group, a homopiperidinyl group, a heptamethyleniminyl group, a morpholinyl group, a homomorpholinyl group.

—Y of formula (IV) in which $Q_1$ is a group of formula (V-1) and $R^1$ and $R^2$ form, along with the nitrogen atom adjacent thereto, a heterocyclic group having from 3 to 8 carbon atoms (which has 1 or 2 nitrogen atoms or oxygen atoms as the constitutive atoms of the ring) includes more concretely, for example, a morpholin-1-yl group, a homomorpholin-1-yl group, a morpholin-1-ylmethyl group, a homomorpholin-1-ylmethyl group, a 2-(morpholin-1-yl)ethyl group, a 2-(homomorpholin-1-yl)ethyl group, a 3-(morpholin-1-yl)propyl group, a 3-(homomorpholin-1-yl)propyl group.

When $Q_1$ is a group of formula (V-1) and when $R^1$ and $R^2$ form, along with the nitrogen atom adjacent thereto, a 5-membered heteroaryl group, the "5-membered heteroaryl group" means a 5-membered monocyclic group having the same or different, from 1 to 4 hetero atoms selected from a nitrogen atom, a sulfur atom and an oxygen atom in the ring, and it includes, for example, a pyrrolyl group, an imidazolyl group, a pyrazolyl group, a triazolyl group, a tetrazolyl group, an oxazolyl group, a thiazolyl group, a thiadiazolyl group. Of those, preferred are pyrazole, triazole, tetrazole, oxazole, thiazole, thiadiazole; and more preferred are pyrazole, triazole, oxazole, thiazole, thiadiazole.

—Y of formula (IV) in which $Q_1$ is a group of formula (V-1) and $R^1$ and $R^2$ form, along with the nitrogen atom adjacent thereto, a 5-membered heteroaryl group, includes more concretely, for example, a pyrazol-1-yl group, a 3-phenylpyrazol-1-yl group, a 4-phenylpyrazol-1-yl group, a 5-phenylpyrazol-1-yl group, a triazol-1-yl group, a tetrazol-1-yl group, a pyrazol-1-ylmethyl group, a triazol-1-ylmethyl group, a tetrazol-1-ylmethyl group, a 2-(pyrazol-1-yl)ethyl group, a 2-(triazol-1-yl)ethyl group, a 2-(tetrazol-1-yl)ethyl group.

—Y of formula (IV) in which $Q_1$ is a group of formula (V-1) and $R^1$ and $R^2$ form, along with the nitrogen atom adjacent thereto, a condensed-cyclic heteroaryl group, includes more concretely, for example, a benzimidazol-1-yl group, a 6-cyanobenzimidazol-1-yl group, a 7-cyanobenzimidazol-1-yl group, a 6-(trifluoromethyl)benzimidazol-1-yl group, a 7-(trifluoromethyl)benzimidazol-1-yl group, a 6-phenylbenzimidazol-1-yl group, a 7-phenylbenzimidazol-1-yl group, a benzotriazol-1-yl group, a benzotriazol-2-yl group, an imidazo[1,2,a]pyridin-6-yl group, a benzimidazol-1-ylmethyl group, a benzotriazol-1-ylmethyl group, a benzotriazol-2-ylmethyl group, an imidazo[1,2,a]pyridin-6-ylmethyl group, a 2-(benzimidazol-1-yl)ethyl group, a 2-(benzotirazol-1-yl)ethyl group, a 2-(benzotriazol-2-yl)ethyl group, a 2-(imidazo[1,2,a]pyridin-6-yl)ethyl group.

More concretely, the compounds (I) of the invention include, for example, 2-(1-cyclopentylpyrid-4-yloxy)-5-(4-cyanophenyl)pyrimidine, 2-(1-isopropylpiperidin-4-yloxy)-5-(4-cyanophenyl)pyrimidine, 2-(1-cylopentylpyrrolidin-3-yloxy)-5-(4-carbamoylphenyl)pyrimidine, 2-(1-cyclopentylpyrrolidin-3-yloxy)-5-(4-cyanophenyl)pyrimidine, 2-(1-cyclopentylpiperidin-4-yloxy)-5-{(3-methyl-1,2,4-oxadiazol-5-yl)phenyl}pyrimidine, 2-(1-cyclopentylpiperidin-4-yloxy)-5-(4-cyanophenyl)pyridine, 2-(1-cyclobutylpiperidin-4-yloxy)-5-(4-cyanophenyl)pyrimidine, 2-(1-cyclohexylpiperidin-4-yloxy)-5-(4-cyanophenyl)pyrimidine, 2-(1-cyclopropylpiperidin-4-yloxy)-5-(4-cyanophenyl)pyrimidine, 2-(1-ethylpiperidin-4-yloxy)-5-(4-cyanophenyl)pyrimidine, 2-(1-cyclopentylpiperidin-4-yloxy)-5-{4-(pyrrolidin-1-ylcarbonyl)phenyl}pyrimidine, 2-(1-cyclopentylpiperidin-4-yloxy)-5-{4-(dimethylcarbamoyl)phenyl}pyrimidine, 2-(1-cyclopentylpiperidin-4-yloxy)-5-{4-(morpholin-4-ylcarbonyl)phenyl}pyrimidine, 2-(1-cyclopentylpiperidin-4-yloxy)-5-{4-(phenoxy)phenyl}pyrimidine, 2-(1-cyclopentylpiperidin-4-yloxy)-5-(3-quinolinyl)pyrimidine, 2-(1-cyclopentylpiperidin-4-yloxy)-5-{5-indolyl}pyrimidine, 2-(1-cyclopentylpiperidin-4-yloxy)-5-(1H-pyridin-2-on-1-yl)pyrimidine, 2-(1-cyclopentylpiperidin-4-yloxy)-5-(piperidin-2-on-1-yl)pyrimidine, 2-(1-cyclopentylpiperidin-4-yloxy)-5-(8-quinolinyl)pyrimidine, 2-(1-cyclopentylpiperidin-4-yloxy)-5-(4-phenyl4-hydroxypiperidin-1-yl)pyrimidine, 2-(1-cyclopentylpiperidin-4-yloxy)-5-(2-methoxypyridin-5-yl)pyrimidine, 2-(1-cyclopentylpiperidin-4-yloxy)-5-(4-chlorophenyl)pyrimidine, 2-(1-cyclopentylpiperidin-4-yloxy)-5-(4-trifluoromethylphenyl)pyrimidine, 2-(1-cyclopentylpiperidin-4-yloxy)-5-(pyridin-3-yl)pyrimidine, 2-(1-cyclopentylpiperidin-4-yloxy)-5-(4-methoxyphenyl)pyrimidine, 2-(1-cyclopentylpiperidin-4-yloxy)-5-(dibenzofuran-4-yl)pyrimidine, 2-(1-cyclopentylpiperidin-4-yloxy)-5-(2-cyclopentyloxypyridin-5-yl)pyrimidine, 2-(1-cyclopentylpiperidin-4-yloxy)-5-(1H-pyridin-2-on-5-yl)pyrimidine, 2-(1-cyclopentylpiperidin-4-yloxy)-5-(1-cyclopentyl-1H-pyridin-2-on-3-yl)pyrimidine, 2-(1-cyclopentylpiperidin-4-yloxy)-5-{2-(pyrrolidin-1-ylcarbonyl)pyridin-5-yl}pyrimidine, 2-(1-cyclopentylpiperidin-4-yloxy)-5-(2-cyano-5-thenyl)pyrimidine, 2-(1-cyclopentylpiperidin-4-yloxy)-5-{4-(morpholin-3-on-4-yl)phenyl}pyrimidine, 2-(1-cyclopentylpiperidin-4-yloxy)-5-{4-(2-oxazolidinon-3-yl)phenyl}pyrimidine, 2-(1-cyclopentylpiperidin-4-yloxy)-5-(2-methylpyridin-5-yl)pyrimidine, 2-(1-cyclopentylpiperidin-4-yloxy)-5-(2-fluoropyridin-5-yl)pyrimidine, 2-(1-cyclopentylpiperidin-4-yloxy)-5-{4-(1H-pyridin-2-on-1-yl)phenyl}pyrimidine, 2-(1-cyclopentylpiperidin-4-yloxy)-5-{4-(methylsulfonyl)phenyl}pyrimidine, 2-(1-cyclopentylpiperidin-4-yloxy)-5-{4-acetylphenyl}pyrimidine, 2-(1-cyclopentylpiperidin-4-yloxy)-5-(4-trifluoromethoxyphenyl)pyrimidine, 2-(1-cyclopentylpiperidin-4-yloxy)-5-{4-(2-hydroxy-2-propyl)phenyl}pyrimidine, 2-(1-cyclopentylpiperidin-4-yloxy)-5-(2-ethylpyridin-5-yl)pyrimidine, 2-(1-cyclopentylpiperidin-4-yloxy)-5-(4-cyanophenyl)pyrazine, 5-(1-cyclopentylpiperidin-4-yloxy)-2-(4-cyanophenyl)pyridine, 2-(1-cyclopentylpiperidin-4-yloxy)-5-(4-cyanophenyl)pyridazine, 2-(1-cyclopentylpiperidin-4-yloxy)-5-(piperidin-1-ylcarbonyl)pyrimidine, 2-(1-cyclopentylpiperidin-4-yloxy)-5-(piperidin-1-ylmethyl)phenyl}pyrimidine, 2-(1-(cyclopentylpiperidin-4-yloxy)-5-(4-phenylpiperazin-1-ylmethyl)pyrimidine, 2-(1-cyclopentylpiperidin-4-yloxy)-5-(2-cyanopyrimidin-5-yl)pyrimidine, 2-(1-cyclopentylpiperidin-4-yloxy)-5-(1H-pyridin-2-on-4-yl)pyrimidine, 2-(1-cyclopentylpiperidin-4-yloxy)-5-(1-methyl-1H-pyridin-2-on-4-yl)pyrimidine, 2-(1-cyclopentylpiperidin-4-yloxy)-5-(2-difluoromethoxypyridin-4-yl)pyrimidine, 2-(1-cyclopentylpiperidin-4-yloxy)-5-(1-difluoromethyl-1H-pyridin-2-on-4-yl)pyrimidine, 2-(1-cyclopentylpiperidin-4-yloxy)-5-{4-(N-methyl-N-methoxycarbonylamino)phenyl}pyrimidine, 2-(1-cyclopentylpiperidin-4-yloxy)-5-(1-ethyl-1H-pyridin-2-on-4-yl)pyrimidine, 2-(1-cyclopentylpiperidin-4-yloxy)-5-(1-methyl-1H-pyridin-2-on-5-yl)pyrimidine, 2-(1-cyclopentylpiperidin-4-yloxy)-5-(1-ethyl-1H-pyridin-2-on-5-yl)pyrimidine, 2-(1-cyclopentylpiperidin-4-yloxy)-5-(2-methylimidazo[1,2,a]pyridin-6-yl)pyrimidine, 2-(1-cyclopentylpiperidin-4-yloxy)-5-(2-carbamoylpyridin-5-yl)pyrimidine, 2-(1- cyclopentylpiperidin-4-yloxy)-5-{1-(2,2-difluoroethyl)-1H-pyridin-2-on-4-yl}pyrimidine, 2-(1-cyclopentylpiperidin-4-yloxy)-5-(1,2,4-triazolo[4,3,a]pyridin-7-yl)pyrimidine, 2-(1-cyclopentylpiperidin-4-yloxy)-5-(1,2,4-triazolo[4,3,a]pyridin-6-yl)pyrimidine, 2-(1-cyclopentylpiperidin-4-yloxy)-5-(1-methyl-1H-pyridin-2-on-5-yl)pyridine, 2-(1-cyclopentylpiperidin-4-yloxy)-5-(1-difluoromethyl-1H-pyridin-2-on-5-yl)pyridine, 2-(1-cyclobutylpiperidin-4-yloxy)-5-(1-difluoromethyl-1H-pyridin-2-on-4-yl)pyrimidine, 2-(1-cyclobutylpiperidin-4-yloxy)-5-(1-methyl-1H-pyridin-2-on-5-yl)pyridine, 2-(1-cyclobutylpiperidin-4-yloxy)-5-{1-(2-fluoroethyl)-1H-pyridin-2-on-4-yl}pyrimidine, 2-(1-cyclopentylpiperidin-4-yloxy)-5-{1-(2-fluoroethyl)-1H-pyridin-2-on-4-yl}pyrimidine, 2-(1-isopropylpiperidin-4-yloxy)-5-(1-methyl-1H-pyridin-2-on-5-yl)pyridine, 2-(1-cyclobutylpiperidin-4-yloxy)-5-{1-(2-fluoroethyl)-1H-pyridin-2-on-5-yl}pyridin, 2-(1-cyclobutylpiperidin-4-yloxy)-5-{1-(2-fluoroethoxy-1H-pyridin-2-on-5-yl}pyridine, 2-(1-cyclobutylpiperidin-4-yloxy)-5-{1-(2-fluoroethyl)-1H-pyridin-2-on-4-yl}pyridin, 2-(1-cyclobutylpiperidin-4-yloxy)-5-(3-chloro-1-methyl-1H-pyridin-2-on-5-yl)pyridine, 2-(1-cyclobutylpiperidin-4-yloxy)-5-{1-(2-fluoroethyl-1H-pyridin-2-on-4-yl}pyridine, 2-(1-cyclobutylpiperidin-4-yloxy)-5-(3-chloro-1-methyl-1H-pyridin-2-on-5-yl)pyridine, 2-(1-cyclobutylpiperidin-4-yloxy)-5-(1-ethyl-1H-pyridin-2-on-5-yl)pyridine, 2-(1-isopropylpiperidin-4-yloxy)-5-(1-ethyl-1H-pyridin-2-on-5-yl)pyridine.

The compounds (I) of the invention have an effect as a histamine-H3 acceptor antagonist or inverse-agonist.

"Histamine-H3 receptor inverse-agonist" as referred to herein means a receptor-binding substrate that has an effect completely or partially opposite to the effect of a histamine-H3 receptor agonist, and is a ligand capable of inhibiting the homeostatic activity of a histamine-H3 receptor.

Methods for producing the compounds of the invention are described below.

The compounds (I) of the invention may be readily produced, using any known reaction methods or according to any per-se known methods. The compounds (I) of the invention may be produced not only according to ordinary liquid-phase production methods but also according to any solid-phase methods such as combinatorial production methods or parallel production methods that are being significantly developed these days.

The compounds of the invention may be produced, for example, according to the methods mentioned below.

Production Method 1

A compound of a general formula (VI):

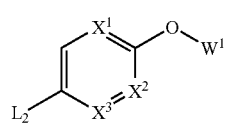
(VI)

[wherein $W^1$ represents a group of the following formula (II-1):

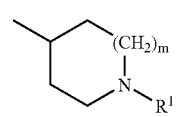
(II-1)

(wherein m indicates an integer of from 0 to 3; $R^1$ represents a linear or branched lower alkyl group (excepting a methyl group), a cycloalkyl group having from 3 to 9 carbon atoms, an aralkyl group or a heterocyclic group having from 3 to 8 carbon atoms (the hetero ring has 1 or 2 nitrogen atoms or oxygen atoms), which may be substituted with a group selected from a class consisting of a cyano group, a hydroxyl group, a lower alkyl group (the lower alkyl group may be substituted with a hydroxyl group, a halogen atom or an amino group), a lower alkoxy group (the lower alkoxy group may be substituted with a halogen atom), a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbonyl group and a trifluoromethyl group, or represents a group corresponding to R but having a protective group suitably introduced into the substituent which R has), or represents a group or a formula (III):

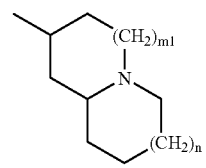
(III)

(wherein m1 indicates an integer of from 0 to 3; n indicates an integer of from 0 to 2); and $L_3$ represents a leaving group], is reacted with a compound of a general formula (XI):

Met-$Y^{1p}$ (XI)

[wherein Met represents a general organic metal atom; $Y^{1p}$ represents a group of a formula (IV):

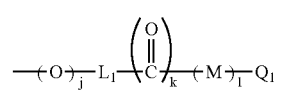
(IV)

(wherein j, k and l each independently indicate 0 or 1; $L_1$ represents a lower alkylene group having from 1 to 4 carbon atoms, or a single bond; M represents an oxygen atom or a group of a formula (V):

(V)

(wherein $R^0$ represents a lower alkyl group having from 1 to 4 carbon atoms); $Q_1$ represents a linear or branched lower alkyl group, a cycloalkyl group having from 3 to 9 carbon atoms, a phenyl group, a 5-membered or 6-membered heteroaryl group, a heterocyclic group having from 3 to 8 carbon atoms (the hetero ring may have 1 or 2 nitrogen atoms or oxygen atoms), a naphthyl group or a condensed-cyclic heteroaryl group, which may be substituted with a group selected from a class consisting of a cyano group, a hydroxy group, a lower alkyl group (the lower alkyl group may be substituted with a hydroxy group, a halogen atom or an amino group), a lower alkoxy group (the lower alkoxy group may be substituted with a halogen atom), a lower alkylsulfonyl group, a cyclo-lower alkylsulfonyl group, a halogen atom, a mono-lower alkylaminocarbonyloxy group, a di-lower alkylaminocarbonyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group, or represents a group corresponding to $Q_1$ but having a protective group optionally introduced into the substituent which $Q_1$ has, or represents a group of a formula (V-1):

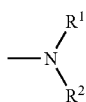

(V-1)

(wherein $R^1$ and $R^2$ are the same or different, each representing a lower alkyl group or a mono- or di-lower alkylcarbamoyl group, or $R^1$ and $R^2$ together form, along with the adjacent nitrogen atom, a 3- to 9-membered lactam ring, a heterocyclic group having from 3 to 8 carbon atoms (the group has 1 or 2 nitrogen atoms or oxygen atoms in the ring thereof), a 5-membered heteroaryl group or a condensed-cyclic heteroaryl group), or represents a group corresponding to —Y but having a protective group optionally introduced into the substituent which —Y has], in the presence of a catalyst, to give a compound of a general formula (VIII):

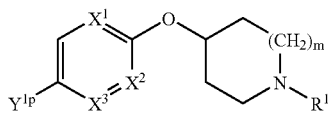

(VIII)

[wherein $X^1$, $X^2$, $X^3$, m, $R^1$ and $Y^{1p}$ have the same meanings as above], or a compound of a general formula (IX):

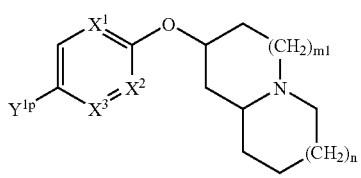

(IX)

[wherein $X^1$, $X^2$, $X^3$, $m^1$, n and $Y^{1p}$ have the same meanings as above], and optionally the protective group is removed to give a compound of a general formula (I-2):

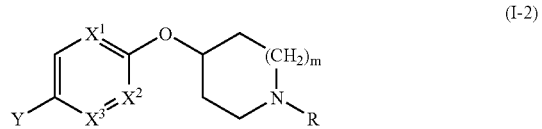

(I-2)

[wherein $X^1$, $X^2$, $X^3$, m, R and Y have the same meanings as above], or a compound of a general formula (I-3):

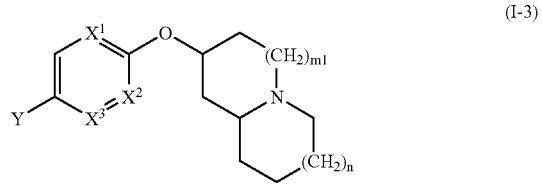

(I-3)

[wherein $X^1$, $X^2$, $X^3$, $m^1$, n and Y have the same meanings as above].

The general organic metal atom of Met means an organic metal atom generally used in cross-coupling reaction, including, for example, lithium, boron, silicon, magnesium, aluminium, zinc, tin, more preferably boron, zinc, and tin. Regarding the concrete embodiments of its use, for example, boron may be used as boric acid or borates; zinc may be used as zinc chloride, zinc bromide or zinc iodide; and tin may be used as tri-lower alkyl-tin.

The leaving group for $L_2$ may be any one having the function of leaving in the reaction of the compounds of formulae (VI) and (VII). More concretely, $Y^{1p}$ includes, for example, a halogen atom such as a chlorine atom, a bromine atom or an iodine atom; an organic sulfonyl group such as a methanesulfonyl group, an ethanesulfonyl group, a benzenesulfonyl group; and an organic sulfonyloxy group such as a methanesulfonyloxy group, a trifluoromethanesulfonyloxy group, and a p-toluenesulfonyloxy group.

Regarding the reaction between the compound of formula (VI) and the compound of formula (VII), in general, from 0.5 mols to 5 mols, preferably from 0.7 mols to 3 mols of the compound (VII) is reacted with 1 mol of the compound (X).

The catalyst to be used in the reaction is, for example, a transition metal generally used in cross-coupling, such as copper, nickel, palladium. More concretely, preferred are tetrakis(triphenylphosphine)palladium(0), palladium(II) acetate, bis(triphenylphosphine)palladium(II) chloride, [1,1'-bis(diphenylphosphino)ferrocene]palladium(II) dichloride.

The reaction is effected generally in an inert solvent. The insert solvent is, for example, preferably water, benzene, toluene, xylene, methylene chloride, chloroform, dimethoxyethane, tetrahydrofuran, dioxane, dimethylformamide, and their mixed solvents.

The reaction temperature may be generally from room temperature to the boiling point of the solvent used in the reaction, preferably from 20° C. to 200° C.

The reaction time may be generally from 30 minutes to 7 days, preferably from 3 hours to 2 days.

Preferably, the reaction is effected in the presence of a base. The base includes, for example, an inorganic base such as sodium hydroxide, potassium hydroxide, sodium hydrogencarbonate, sodium carbonate, potassium carbonate, cesium carbonate; and an organic base such as triethylamine, diisopropylamine.

The amount of the base to be used may be generally from 0.5 mols to 5 mols, preferably from 0.7 mols to 3 mols relative to 1 mol of the compound of formula (VI).

After the reaction, when the reaction product has a protective group, then the protective group is removed, but when the reaction product does not have a protective group, then it may be directly processed in an ordinary manner to obtain a compound (I-2) or (I-3) of the invention.

Thus obtained, the compound (I-2) or (I-3) of the invention may be isolated and purified in any known isolation and purification method, for example, through concentration, reduced-pressure concentration, recrystallization, reprecipitation, solvent extraction or chromatography.

The compounds of formulae (VI), (VII), (IX) and (X) may be commercially-available ones, or may be prepared in any known methods or according to such known methods, or according to the methods described in Examples and Reference Examples given hereinunder, optionally suitably combining any of such methods.

In the above-mentioned reaction, when the reactants have a group not participating in the reaction, such as an amino group, an imino group, a hydroxyl group, a carboxyl group, an oxo group or a carbonyl group, then the amino group, the imino group, the hydroxyl group, the carboxyl group, the oxo group or the carbonyl group may be suitably protected with a protective group for the amino group or the imino group, or a protective group for the hydroxyl group, or a protective group for the carboxyl group, or a protective group for the oxo group or the carbonyl group, and then the reaction may be effected, and, after the reaction, the protective group may be removed. The introduction and the removal of the protective group may be attained according to the methods described in *Protective Groups in Organic Synthesis* mentioned above, or according to methods similar to these, or by combining any of such methods.

"Protective group for amino group or imino group" is not specifically defined, so long as the group has its own function. For example, preferred are an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as a benzenesulfonyl group, a toluenesulfonyl group; and more preferred are an acetyl group, a benzoyl group, a tert-butoxycarbonyl group, a trimethylsilylethoxymethyl group, a methylsulfonyl group.

"Protective group for hydroxyl group" is not specifically defined, so long as the group has its own function. For example, preferred are a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group; and more preferred are a methyl group, a methoxymethyl group, a tetrahydropyranyl group, a trityl group, a trimethylsilylethoxymethyl group, a tert-butyldimethylsilyl group, an acetyl group.

"Protective group for carboxyl group" is not specifically defined, so long as the group has its own function. For example, preferred are a lower alkyl group such as a methyl group, an ethyl group, a propyl group, an isopropyl group, a tert-butyl group; a halo-lower alkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, a trityl group; and more preferred are a methyl group, an ethyl group, a tert-butyl group, a 2-propenyl group, a benzyl group, a p-methoxybenzyl group, a benzhydryl group.

"Protective group for oxo group or carbonyl group" is not specifically defined, so long as the group has its own function. For example, it includes acetals and ketals such as ethylene ketal, trimethylene ketal, dimethyl ketal.

The compounds of the invention may also be produced according to the following method.

Production Method 2

A compound of a general formula (X):

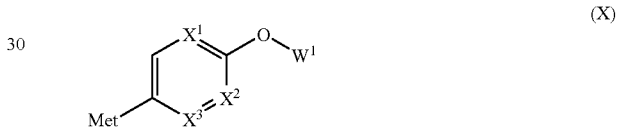

[wherein $X^1$, $X^2$, $X^3$, $W^1$ and Met have the same meanings as above] is reacted with a compound of a general formula (XI):

[wherein $L_2$ and $Y^{1p}$ have the same meanings as above] in the presence of a catalyst to give a compound of a general formula (XII):

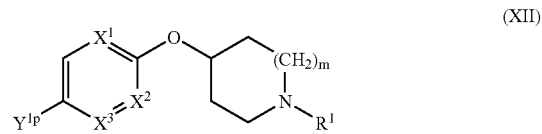

(wherein $X^1$, $X^2$, $X^3$, m, $R^1$ and $Y^{1p}$ have the same meanings as above), or a compound of a general formula (XIII):

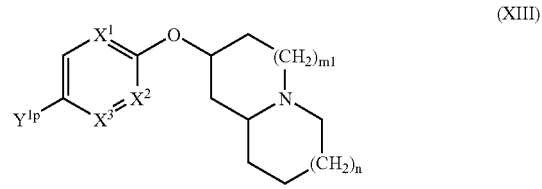

(wherein $X^1$, $X^2$, $X^3$, m1, n and $Y^{1p}$ have the same meanings as above), and optionally the protective group is removed to give a compound of a general formula (I-2):

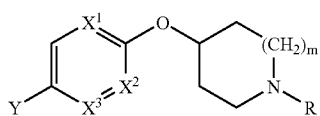

(I-2)

[wherein $X^1$, $X^2$, $X^3$, m, R and Y have the same meanings as above], or a compound of a general formula (I-3):

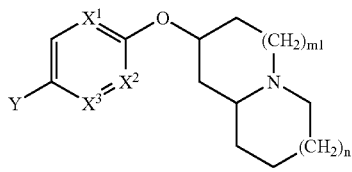

(I-3)

[wherein $X^1$, $X^2$, $X^3$, m1, n and Y have the same meanings as above].

Regarding the reaction of the compound of formula (IX) with the compound of formula (X), in general, from 0.5 mols to 5 mols, preferably from 0.7 mols to 3 mols of a compound (X) is reacted with 1 mol of a compound (IX).

The catalyst to be used in the reaction may be a transition metal generally used in cross-coupling reaction, such as copper, nickel, palladium. More concretely, preferred are tetrakis(triphenylphosphine)palladium(0), palladium(II) acetate, bis(triphenylphosphine)palladium(II) chloride, [1,1'-bis(diphenylphosphino)ferrocene]palladium(II) dichloride.

The reaction is effected generally in an inert solvent. The insert solvent is, for example, preferably water, benzene, toluene, xylene, methylene chloride, chloroform, dimethoxyethane, tetrahydrofuran, dioxane, dimethylformamide, and their mixed solvents.

The reaction temperature may be generally from room temperature to the boiling point of the solvent used in the reaction, preferably from 20° C. to 200° C.

The reaction time may be generally from 30 minutes to 7 days, preferably from 3 hours to 2 days.

Preferably, the reaction is effected in the presence of a base. The base includes, for example, an inorganic base such as sodium hydroxide, potassium hydroxide, sodium hydrogencarbonate, sodium carbonate, potassium carbonate, cesium carbonate; and an organic base such as triethylamine, diisopropylamine.

The amount of the base to be used may be generally from 0.5 mols to 5 mols, preferably from 0.7 mols to 3 mols relative to 1 mol of the compound of formula (IX).

After the reaction, when the reaction product has a protective group, then the protective group is removed, but when the reaction product does not have a protective group, then it may be directly processed in an ordinary manner to obtain a compound of the invention.

The removal of the protective group and the post-treatment of the reaction product may be effected according to the methods described hereinabove in the section or Production Method 1.

The compound of formula (X) may be prepared in any known methods or according to such known methods, or according to the methods described in Examples and Reference Examples given hereinunder, optionally suitably combining any of such methods.

The compound of formula (X) may be produced according to the following reaction:

1) Reaction of a compound of formula (VI) with a lower alkyl metal;

2) Reaction of a compound of formula (VI) with a lower alkyl metal followed by further reaction with a metal halide or an ester, or 3) Reaction of a compound of formula (VI) with a bis(trilower alkyl-tin) or bis(borate) in the presence of a catalyst.

The compounds of the invention may also be produced according to the following method.

Production Method 3

A compound of a general formula (XIV):

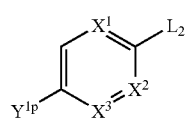

(XIV)

[wherein the symbols have the same meanings as above] is reacted with a compound of a general formula (XV):

$W^1$—OH (XV)

[wherein $W^1$ represents a group of the following formula (II-p):

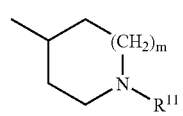

(II-p)

(wherein $R^{11}$ is $R^1$ or an amino-protective group; and the other symbols have the same meanings as above), or represents a group of a formula (III):

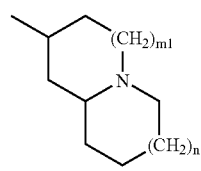

(III)

(wherein the symbols have the same meanings as above)] or its salt to give a compound of a general formula (XVI):

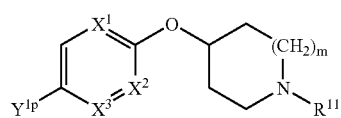

(XVI)

[wherein $X^1$, $X^2$, $X^3$, $Y^{1p}$, m and $R^{11}$ have the same meanings as above], and when the compound and $R^{11}$ have a protective group for the amino group therein, then the amino-protective group is removed, and thereafter this is further reacted with a precursor aldehyde or ketone corresponding to $R^1$ or with a compound of a general formula (XVII):

 (XVII)

[wherein the symbols have the same meanings as above], and optionally the protective group is removed to give a compound (I) of the invention:

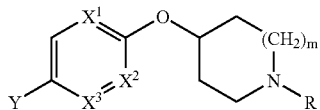 (I)

(wherein the symbols have the same meanings as above].

The compounds of formulae (I), (I-2) and (I-3) of the invention may be readily isolated and purified in any ordinary separation methods. Examples of the methods include solvent extraction, recrystallization, reprecipitation, column chromatography, thin-layer partitioning chromatography.

The compounds may be converted into pharmaceutically-acceptable salts or esters in an ordinary manner. On the contrary, their salts or esters may be converted into free compounds also in an ordinary manner.

The heteroaryloxy-nitrogen-containing saturated heterocyclic derivatives of the invention may be in the form of their pharmaceutically-acceptable salts, and the compounds of formula (I) may be produced in any ordinary manner. The acid-addition salts of the compounds includes, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; and other acid-addition salts with organic acids such as amino acids, for example, glutamates, aspartates.

The salts may also be base-addition salts, for example, salts with alkali metals such as sodium potassium; salts with alkaline earth metals such as calcium, magnesium; ammonium salts; salts with organic bases such as guanidine, triethylamine, dicyclohexylamine. Further, the compounds of the invention may also be in the form of hydrates or solvates of their free compounds or salts.

The usefulness of the compounds of formula (I) of the invention as medicines is proven, for example, by the following pharmaceutical test examples.

PHARMACEUTICAL TEST EXAMPLE 1

Histamine Analogue-Binding Inhibition Test

A cDNA sequence coding for a human histamine-3 receptor [see International Patent Application WO00/39164] was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see Proceedings of the National Academy of Sciences of the United States of America, Vol., 84, p. 7413 (1987)] to obtain histamine-3 receptor expression cells.

A membrane specimen prepared from the cells having expressed a histamine-3 receptor was incubated in an assay buffer (50 mM Tris buffer, pH 7.4) along with a test compound and 20,000 cpm of [$^3$H]-α-methylhistamine (by NEN) therein at 25° C. for 2 hours, and then filtered through a glass filter GF/C. This was washed with 50 mM Tris buffer (ph 7.4), and the radioactivity on the glass filter was measured. The non-specific binding was determined in the presence of 10 μM thioperamide (by SIGAM), and the 50% inhibitory concentration ($IC_{50}$) of the test compound to specific N-α-methylhistamine binding was calculated [see Molecular Pharmacology, Vol. 55, p. 1101 (1999)]. As a result, $IC_{50}$ of the compound of Example 1 was 15 nM.

PHARMACEUTICAL TEST EXAMPLE 2

Histamine Analogue-Binding Inhibition Test

A membrane specimen prepared from the cells having expressed a histamine-3 receptor was incubated in an assay buffer (50 mM Tris buffer, 100 mM NaCl, 5 mM $MgCl_2$, pH 7.4) along with a test compound, 20 nM R-methylhistamine (histamine analogue, by Sigma), 10 μM GDP (guanine-nucleotide diphosphate, by Sigma), 200 pM [$^{35}$S] GTPγS (guanine-nucleotide triphosphate analogue, by Amersham) and SPA resin (wheatgerm agglutinin SPA beads, by Amersham) therein on a 96-well optiplate (by Packard) at 25° C. for 3 hours and then centrifuged at 3,000 rpm, and its activity was counted with Topcount (by Packard). The non-specific binding was determined in the presence of 10 μM GTPγS (by Sigma), and the 50% inhibitory concentration ($IC_{50}$) of the test compound to specific N[$^{35}$S] GTPγS binding was calculated [see British Journal of Pharmacology, Vol. 135, p. 383 (2002)]. The results are shown in the following Table.

| Example Number | IC50 (nM) |
|---|---|
| Example 1 | 1.9 |
| Example 11 | 1.2 |
| Example 23 | 1.4 |
| Example 37 | 1.3 |
| Example 60 | 1.2 |
| Example 65 | 0.45 |
| Example 68 | 1.4 |

As in the above, the compounds of the invention strongly inhibited the binding of the histamine-3 receptor to N-α-methylhistamine (histamine analogue).

PHARMACEUTICAL TEST EXAMPLE 3

Antagonistic Test to Drinking Behavior Induced by Histamine-3 Receptor Selective Agonist R-α-methylhistamine While anesthetized with ketamine-xylazine (74 and 11 mg/kg, single intraabdominal administration), a chronic guide cannula (26 gauge, length 11 mm) was inserted into the third ventricle of male SD rats (7 to 10-weeks age, 200 to 300 g), using a brain sterotaxis device, and fixed with a dental resin. The position of the tip of the guide cannula was 2.2 mm after the bregma, on the median line and at a depth of 8 mm from the surface of the cranial bone. After the recovery period of about 1 week, R-α-methylhistamine (0.3 μg/1 μL/head, 30% propylene glycol solution) was administered into the third ventricle. A test compound suspended in an aqueous 0.5% methyl cellulose solution was orally administered to the rats 2 hours before the administration of R-α-methylhistamine thereto, and the amount of water drunk by the rats 1 hour after the administration of R-α-methylhistamine was determined.

As a result, the compound of the invention administered to the rats in an amount of 10 mg/kg significantly inhibited the increase in the amount of water drunk by the rats with R-α-methylhistamine administered to the third ventricle thereof.

PHARMACEUTICAL TEST EXAMPLE 4

Test for Internal Kinetics

A test compound was orally or intravenously administered to SD male rats (7 to 10 weeks-age, 200 to 400 g) kept away from eating and drinking overnight, and using a heparinization capillary within a predetermined period of time, about 100 μl of the blood was collected from them via their tail vein. The blood was centrifuged (4° C., 6000 rpm, 10 minutes) to collect its plasma. Ethanol (including an internal standard substance) was added to the plasma in an amount of 3 times that of the plasma, and stirred, and left statically at −20° C. for 20 minutes, and then this was centrifuged (4° C., 10,000 rpm, 10 minutes). The supernatant was analyzed through LC/MS/MS, and the plasma concentration of the compound was quantified according to a relative calibration curve method.

As a result, the bioavailability of the compound of Example 1 was 53%, and the half-value period in blood thereof was 5.3 hours.

PHARMACEUTICAL TEST EXAMPLE 5

Brain/Cerebrospinal Fluid Migration Test

A test compound was orally or intravenously administered to SD male rats (7 to 10 weeks-age, 200 to 400 g), and while anesthetized with ether for a predetermined period of time, the whole blood was collected from the abdominal aorta of the rats, using a heparin-processed syringe. Next, the brain skin was cut opened and a 30 G needle for dental use was pierced between the cervical vertebrae and inserted into the subarachnoid cavity. Through the tube connected with the dental 30 G needle, from 50 to 100 μl of the cerebrospinal fluid was collected into a 1-ml syringe, and then the brain was taken out. The blood sample was centrifuged (4° C., 6000 rpm, 10 minutes), and the resulting plasma was stirred with ethanol (including an internal standard substance) added thereto in an amount of 3 times the plasma. 2 ml of water was added to the brain sample and homogenized, and a part of the resulting mixture was stirred with ethanol (including an internal standard substance) added thereto in an amount of 3 times the mixture. These samples were kept at −20° C. for 20 minutes, and then centrifuged (4° C., 12,000 g, 10 minutes), and the resulting supernatant was analyzed through LC/MS/MS. According to a relative calibration curve method, the concentration of the test compound in the plasma, the brain and the cerebrospinal fluid was quantified.

As a result, 2 hours after the oral administration (10 mg/kg) thereof, the brain concentration of the compound of Example 1 was 6.18 nmol/g, the cerebrospinal fluid concentration thereof was 0.128 μM, and the plasma concentration thereof was 0.54 μM.

The compounds of formula (I) may be administered orally or parenterally, and may be formulated into pharmaceutical preparations suitable to such administration modes. Using them, the invention provides preventives and remedies for metabolic system diseases such as obesity, diabetes, hormone secretion disorder, hyperlipemia, gout, fatty liver; circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder; and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

In clinical use of the compounds of the invention, pharmaceutically-acceptable additives may be added thereto to formulate various preparations in accordance with the intended administration route thereof, and the preparations may be administered. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The preparations may contain the compound of the invention in an amount of from 1.0 to 100% by weight, preferably from 1.0 to 60% by weight of the preparation. The preparations may contain any other therapeutically-effective compound.

In their use, the compounds of the invention may be combined with any other agents useful for treatment of metabolic disorders and/or dietary disorders. The individual ingredients to be combined may be administered at the same time or at different times during the treatment period, either as one preparation or as divided different preparations. Accordingly, the invention should be so interpreted that it encompasses any and every administration mode at the same time or at different times, and the administration in the invention should be interpreted so. The range of the combination of the compound of the invention and the other agent useful for treatment of metabolic disorders and/or dietary disorders encompasses, in principle, all combinations of the compound of the invention and any and every agent useful for the treatment of metabolic disorders and/or dietary disorders.

The compound of the invention may be used, as combined with a pharmaceutical agent effective for hypertension, obesity-related hypertension, hypertension-related disorders, cardiomegaly, left ventricle hypertrophy, metabolic disorders, obesity, obesity-related disorders (the agent is hereinafter referred to as co-agent). In prevention and treatment of the above-mentioned diseases, the pharmaceutical agents may be administered simultaneously or separately or successively. When the compound of the invention is used along with one or more such co-agents, then they may be formulated into one pharmaceutical composition for single administration. In combination therapy, however, a composition containing the compound of the invention and a co-agent may be separately formulated in different packages, and they may be administered simultaneously or separately or successively. They may be administered at different times.

The dose of the co-agent may depend on the clinical use thereof, and may be suitably determined in accordance with the administration object, the administration route, the diseases and the combination. The form of the co-agent for administration is not specifically defined, and it may be combined with the compound of the invention when they are administered. The administration mode includes, for example, the following: (1) A compound of the invention is combined with a co-agent to give a single preparation for single administration; (2) a compound of the invention and a co-agent are separately formulated into different two preparations, and the two preparations are simultaneously administered in one administration route; (3) a compound of the invention and a co-agent are separately formulated into different two preparations, and they are administered at different times in one and the same administration route; (4) a compound of the invention and a co-agent are separately formulated into different two preparations, and they are administered at the same time in two different administration routes; (5) a compound of the invention and a co-agent are separately formulated into different two preparations, and they are administered at different times in different administration routes (for example, a compound of the invention and a co-agent are administered in that order, or in an order contrary to this). The blend ratio of the compound of the invention and the co-agent may be suitably determined depending on the administration object, the administration route, and the disease for the administration.

The co-agent for use in the invention includes, for example, "therapeutical medicines for diabetes", "therapeutical medicines for hyperlipemia", "therapeutical medicines for hypertension", and "anti-obesity medicines". Two or more these co-agents may be used, as combined in any desired ratio.

The "therapeutical medicines for diabetes" include, for example 1) PPAR-γ agonists such as glitazones [e.g., ciglitazone, darglitazone, englitazone, isoglitazone, MCC-555], pioglitazone, rosiglitazone, troglitazone, BRL49653, CLX-0921, 5-BTZD, GW-0207, LG-100641, LY-300512; 2) biguanides such as metformin, buformin, phenformin; 3) protein tyrosine phosphatase 1B inhibitors; 4) sulfonylureas such as acetohexamide, chloropropamide, diabinese, glibenclamide, glipizide, glyburide, glimepiride, glicilazide, glipentide, gliquidone, glisolamide, trazamide, tolubutamide; 5) meglitinides such as repaglinide, nateglinide; 6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14; α-amylase inhibitors such as tendamistat, trestatin, A13688; 8) insulin secretion promoters such as linogliride, A-4166; 9) fatty acid oxidation inhibitors such as clomoxir, etomoxir; 10) A2 antagonists such as midaglizole, isaglidole, derigli-dole, idazoxan, earoxan, fluparoxan; 11) insulin or insulin mimetix such as biota, LP-100, novalapid, insulin determir, insulin lispro, insulin glargine, insulin zinc, Lys-Pro-insulin, GLP-1 (73-7), GLP1 amide (7-36); 12) non-thiazolidinedione such as JT-501 and farglitazar; 13) PPARα/γ co-agonists such as CLX-0940, GW-1536, GW-1929, GW-2433, KPR-297, L-796449, L-90, SB219994.

The "therapeutical medicines for hyperlipemia" include, for example 1) bile acid absorption promoters such as cholesterylamine, colesevelem, colestipol, crosslinked dextran dialkylaminoalkyl derivatives, Colestid®, LoCholest®, Questran®; 2) HMG-CoA reductase inhibitors such as atorvastatin, itavastatin, fluvastatin, lovastatin, pravastatin, rivastatin, rosuvastatin, simvastatin, ZD-4522; 3) HMG-CoA synthase inhibitors; 4) cholesterol absorption inhibitors such as snatol ester, β-sitosterol, sterol glucoside, ezetimibe; 5) acyl-coenzyme A cholesterol transacylase inhibitors such as avasimibe, eflucimibe, KY-505, SMP-709; 6) CETP inhibitors such as JTT705, torcetrapib, CP532632, BAY-63-2149, SC-591, SC-795; 7) squalane synthesis inhibitors; 8) antioxidants such as probucol; 9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®); 10) FXR receptor antagonists such as GW4064, SR-103912; 11) LXR receptor agonists such as GW3965, T9013137, XTCO-179628; 12) lipoprotein synthesis inhibitors such as niacin; 13) renin-angiotensin system inhibitors; 14) microsome triglyceride transportation inhibitors; 15) bile acid reabsorption inhibitors such as BARA1453, SC435, PHA384640, S-435, AZD7706; 16) PPARδ agonists such as GW501516, GW590735; 17) triglyceride synthesis inhibitors; 18) MTTP inhibitors such as LAB687, CP346086; 19) low-density lipoprotein; 20) squalane epoxidase inhibitors; 21) platelet agglutination inhibitors; 22) 5-lipoxygenase activation protein inhibitors such as MK-591.

The "therapeutical medicines for hypertension" include, for example 1) diuretics such as thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone; 2) β-adrenaline blockers such as acebutolol, atenolol, betaxolol, bevantolol, bisoprolol, bopindolol, carteolol, carvedilol, celiprolol, esmolol, indeolol, metaprolol, nadolol, nebivolol, penbutolol, pindolol, probanolol, sotalol, tartatolol, tilisolol, timolol; 3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil; 4) angiotensin transferase inhibitors such as benazepril, captopril, cilazapril, delapril, enalapril, fosinopril, imidapril, rosinopril, moexipril, quinapril, quinapriril, ramipril, perindopril, perindropril, quanipril, spirapril, tenocapril, transolapril, zofenopril; 5) neutral endopeptidase inhibitors such as omapatrilat, cadoxatril, ecadotril, fosidotril, sampatrilat, AVE7688, ER4030; 6) endoserine antagonists such as tezosentan, A308165, YM62899; 7) vasodilators such as hydraladine, clonidine, minoxidil, nicotinyl alcohol; 8) angiotensin II antagonists such as candesartan, eporsartan, iribesartan, rosartan, pratosartan, tasosartan, telmisartan, balsartan, EXP-3137, F16828K, RNH6270; 9) α/β adrenalin blockers such as nipradiol, arotinolol, amoslalol; 10) α1 blockers such as terazosin, urapidil, purazosin, bunazosin, trimazosin, doxazosin, naphthopidil, indolamin, WHIP164, XEN010; 11) α2 agonists such as lofexidine, tiamenidine, moxonidine, rilmenidine, guanobenz; 12) aldosterone inhibitors.

The "anti-obesity medicines" include, for example 1) 5HT (serotonin) transporter inhibitors such as paraxetine, fluoxetine, fenfluramine, fluvoxamine, sertraline, imipulamin; 2) norepinephrine transporter inhibitors such as GW320659, decipulamin, talsupram, nomifensin; 3) cannabinoid-1 receptor 1 (CB-1) antabonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/370621, WO00/10967, WO00/10968, WO97/29079, WO99/02499, WO01/58869, WO02/076949, WO01/64632, WO01/64633, WO01/64634, WO03/006007, WO03/007887, EP-658546; 4) glerin antagonists such as compounds disclosed in WO01/87355, WO02/08250; 5) histamine(H3) antagonists/inverse-agonists such as thioperamide, 3-(1H-imidazol-4-yl)propyl-N-(pentenyl)carbonate, clobenpropit, iodofenpropit, imoproxyfen, GT2395, A331440, compounds disclosed in WO02/15905, O-[3-(1H-imidazo4-yl)propanol]carbamate, piperazine-containing H3-receptor antagonists (Lazewska, D. et al., *Phrmazie*, 56: 927-32 (2001), benzophenone derivatives Sasse, A. et al., *Arch. Pharm.* (Weinheim) 334: 45-52 (2001)), substituted N-phenylcarbamates (Reidemeister, S. et al., *Pharmazie*, 55: 83-6 (2000)), proxyfen derivatives (Sasse, A. et al., *J. Med. Chem.*, 43: 3335-43 (2000)); 6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A-2001-226269; 7) MCH-2R agonists/antagonists; 8) NPY1 antagonists such as isopropyl 3-chloro-5-(1-(6-[2-(5-ethyl-4-methyl-thiazol-2-yl)ethyl]-4-morpholinyl-4-yl-pyridin-2-ylamino)-ethyl)phenyl]carbamate, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528; 9) NPY2 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120526A, SR-120819A, JCF-104, H409/22, and other compounds disclosed in U.S. Pat. Nos. 6,140,354, 6,191,160, 6,258,837, 6,313,298, 6,337,332, 6,329,395, 6,340,683, 6,326,375, 6,329,395, 6,337,332, 6,335,345, EP-01010691, EP-01044970, WO97/19682, WO097/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., *J. Med. Chem.*, 43: 4288-4312 (2000); 10) reptins such as human recombinant reptin (PEG-OB, Hoffman La Roche), recombinant methionylreptin (Amgen); 11) reptin derivatives such as compounds disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519, WO96/23520; 12) opioid antagonists such as narmefen (Revex®), 3-methoxynartorexon, naroquison, narthoxon, compounds disclosed in WO00/21509; 13) aurexin antagonists such as SB-334867A, and other compounds disclosed in WO01/96302, WO01/68609, WO02/51232, WO02/51838, and WO03/023561; 14) bombesin receptor subtype-3 agonists; 15) cholecistokinin A (CCK-A) agonists such as AR-R15849, GI-181771, JMV-180, A-71378, A-71623, SR-146131, compounds described in U.S. Pat. No. 5,739,106; 16) CNTF (ciliary neurotrophic factors) such as GI-181771 (Glaxo-Smith Kline), SR146131 (Sanofi Synthelabo), butabindide, PD170,292, PS149164 (Pfizer); 17) CNTF derivatives such as axokine (Regeneron), and other compounds disclosed in WO94/09134, WO98/22128, WO99/43813; 18) growth hormone secretion receptor agonists such as NN703, hexarelin, MK-0677, SM-130686, CO-424,391, L-692,429, L-163,255, and compounds disclosed in U.S. Pat. No. 6,358,951, US Patent Application Nos. 2002/049196, 2002/022637, WO01/56592, WO02/32888; 19) serotonin receptor-2C agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457; 20) melanocholtin-3 receptor agonists; 21) melanocholtin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847; 22) monoamine reabsorption inhibitors such as cibtramin (Meridia®/Recuctil®) and its salts, and other derivatives disclosed in U.S. Pat. Nos. 4,746,680, 4,806,570, 5,436,272, US Patent Application No. 2002/0006964, WO01/27068, WO01/62341; 23) serotonin re-uptake inhibitors such as dexfenfluramine, fluoxetine, and other compounds disclosed in U.S. Pat. No. 6,365,633, WO01/27060, WO01/162341; 24) glucagon-like peptide-1 agonists; 25) topiramate (Topimax®); 26) phytopharm compound 57 (e.g., CP644,673); 27) acetyl CoA carboxylase-2 (ACC2) inhibitors; 28) β-adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. Nos. 5,705,515, 5,451,677, WO01/74782, WO02/32897; 29) diacylglycerol acyltransferase-1 inhibitors; 30) diacylglycerol acyltransferase-2 inhibitors, 31) fatty acid synthesis inhibitors such as carulenin, C75; 32) phosphodiesterase inhibitors such as theofylline, pentoxifylline zaprinast, sildenafil, amrinone, milrinone, cilostamide, rolipram, cilomilast; 32) thyroid hormone-β agonists such as KB-2611 (KaroBioBMS), and other compounds disclosed in WO02/15845, JP-A 2000-256190; 33) phytanic acids such as phytanic acid, 4-[(E)-2-(5,6,7,8-tetrahydro-5,5,8,8-tetramethyl-2-naphthalenyl-1-propenyl]benzoic acid (TTNPB), retinoic acid, and other compounds disclosed in WO99/00123; 34) acylestrogens such as oleoylestrone, and other compounds disclosed in del Mar-Grasa, M. et al., *Obesity Research*, 9:202-9 (2001); 35) glucocorticoid antagonists; 36) 11-β hydroxysteroid dehydrogenase-1 inhibitors such as BVT3498, BVT2733, and other compounds disclosed in WO01/90091, WO01/90090, WO01/90092; 37) stearoyl-CoA desaturase-1 inhibitors; 38) dipeptidyl peptidase-IV inhibitors such as isoleucine thiazolidine, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180, WO03/000181; 39) lipase inhibitors such as tetrahydrolitatin (Orlistat/Xenical®), Triton WR1339, RHC80267, lipstatin, teasaponin, diethylumbelliferyl phosphate, FL-386, WAY-121898, Bay-N-3176, valilactone, esteracin, evelactone A, evelactone B, RHC80267, and other compounds disclosed in WO01/77094, U.S. Pat. Nos. 4,598,089, 4,452,813, 5,512,565, 5,391,571, 5,602,151, 4,405,644, 4,189,438, 4,242,453; 39) fatty acid transporter inhibitors; 40) dicarboxylate transporter inhibitors; 41) glucose transporter inhibitors; 42) phosphate transporter inhibitors.

The combined pharmaceutical agents may be obtained by combining a compound of the invention and one or more of the above-mentioned co-agents. The combined pharmaceutical agents are useful for prevention and treatment of metabolic disorders, when combined with one or more medicines selected from a group consisting of medicines of diabetes and medicines for hyperlipemia. In particular, the combined pharmaceutical agents that comprise a medicine for hypertension and an anti-obesity medicine and contain a medicine for diabetes and/or a medicine for hyperlipemia added thereto are useful for prevention and treatment of metabolic disorders owing to the synergistic effects of the ingredients therein.

When the compounds of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Any ordinary physicians, veterinarians and clinicians may readily determine the effective dose necessary for retarding, inhibiting or stopping the disease development, and may suitably treat patients.

BEST MODE FOR CARRYING OUT THE INVENTION

The invention is described more concretely with reference to Examples and Reference Examples mentioned below, which, however, do not restrict the invention.

FORMULATION EXAMPLE 1

10 parts of the compound of Production Example 1, 15 parts by weight of heavy magnesium oxide and 75 parts by weight of lactose were uniformly mixed to prepare a powdery or granular preparation having a particle size of at most 350 μm. The preparation was encapsulated to give capsules.

FORMULATION EXAMPLE 2

45 parts of the compound of Production Example 1, 15 parts of starch, 16 parts of lactose, 21 parts of crystalline cellulose, 3 parts of polyvinyl alcohol and 30 parts of distilled water were uniformly mixed, then ground, granulated and dried, and then sieved to give a granular preparation having a particle diameter of from 1410 to 177 μm.

FORMULATION EXAMPLE 3

A granular preparation was prepared in the same manner as in Formulation Example 2. 96 parts of the granular preparation was mixed with 3 parts of calcium stearate, and shaped under compression into tablets having a diameter of 10 mm.

FORMULATION EXAMPLE 4

90 parts of the granular preparation obtained according to the method of Formulation Example 2 was mixed with 10 parts of crystalline cellulose and 3 parts of calcium stearate, and shaped under compression into tablets having a diameter of 8 mm. These were coated with a mixed suspension of syrup gelatin and precipitated calcium carbonate to give sugar-coated tablets.

For thin-layer chromatography in Examples, used was a plate of Silicagel $60F_{245}$ (Merck); and for detection, used was a UV detector. Wakogel C-300 (Wako Pure Chemicals) was used for the column silica gel; and LC-SORB SP-B-ODS (Chemco) or YMC-GEL ODS-AQ 120-S50 (Yamamura Chemical Laboratories) was for the reversed-phase column silica gel. Mass spectrum was determined according to an electrospray ionization (ESI) process, using QuattroII (Micromass).

Abbreviations in Examples have the following meanings.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
$CDCl_3$: heavy chloroform
$CD_3OD$: heavy methanol
DMSO-$d_6$: heavy dimethylsulfoxide Abbreviations in nuclear magnetic resonance spectrum have the following meanings:
  s: singlet
  d: doublet
  dd: double doublet
  t: triplet
  m: multiplet
  br: broad
  q: quartet
  J: coupling constant
  Hz: hertz Example 1:

Production of 2-(1-cyclopentylpiperidin-4-yloxy)-5-(4-cyanophenyl)pyrimidine

1) Production of 2-(1-t-butoxycarbonylpiperidin-4-yloxy)-5-bromopyrimidine:

1-t-butoxycarbonyl-4-hydroxypiperidine (408 mg, 2.03 mmol) and cesium carbonate (764 mg, 2.34 mmol) were added to a DMF solution (10 ml) of 2-chloro-5-bromopyrimidine (300 mg, 1.56 mmol), and stirred at room temperature for 14 hours. Water was added to the reaction mixture, and extracted with ethyl acetate. The organic layer was washed with saturated saline, dried with anhydrous sodium sulfate, and concentrated under reduced pressure. The residue was purified through silica gel column chromatography (C-300, hexane:ethyl acetate=10:1) to obtain the entitled compound (268 mg, 48%).

2) Production of 2-(1-t-butoxycarbonylpiperidin-4-yloxy)-5-(4-cyanophenyl)pyrimidine:

2-dimethoxyethane (2.0 ml) and aqueous 2 N sodium carbonate solution (0.7 ml) were added to 2-(1-t-butoxycarbonylpiperidin-4-yloxy)-5-bromopyrimidine (149 mg, 0.42 mmol), and then 4-cyanoboric acid (75.2 mg, 0.51 mmol) and tetrakis(triphenylphosphine)palladium(0) (10 mg, 0.0087 mmol) were added thereto and stirred in a nitrogen atmosphere at 90° C. for 3 hours. The reaction mixture was cooled to room temperature, and extracted with ethyl acetate. The organic layer was washed with saturated saline, dried with anhydrous sodium sulfate and concentrated under reduced pressure. The residue was purified through silica gel column chromatography (C-300, hexane:ethyl acetate=3:1) to obtain the entitled compound (122 mg, 77%).

3) Production of 2-(piperidin-4-yloxy)-5-(4-cyanophenyl)pyrimidine:

Trifluoroacetic acid (1.5 ml) was added to a methylene chloride solution (2.0 ml) of 2-(1-t-butoxycarbonylpiperidin-4-yloxy)-5-(4-cyanophenyl)pyrimidine (122 mg, 0.32 mmol) at room temperature, and stirred for 2.5 hours at the temperature. The reaction solution was concentrated under reduced pressure, and the residue was extracted with chloroform. The organic layer was washed with aqueous saturated sodium bicarbonate solution and saturated saline solution in that order, dried with anhydrous sodium sulfate, and concentrated under reduced pressure to obtain the entitled compound (90 mg, 100%).

4) Cyclopentanone (0.022 mol) and 0.3 N zinc chloride-sodium borocyanide solution (0.55 ml) were added to a methanol solution (3.0 ml) of 2-(piperidin-4-yloxy)-5-(4-cyanophenyl)pyrimidine (46 mg, 0.16 mmol), and stirred at room temperature for 14 hours. The reaction mixture was concentrated under reduced pressure, and the residue was extracted with chloroform. The organic layer was washed with saturated saline solution, dried with anhydrous sodium sulfate, and concentrated under reduced pressure. The resulting residue was purified through partitioning thin-layer chromatography (chloroform:methanol=10:1) to obtain the entitled compound (50 mg, 87%).

$^1$HNMR (300 MHz, CDCl$_3$, δ ppm): 1.38-1.78 (6H, m), 1.82-2.04 (4H, m), 2.08-2.21 (2H, m), 2.32-2.63 (3H, m), 2.74-2.96 (2H, m), 5.07-5.18 (1H, m), 7.62 (2H, d, J=8.6 Hz), 7.78 (1H, d, J=8.6 Hz), 8.73 (2H, s); mass spectrum (ESI): 349 (M+H)

Example 2:

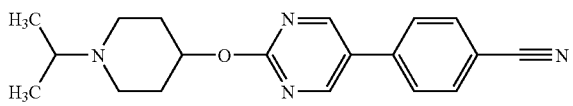

Production of 2-(1-isopropylpiperidin-4-yloxy)-5-(4-cyanophenyl)pyrimidine

According to the same method as in Example 1, the entitled compound was obtained.

$^1$HNMR (300 MHz, CDCl$_3$, δ ppm): 1.10 (6H, d, J=6.5 Hz), 1.88-2.05 (2H, m), 2.10-2.23 (2H, m), 2.43-2.60 (2H, m), 2.75-7.96 (3H, m), 5.08-5.20 (1H, m), 7.64 (2H, d, J=8.5 Hz), 7.78 (2H, d, J=8.5 Hz), 8.77 (2H, s); mass spectrum (ESI): 323 (M+H)

Example 3:

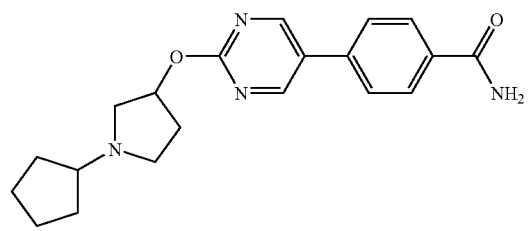

Production of 2-(1-cyclopentylpyrrolidin-3-yloxy)-5-(4-carbamoylphenyl)pyrimidine 1) Production of 2-(1-t-butoxycarbonylpyrrolidin-3-yloxy)-5-bromopyrimidine:

According to the same method as in Example 1-1) but using 1-t-butoxycarbonyl-3-hydroxypyrrolidine and 2-chloro-5-bromopyrimidine, the entitled compound was obtained.

2) According to the same method as in Example 1-2), 3) and 4) but using 2-(1-t-butoxycarbonylpyrrolidin-3-yloxy)-5-bromopyrimidine and 4-carbamoylphenylboronic acid, the entitled compound was obtained.

$^1$HNMR (400 MHz, CDCl$_3$, δ ppm): 1.34-1.56 (4H, m), 1.57-1.67 (2H, m), 1.70-1.80 (2H, m), 1.82-1.92 (1H, m), 3.10-3.60 (6H, m), 5.35-5.42 (1H, m), 7.41 (1H, brs), 7.81 (2H, d, J=8.4 Hz), 7.96 (2H, d, J=8.4 Hz), 8.04 (1H, brs), 8.97 (2H, s); mass spectrum (ESI): 353 (M+H)

Example 4:

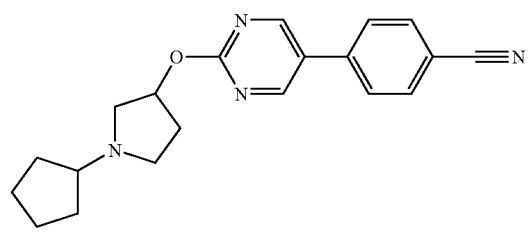

Production of 2-(1-cyclopentylpyrolidin-3-yloxy)-5-(4-cyanophenyl)pyrimidine

According to the same method as in Example 3, the entitled compound was obtained.

$^1$HNMR (400 MHz, CDCl$_3$, δ ppm): 1.46-1.90 (8H, m), 2.03-2.13 (1H, m), 2.34-2.45 (1H, m), 2.52-2.65 (1H, m), 2.71-2.84 (3H, m), 3.22-3.34 (1H, m), 5.44-5.51 (1H, m), 7.62 (1H, d, J=8.4 Hz), 7.76 (2H, d, J=8.4 Hz), 8.71 (2H, s); mass spectrum (ESI): 335 (M+H)

Example 5:

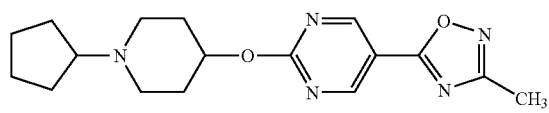

Production of 2-(1-cyclopentylpiperidin-4-yloxy)-5-{(3-methyl-1,2,4-oxadiazol-5-yl)pheny}pyrimidine According to the same method as in Example 1, the entitled compound was obtained.

$^1$HNMR (300 MHz, CDCl$_3$, δ ppm): 1.40-1.83 (6H, m), 1.83-2.25 (6H, m), 2.38-2.71 (3H, m), 2.50 (3H, s), 2.82-3.00 (2H, m), 5.12-5.30 (1H, m), 9.18 (2H, s); mass spectrum (ESI): 330 (M+H)

Example 6:

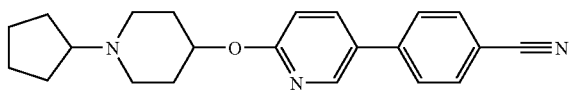

Production of 2-(1-cyclopentylpiperidin-4-yloxy)-5-(4-cyanophenyl)pyridine

1) Production of 2-fluoro-5-[4-cyanophenyl]pyridine:

According to the same method as in Example 1-2) but using 2-fluoro-5-bromopyridine and 4-cyanophenylboronic acid, the entitled compound was obtained.

2) 60% sodium hydride (13 mg) and 1-cyclopentyl-4-hydroxypiperidine (60 mg) were added to a DMF solution (3 ml) of 2-fluoro-5-[4-cyanophenyl]pyridine (56 mg), and stirred at 130° C. for 7 hours. The reaction mixture was cooled to room temperature, and water was added thereto and extracted with ethyl acetate. The organic layer was washed with saturated saline solution, dried with anhydrous magnesium sulfate, and concentrated under reduced pressure. The residue was purified through silica gel column chromatography (C-300, chloroform:methanol=9:1) to obtain the entitled compound.

$^1$HNMR (300 MHz, CDCl$_3$, δ ppm): 1.43-1.72 (6H, m), 1.81-1.92 (4H, m), 2.11-2.13 (2H, m), 2.44-2.66 (3H, m), 2.88-2.95 (2H, m), 5.12-5.19 (1H, m), 6.83 (1H, d J=8.6 Hz), 7.62 (2H, d, J=8.1 Hz), 7.72-7.81 (3H, m), 8.37 (1H, d, J=1.9 Hz); mass spectrum (ESI): 348 (M+H)

Example 7:

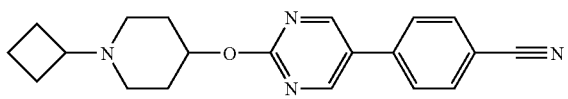

Production of 2-(1-cyclobutylpiperidin-4-yloxy)-5-(4-cyanophenyl)pyrimidine

According to the same method as in Example 1, the entitled compound was obtained.

$^1$HNMR (300 MHz, DMSO-d$_6$, δ ppm): 1.53-1.85 (6H, m), 1.90-2.09 (6H, m), 2.55-2.78 (3H, m), 4.95-5.05 (1H, m), 7.95 (4H, s), 9.01 (2H, s); mass spectrum (ESI): 335 (M+H)

Example 8:

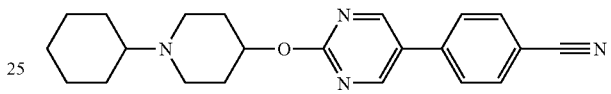

Production of 2-(1-cyclohexylpiperidin-4-yloxy)-5-(4-cyanophenyl)pyrimidine

According to the same method as in Example 1, the entitled compound was obtained.

$^1$HNMR (300 MHz, DMSO-d$_6$, δ ppm): 1.15-1.29 (6H, m), 1.60-1.83 (6H, m), 1.97-2.09 (2H, m), 2.25-2.53 (3H, m), 2.77-2.89 (2H, m), 4.95-5.05 (1H, m), 7.96 (2H, s), 9.02 (2H, s); mass spectrum (ESI): 363 (M+H)

Example 9:

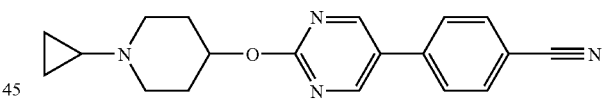

Production of 2-(1-cyclopropylpiperidin-4-yloxy)-5-(4-cyanophenyl)pyrimidine

According to the same method as in Example 1, the entitled compound was obtained.

$^1$HNMR (300 MHz, DMSO-d$_6$, δ ppm): 0.28-0.32 (2H, m), 0.39-0.47 (2H, m), 1.60-1.73 (3H, m), 1.92-2.04 (2H, m), 2.38-2.52 (2H, m), 2.79-2.90 (2H, m), 4.98-5.09 (1H, m), 7.96 (4H, s), 9.01 (2H, s); mass spectrum (ESI): 321 (M+H)

Example 10:

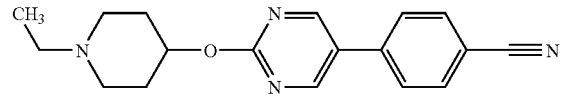

Production of 2-(1-ethylpiperidin-4-yloxy)-5-(4-cyanophenyl)pyrimidine

According to the same method as in Example 1, the entitled compound was obtained.

$^1$HNMR (300 MHz, DMSO-d$_6$, δ ppm): 1.00 (3H, t, J=7.2 Hz), 1.64-1.76 (2H, m), 1.96-2.08 (2H, m), 2.12-2.24 (2H, m), 2.34 (2H, d, J=7.2 Hz), 2.69-2.80 (2H, m), 4.96-5.08 (1H, m), 7.96 (4H, s), 9.01 (2H, s); mass spectrum (ESI): 309 (M+H)

Example 11:

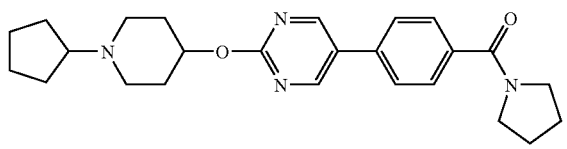

Production of 2-(1-cyclopentylpiperidin-4-yloxy)-5-{4-(pyrrolidin-1-ylcarbonyl)phenyl}pyrimidine 1) Production of 2-(1-cyclopentylpiperidin-4-yloxy)-5-bromopyrimidine:

According to the same reaction process as in Example 1-1) but using 2-chloro-5-bromopyrimidine and 4-hydroxy-1-cyclopentylpiperidine, the entitled compound was obtained.

2) 1,2-dimethoxyethane (3.0 ml) and aqueous 2 N sodium carbonate solution (1.0 ml) were added to 2-(1-cyclopentylpiperidin-4-yloxy)-5-bromopyrimidine (176 mg, 0.54 mmol), and then 4-(pyrrolidin-1-ylcarbonyl)phenylboronic acid (142 mg, 0.065 mmol) and tetrakis(triphenylphosphine)palladium(0) (30 mg, 0.026 mmol) were added thereto and stirred in a nitrogen atmosphere at 80° C. for 20 hours. The reaction mixture was cooled to room temperature, and water was added to it and extracted with ethyl acetate. The organic layer was washed with saturated saline solution, dried with anhydrous magnesium sulfate, and concentrated under reduced pressure. The residue was purified through silica gel column chromatography (C-200, chloroform:methanol=10:1) to obtain the entitled compound (130 mg, 57%).

$^1$HNMR (300 MHz, CDCl$_3$, δ ppm): 1.35-2.08 (14H, m), 2.08-2.25 (2H, m), 2.35-2.69 (2H, m), 2.82-2.98 (2H, m), 3.42-3.53 (2H, m), 3.60-3.72 (2H, m), 5.06-5.18 (1H, m), 7.55 (2H, d, J=8.3 Hz), 7.64 (2H, d, J=8.3 Hz), 8.71 (2H, s); mass spectrum (ESI): 421 (M+H)

Example 12:

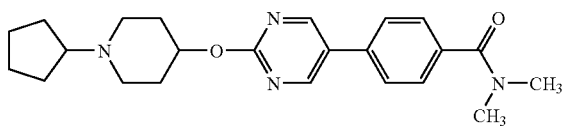

Production of 2-(1-cyclopentylpiperidin-4-yloxy)-5-{4-(dimethylcarbamoyl)phenyl}pyrimidine According to the same method as in Example 11, the entitled compound was obtained.

$^1$HNMR (300 MHz, CDCl$_3$, δ ppm): 1.45-2.72 (15H, m), 2.85-2.99 (1H, m), 3.04 (3H, brs), 3.14 (3H, brs), 5.08-5.22 (1H, m), 7.51-7.62 (4H, m), 8.72 (2H, s); mass spectrum (ESI): 395 (M+H)

Example 13:

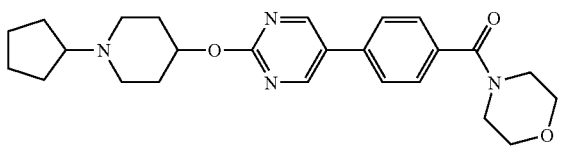

Production of 2-(1-cyclopentylpiperidin-4-yloxy)-5-{4-(morpholin-4-ylcarbonyl)phenyl}pyrimidine According to the same method as in Example 11, the entitled compound was obtained.

$^1$HNMR (300 MHz, CDCl$_3$, δ ppm): 1.35-1.81 (6H, m), 1.82-2.22 (6H, m), 2.29-2.65 (3H, m), 2.82-2.98 (2H, m), 3.37-3.99 )8H, m), 5.05-5.18 (1H, m), 7.53 (2H, d, J=8.2 Hz), 7.57 (2H, d, J=8.2 Hz), 8.71 (2H, s); mass spectrum (ESI): 437 (M+H)

Example 14:

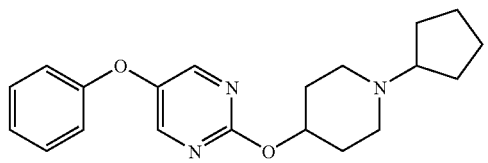

Production of 2-(1-cyclopentylpiperidin-4-yloxy)-5-{4-(phenoxy)phenyl}pyrimidine According to the same method as in Example 1, the entitled compound was obtained.

$^1$HNMR (400 MHz, CDCl$_3$, δ ppm): 1.50-1.80 (6H, m), 1.86-2.07 (4H, m), 2.16-2.28 (2H, m), 2.52-2.67 (3H, m), 2.89-3.01 (2H, m), 5.02-5.12 (1H, m), 6.93-7.00 (2H, m), 7.10-7.16 (2H, m), 7.30-7.38 (2H, m), 8.27 (2H, s); mass spectrum (ESI): 340 (M+H)

Example 15:

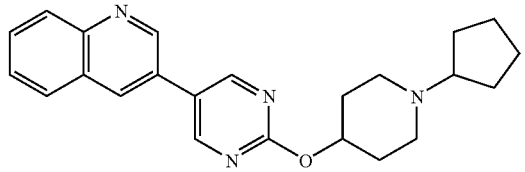

Production of 2-(1-cyclopentylpiperidin-4-yloxy)-5-{3-quinolinyl}pyrimidine

According to the same method as in Example 1 but using 3-quinolinylboronic acid in place of 4-cyanophenylboronic acid, the entitled compound was obtained.

$^1$HNMR (400 MHz, CDCl$_3$, δ ppm): 1.36-1.77 (6H, m), 1.81-2.04 (4H, m), 2.09-2.21 (2H, m), 2.33-2.47 (2H, m), 2.50-2.61 (1H, m), 2.84-2.97 (2H, m), 5.05-5.18 (1H, m), 7.57-7.63 (1H, m), 7.71-7.78 (1H, m), 7.88 (1H, d, J=8.1 Hz), 8.13 (1H, d J=8.4 Hz), 8.25 (1H, d, J=2.4 Hz), 8.82 (2H, s), 9.07 (1H, d, J=2.4 Hz); mass spectrum (ESI): 375 (M+H)

Example 16:

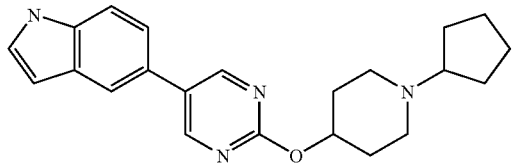

Production of 2-(1-cyclopentylpiperidin-4-yloxy)-5-{5-indolyl}pyrimidine

According to the same method as in Example 1 but using 5-indolylboronic acid in place of 4-cyanophenylboronic acid, the entitled compound was obtained.

$^1$HNMR (400 MHz, CDCl$_3$, δ ppm): 1.38-1.80 (6H, m), 1.82-2.06 (4H, m), 2.09-2.23 (2H, m), 2.33-2.65 (3H, m), 2.84-2.99 (2H, m), 5.05-5.18 (1H, m), 6.61 (1H, s), 7.22-7.36 (2H, m), 7.41-7.55 (1H, m), 7.75 (1H, s), 8.35-8.43 (1H, m), 8.72 (2H, s); mass spectrum (ESI): 363 (M+H)

Example 17:

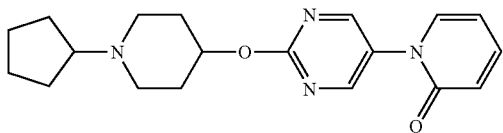

Production of 2-(1-cyclopentylpiperidin-4-yloxy)-5-(1H-pyridin-2-on-1-yl)pyrimidine Potassium carbonate (40 mg) and copper iodide (40 mg) were added to a DMF solution (5 ml) of 2-(1-cyclopentylpiperidin-4-yloxy)-5-bromopyrimidine (130 mg) and 1H-pyridin-2-one (19 mg), and stirred at 150° C. for 3 hours. The reaction mixture was cooled to room temperature, water was added to it and extracted with ethyl acetate. The organic layer was washed with saturated saline solution, dried with anhydrous magnesium sulfate, and concentrated under reduced pressure. The residue was purified through silica gel column chromatography (C-300, chloroform:methanol=9:1) to obtain the entitled compound (11 mg).

$^1$HNMR (300 MHz, DMSO-d$_6$, δ ppm): 1.23-1.84 (10H, m), 1.95-2.06 (2H, m), 2.18-2.28 (2H,m), 2.40-2.55 (1H, m), 2.71-2.82 (2H, m), 4.90-5.02 (1H, m), 6.36 (1H, t, J=7.0 Hz), 6.50 (1H, d, J=9.5 Hz), 7.50-7.59 (1H, m), 7.72 (1H, dt, J=2.0, 7.0 Hz), 8.69 (2H, s); mass spectrum (ESI): 341 (M+H)

Example 18:

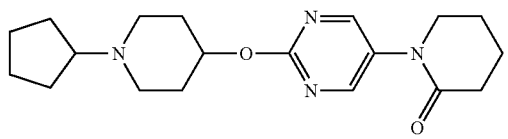

Production of 2-(1-cyclopentylpiperidin-4-yloxy)-5-(piperidin-2-on-1-yl)pyrimidine According to the same method as in Example 17 but using 2-(1-cyclopentylpiperidin-4-yloxy)-5-bromopyrimidine and piperidin-2-one, the entitled compound was obtained.

$^1$HNMR (300 MHz, DMSO-d$_6$, δ ppm): 1.20-2.50 (21H, m), 2.70-2.86 (2H, m), 3.58-3.64 (2H, m), 4.85-4.98 (1H, m), 8.53 (2H, s); mass spectrum (ESI): 345 (M+H)

Example 19:

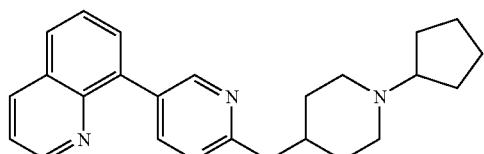

Production of 2-(1-cyclopentylpiperidin-4-yloxy)-5-{8-quinolinyl}pyrimidine

According to the same method as in Example 1 but using 8-quinolinylboronic acid in place of 4-cyanophenylboronic acid, the entitled compound was obtained.

$^1$HNMR (400 MHz, CDCl$_3$, δ ppm): 1.38-1.76 (6H, m), 1.85-2.05 (4H, m), 2.10-2.19 (2H, m), 2.34-2.45 (2H, m), 2.49-2.59 (1H, m), 2.83-2.94 (2H, m), 5.10-5.18 (1H, m), 7.45 (1H, dd, J=4.0, 8.1 Hz), 7.62 (1H, dd, J=7.3, 8.1 Hz), 7.72 (1H, dd, J=1.5, 7.0 Hz), 7.86 (1H, dd, J=1.5, 8.1 Hz), 8.21 (1H, dd, J=1.8, 8.1 Hz), 8.86 (2H, s), 8.91 (1H, dd, J=1.8, 4.4 Hz); mass spectrum (ESI): 375 (M+H)

Example 20:

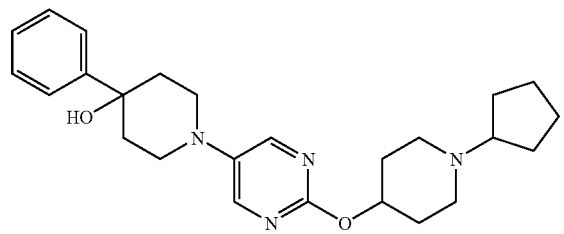

Production of 2-(1-cyclopentylpiperidin-4-yloxy)-5-(4-phenyl-4-hydroxypiperidin-1-yl)pyrimidine According to the same method as in Example 1 but using 2-(1-ccylopentylpiperidin-4-yloxy)-5-bromopyrimidine and 4-phenyl-4-hydroxypiperidine, the entitled compound was obtained.

¹HNMR (400 MHz, CDCl₃, δ ppm): 1.43-1.99 (12H, m), 2.06-2.17 (2H, m), 2.22-2.32 (2H, m), 2.39-2.65 (3H, m), 2.83-2.94 (2H, m), 3.19-3.28 (2H, m), 3.34-3.41 (2H, m), 4.94-5.02 (1H, m), 7.25-7.30 (1H, m), 7.34-7.40 (2H, m), 7.48-7.54 (2H, m), 8.23 (2H, m); mass spectrum (ESI): 423 (M+H)

Example 21:

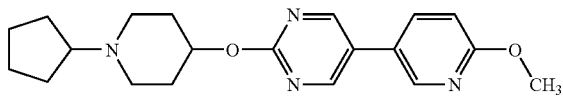

Production of 2-(1-cyclopentylpiperidin-4-yloxy)-5-(2-methoxypyridin-5-yl)pyrimidine According to the same method as in Example 1 but using 2-methoxypyridin-5-ylboronic acid in place of 4-cyanophenylboronic acid, the entitled compound was obtained.

¹HNMR (300 MHz, CDCl₃, δ ppm): 1.46-1.71 (6H, m), 1.85-2.03 (4H, m), 2.14-2.17 (2H, m), 2.45-2.62 (3H, m), 2.90-2.91 (2H, m), 2.90-2.91 (2H, m), 3.97 (3H, s). 5.10-5.11 (1H, m), 6.85 (1H, d, J=8.6 Hz), 7.69 (1H, dd, J=2.6, 8.6 Hz), 8.30 (1H, d, J=2.6 Hz), 8.63 (2H, s); mass spectrum (ESI): 355 (M+H)

Example 22:

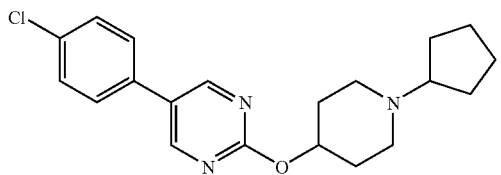

Production of 2-(1-cyclopentylpiperidin-4-yloxy)-5-(4-chlorophenyl)pyrimidine

According to the same method as in Example 1 but using 4-chlorophenylboronic acid in place of 4-cyanophenylboronic acid, the entitled compound was obtained.

¹HNMR (400 MHz, CDCl₃, δ ppm): 1.38-1.76 (6H, m), 1.84-2.01 (4H, m), 2.07-2.16 (2H, m), 2.32-2.44 (2H, m), 2.49-2.59 (1H, m), 2.82-2.93 (2H, m), 5.03-5.13 (1H, m), 7.43 (4H, s), 8.64 (2H, s); mass spectrum (ESI): 358 (M+H)

Example 23:

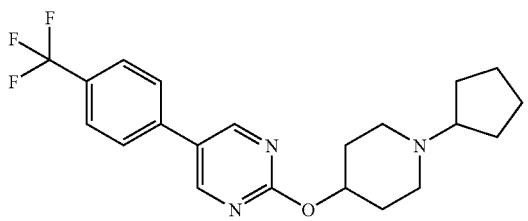

Production of 2-(1-cyclopentylpiperidin-4-yloxy)-5-(4-trifluoromethylphenyl)pyrimidine According to the same method as in Example 1 but using 4-(trifluoromethyl)phenylboronic acid in place of 4-cyanophenylboronic acid, the entitled compound was obtained.

¹HNMR (400 MHz, CDCl₃, δ ppm): 1.39-1.76 (6H, m), 1.84-2.03 (4H, m), 2.07-2.19 (2H, m), 2.33-2.47 (2H, m), 2.51-2.61 (1H, m), 2.83-2.94 (2H, m), 5.05-5.16 (1H, m), 7.61 (2H, d, J=8.1 Hz), 7.72 (2H, d, J=8.1 Hz), 8.70 (2H, s); mass spectrum (ESI): 392 (M+H)

Example 24:

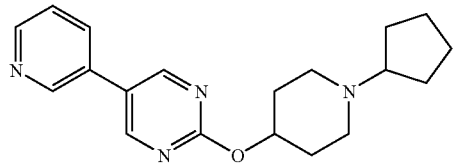

Production of 2-(1-cyclopentylpiperidin-4-yloxy)-5-(pyridin-3-yl)pyrimidine

According to the same method as in Example 1 but using 3-pyridylboronic acid in place of 4-cyanophenylboronic acid, the entitled compound was obtained.

¹HNMR (400 MHz, CDCl₃, δ ppm): 1.36-1.76 (6H, m), 1.84-2.01 (4H, m), 2.07-2.17 (2H, m), 2.31-2.43 (2H, m), 2.49-2.59 (1H, m), 2.83-2.94 (2H, m), 5.06-5.15 (1H, m), 7.37-7.43 (1H, m), 7.78-7.83 (1H, m) 8.61-8.66 (1H, m), 8.69 (2H, s), 8.75-8.80 (1H, m); mass spectrum (ESI): 325 (M+H)

Example 25:

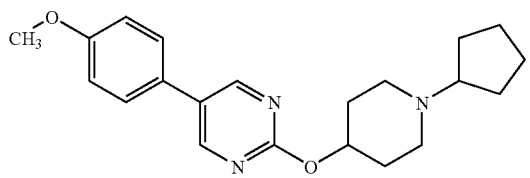

Production of 2-(1-cyclopentylpiperidin-4-yloxy)-5-(4-methoxyphenyl)pyrimidine

According to the same method as in Example 1 but using 4-methoxyphenylboronic acid in place of 4-cyanophenylboronic acid, the entitled compound was obtained.

¹HNMR (400 MHz, CDCl₃, δ ppm): 1.37-1.75 (6H, m), 1.84-2.00 (4H, m), 2.06-2.16 (2H, m), 2.32-2.43 (2H, m), 2.49-2.59 (1H, m), 2.82-2.93 (2H, m), 3.85 (3H, s), 5.02-5.10 (1H, m), 6.99 (2H, d, J=8.8 Hz), 7.42 (2H, d, J=8.8 Hz), 8.63 (2H, s); mass spectrum (ESI): 354 (M+H)

Example 26:

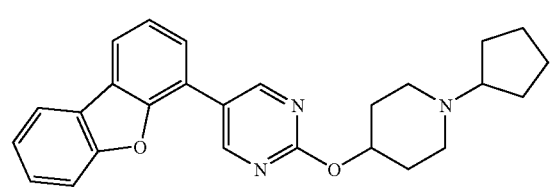

Production of 2-(1-cyclopentylpiperidin-4-yloxy)-5-(dibenzofuran-4-yl)pyrimidine According to the same method as in Example 1 but using dibenzofuran-4-ylboronic acid in place of 4-cyanophenylboronic acid, the entitled compound was obtained.

¹HNMR (400 MHz, CDCl₃, δ ppm): 1.38-1.77 (6H, m), 1.85-2.05 (4H, m), 2.11-2.21 (1H, m), 2.34-2.46 (2H, m), 2.51-2.61 (1H, m), 2.86-2.97 (2H, m), 5.10-5.20 (1H, m), 7.34-7.60 (5H, m), 7.94-8.00 (2H, m), 9.04 (2H, s); mass spectrum (ESI): 414 (M+H)

Example 27:

Production of 2-(1-cyclopentylpiperidin-4-yloxy)-5-(2-cyclopentyloxypyridin-5-yl)pyrimidine 1) Production of 2-(cyclopentylpiperidin-4-yloxy)-5-(2-benzyloxypyridin-5-yl)pyrimidine:

According to the same method as in Example 1-2) but using 2-benzyloxy-5-(4,4,5,5-tetramethyl-1,3,2-dioxaboroan-2-yl)pyridine and 2-(cyclopentylpiperidin-4-yloxy)-5-bromopyridine, the entitled compound was obtained.

2) Production of 2-(1-cyclopentylpiperidin-4-yloxy)-5-(1H-pyridin-2-on-5-yl)pyrimidine:

10% palladium-carbon (700 mg) was added to a methanol solution (30 ml) of 2-(cyclopentylpiperidin-4-yloxy)-5-(2-benzyloxypyridin-5-yl)pyrimidine (2.22 g), and stirred in a hydrogen atmosphere at room temperature for 3 hours. The reaction mixture was filtered to remove palladium-carbon, and the filtrate was concentrated under reduced pressure to obtain the entitled compound.

3) 60% sodium hydride (21 mg) and cyclopentyl bromide were added to a DMF solution (4 ml) of 2-(1-cyclopentylpiperidin-4-yloxy)-5-(1H-pyridin-2-on-5-yl)pyrimidine (120 mg), and stirred at room temperature for 2 hours. Water was added to the reaction mixture, and extracted with ethyl acetate. The organic layer was washed with saturated saline solution, dried with anhydrous magnesium sulfate, and concentrated under reduced pressure. The resulting residue was purified through silica gel column chromatography (chloroform:methanol=9:1) to obtain the entitled compound.

¹HNMR (300 MHz, CDCl₃, δ ppm): 1.47-2.17 (20H, m), 2.46-2.52 (3H, m), 2.89-2.92 (2H, m), 5.11-5.12 (1H, m), 5.40-5.44 (1H, m), 6.78 (1H, d, J=8.6 Hz), 7.68 (1H, dd, J=2.6, 8.6 Hz), 8.29 (1H, d, J=2.6 Hz), 8.63 (2H, s); mass spectrum (ESI): 409 (M+H)

Example 28:

Production of 2-(1-cyclopentylpiperidin-4-yloxy)-5-(1H-pyridin-2-on-5-yl)pyrimidine According to the same method as in Example 27, the entitled compound was obtained.

¹HNMR (300 MHz, CDCl₃, δ ppm): 1.43-1.76 (6H, m), 1.84-2.00 (4H, m), 2.11-2.17 (2H, m), 2.39-2.48 (2H, m), 2.56-2.61 (1H, m), 2.87-2.90 (2H, m), 5.07-5.10 (1H, m), 6.73 (1H, d, J=9.5 Hz), 7.55 (1H, d, J=2.2 Hz), 7.66 (1H, dd, J=2.3, 9.3 Hz), 8.56 (2H, s); mass spectrum (ESI): 341 (M+H)

Example 29:

Production of 2-(1-ccylopentylpiperidin-4-yloxy)-5-(1-cyclopentyl-1H-pyridin-2-on-3-yl)pyrimidine According to the same method as in Example 27, the entitled compound was obtained.

¹HNMR (300 MHz, CDCl₃, δ ppm): 1.42-1.99 (16H, m), 2.09-2.25 (4H, m), 2.42-2.59 (3H, m), 2.81-2.91 (2H, m), 5.08-5.11 (1H, m), 5.33-5.38 (1H, m), 6.31 (1H, t, J=6.9 Hz), 7.37-7.44 (2H, m), 8.83 (2H, s); mass spectrum (ESI): 409 (M+H)

Example 30:

Production of 2-(1-cyclopentylpiperidin-4-yloxy)-5-{2-(pyrrolidin-1-ylcarbonyl)pyridin-5-yl}pyrimidine According to the same method as in Example 11, the entitled compound was obtained.

¹HNMR (300 MHz, CDCl₃, δ ppm): 1.40-2.35 (16H, m), 2.35-2.75 (3H, m), 2.85-3.00 (2H, m), 3.66-3.75 (2H, m), 3.75-3.88 (2H, m), 5.08-5.22 (1H, m), 7.93 (2H, dd, J=2.2, 8.1 Hz), 8.00 (1H, d, J=8.1 Hz), 8.74 (2H, s), 8.75 (1H, d, J=2.2 Hz); mass spectrum (ESI): 422 (M+H)

Example 31:

Production of 2-(1-cyclopentylpiperidin-4-yloxy)-5-(2-cyano-5-thienyl)pyrimidine According to the same method as in Example 1, the entitled compound was obtained.
¹HNMR (400 MHz, CDCl₃, δ ppm): 1.38-1.78 (6H, m), 1.83-2.01 (4H, m), 2.07-2.18 (2H, m) 2.34-2.47 (2H, m), 2.51-2.62 (1H, m), 2.83-2.93 (2H, m), 5.06-5.14 (1H, m), 7.23 (1H, d, J=4.0 Hz), 7.62 (1H, d, J=4.0 Hz), 8.69 (2H, s); mass spectrum (ESI): 355 (M+H)

Example 32:

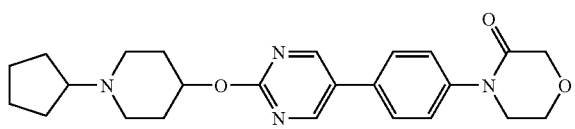

Production of 2-(1-cyclopentylpiperidin-4-yloxy)-5-{4-(morpholin-3-on-1-yl)phenyl}pyrimidine 1) Production of 5-(4-aminophenyl)-2-(1-t-butoxycarbonylpiperidin-4-yloxy)pyrimidine:
According to the same method as in Example 1-2) but using 2-(1-t-butoxycarbonylpiperidin-4-yloxy)-5-bromopyrimidine and 4-(4,4,5,5-tetramethyl-1,3,2-dioxobororan-2-yl)aniline, the entitled compound was obtained.
2) Production of 2-(1-t-butoxycarbonylpiperidin-4-yloxy)-5-{4-(morpholin-3-on-1-yl)phenyl}pyrimidine: 5-{4-(2-bromoacetylamino)phenyl}-2-(1-t-butoxycarbonylpiperidin-4-yloxy)pyrimidine readily obtained through reaction of 5-(4-aminophenyl)-2-(1-t-butoxycarbonylpiperidin-4-yloxy)pyrimidine and bromoacetyl bromide, was reacted with potassium t-butoxide to obtain the entitled compound.
3) According to the same method as in Example 1-3), 4) but using 2-(1-t-butoxycarbonylpiperidin-4-yloxy)-5-{4-(morpholin-3-on-1-yl)phenyl}pyrimidine, the entitled compound was obtained.
¹HNMR (300 MHz, CDCl₃, δ ppm): 1.38-2.08 (12H, m), 2.15-2.35 (1H, m), 2.48-2.82 (2H, m), 2.88-3.05 (2H, m), 3.76-3.85 (2H, m), 4.03-4.12 (2H, m), 4.38 (2H, s), 5.08-5.27 (1H, m), 7.47 (2H, d, J=8.5 Hz), 7.57 (2H, d, J=8.5 Hz), 8.70 (2H, s); mass spectrum (ESI): 423 (M+H)

Example 33:

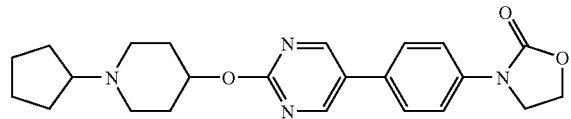

Production of 2-(1-cyclopentylpiperidin-4-yloxy)-5-{4-(2-oxazolidinon-3-yl)phenyl}pyrimidine According to the same method as in Example 32 but using (2-chloroethyl)chloroformate in place of 2-bromoacetyl bromide, the entitled compound was obtained.
¹HNMR (300 MHz, CDCl₃, δ ppm): 1.37-2.12 (12H, m), 2.12-2.33 (1H, m), 2.43-2.80 (2H, m), 2.85-3.03 (2H, m), 4.11 (2H, t, J=7.9 Hz), 4.54 (2H, t, J=7.9 Hz), 5.08-5.24 (1H, m), 7.53 (2H, d, J=8.4 Hz), 7.68 (2H, d, J=8.4 Hz), 8.69 (2H, s); mass spectrum (ESI): 409 (M+H)

Example 34:

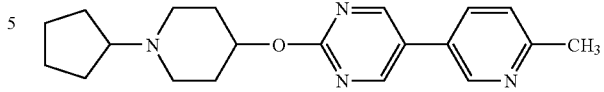

Production of 2-(1-cyclopentylpiperidin-4-yloxy)-5-(2-methyl-3-pyridin-5-yl)pyrimidine According to the same method as in Example 1 but using 2-methylpyridin-5-ylboronic acid in place of 4-cyanophenylboronic acid, the entitled compound was obtained.
¹HNMR (300 MHz, CDCl₃, δ ppm): 1.39-1.69 (6H, m), 1.83-2.00 (4H, m), 2.09-2.14 (2H, m), 2.33-2.40 (2H, m), 2.51-2.56 (1H, m), 2.61 (3H, s), 2.86-2.90 (2H, m), 5.07-5.10 (1H, m), 7.23-7.27 (1H, m), 7.70 (1H, dd, J=2.4, 8.0 Hz), 8.55-8.67 (3H, m); mass spectrum (ESI): 339 (M+H)

Example 35:

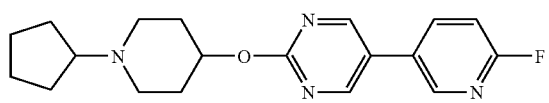

Production of 2-(1-cyclopentylpiperidin-4-yloxy)-5-(2-fluoro-3-pyridin-5-yl)pyrimidine According to the same method as in Example 1 but using 2-fluoro-5-(4,4,5,5-tetramethyl-1,3,2-dioxabororan-2-yl)pyridine in place of 4-cyanophenylboronic acid, the entitled compound was obtained.
¹HNMR (300 MHz, CDCl₃, δ ppm): 1.39-2.00 (10H, m), 2.09-2.15 (2H, m), 2.34-2.40 (2H, m), 2.52-2.57 (1H, m), 2.87-2.88 (2H, m), 5.08-5.13 (1H, m), 7.06 (1H, dd, J=3.0, 8.5 Hz), 7.92 (2H, dt, J=2.6, 8.4 Hz), 8.37 (1H, d, J=1.9 Hz), 8.56 (2H, s); mass spectrum (ESI): 343 (M+H)

Example 36:

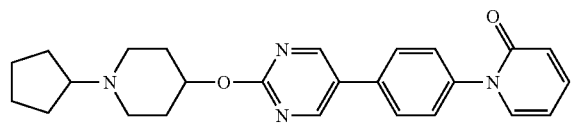

Production of 2-(1-cyclopentylpiperidin-4-yloxy)-5-{4-(1H-pyridin-2-on-1-yl)phenyl}pyrimidine According to the same method as in Example 1 but using 4-(1H-pyridin-2-on-1-yl)-1-(4,4,5,5-tetramethyl-1,3,2-dioxobororan-2-yl)benzene and 1-t-butoxycarbonylpiperidin-4-yloxy)-5-bromopyrimidine, the entitled compound was obtained.
¹HNMR (300 MHz, CDCl₃, δ ppm): 1.38-2.05 (10H, m), 2.05-2.23 (2H, m), 2.29-2.65 (2H, m), 2.81-3.00 (2H, m), 5.01-5.20 (1H, m), 6.29 (1H, t, J=6.7 Hz), 6.69 (1H, d, J=9.2 Hz), 7.32-7.48 (2H, m), 7.52 (2H, d, J=8.3 Hz), 7.64 (2H, d, J=8.3 Hz), 8.73 (2H, s); mass spectrum (ESI): 417 (M+H)

Example 37:

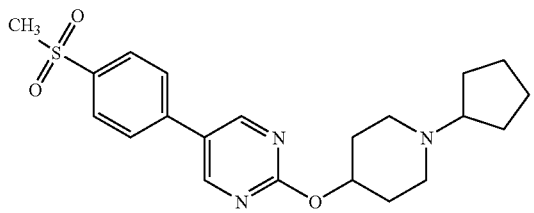

Production of 2-(1-cyclopentylpiperidin-4-yloxy)-5-{4-(methylsulfonyl)phenyl}pyrimidine According to the same method as in Example 1 but using 4-(methylsulfonyl)phenylboronic acid in place of 4-cyanophenylboronic acid, the entitled compound was obtained.

$^1$HNMR (400 MHz, CDCl$_3$, δ ppm): 1.38-1.77 (6H, m), 1.84-2.04 (4H, m), 2.08-2.19 (2H, m), 2.31-2.47 (2H, m), 2.50-2.61 (1H, m), 2.83-2.97 (2H, m), 5.06-5.16 (1H, m), 7.71 (2H, dd, J=2.2, 6.6 Hz), 8.05 (2H, dd, J=1.8, 6.6 Hz), 8.73 (2H, s); mass spectrum (ESI): 402 (M+H)

Example 38:

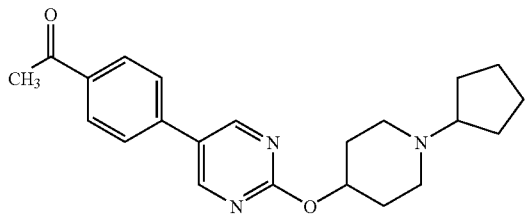

Production of 2-(1-cyclopentylpiperidin-4-yloxy)-5-{4-acetylphenyl}pyrimidine

According to the same method as in Example 1 but using 4-acetylphenylboronic acid in place of 4-cyanophenylboronic acid, the entitled compound was obtained.

$^1$HNMR (400 MHz, CDCl$_3$, δ ppm): 1.38-1.76 (6H, m), 1.84-2.02 (4H, m), 2.07-2.17 (2H, m), 2.32-2.44 (2H, m), 2.49-2.60 (1H, m), 2.64 (3H, s), 2.83-2.94 (2H, m), 5.06-5.15 (1H, m), 7.61 (2H, d, J=8.1 Hz), 8.05 (2H, d, J=8.1 Hz), 8.73 (2H, s); mass spectrum (ESI): 366 (M+H)

Example 39:

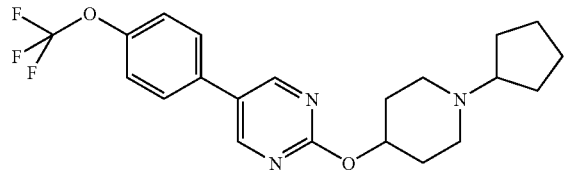

Production of 2-(1-cyclopentylpiperidin-4-yloxy)-5-(4-trifluoromethoxyphenyl)pyrimidine According to the same method as in Example 1 but using 4-(trifluoromethoxy)phenylboronic acid in place of 4-cyanophenylboronic acid, the entitled compound was obtained.

$^1$HNMR (400 MHz, CDCl$_3$, δ ppm): 1.38-1.76 (6H, m), 1.83-2.01 (4H, m), 2.03-2.17 (2H, m), 2.31-2.44 (2H, m), 2.49-2.59 (1H, m), 2.81-2.93 (2H, m), 5.05-5.14 (1H, m), 7.32 (2H, d, J=8.8 Hz), 7.51 (2H, d, J=8.8 Hz), 8.65 (2H, s); mass spectrum (ESI): 408 (M+H)

Example 40:

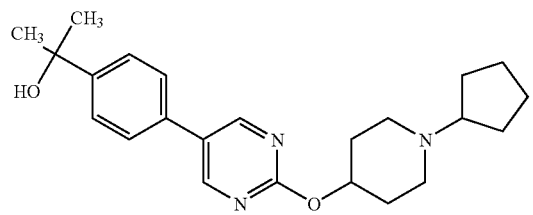

Production of 2-(1-cyclopentylpiperidin-4-yloxy)-5-{4-(2-hydroxy-2-propyl)phenyl}pyrimidine According to the same method as in Example 1, the entitled compound was obtained.

$^1$HNMR (400 MHz, CDCl$_3$, δ ppm): 1.38-1.77 (6H, m), 1.83-2.07 (4H, m), 2.07-2.18 (2H, m), 2.34-2.47 (2H, m), 2.51-2.61 (1H, m), 2.82-2.96 (2H, m), 5.03-5.16 (1H, m), 7.47 (2H, dd, J=2.2, 6.6 Hz), 7.59 (2H, dd, J=2.2, 6.6 Hz), 8.67 (2H, s); mass spectrum (ESI): 382 (M+H)

Example 41:

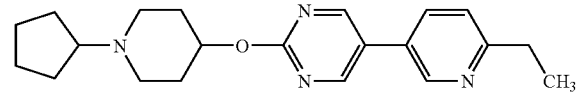

Production of 2-(1-cyclopentylpiperidin-4-yloxy)-5-(2-ethyl-5-pyridyl)pyrimidine According to the same method as in Example 1 but using 2-ethyl-5-(4,4,5,5-tetramethyl-1,3,2-dioxabororan-2-yl)pyridine acid in place of 4-cyanophenylboronic acid, the entitled compound was obtained.

$^1$HNMR (300 MHz, CDCl$_3$, δ ppm): 1.31-1.69 (9H, m), 1.84-2.00 (4H, m), 2.09-2.14 (2H, m), 2.33-2.37 (2H, m), 2.51-2.57 (1H, m), 2.85-2.92 (4H, m), 5.08-5.11 (1H, m), 7.26-7.29 (1H, m), 7.73 (2H, dd, J=2.4, 8.1 Hz), 8.67-8.68 (3H, m); mass spectrum (ESI): 353 (M+H)

Example 42:

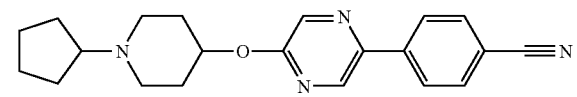

Production of 2-(1-cyclopentylpiperidin-4-yloxy)-5-(4-cyanophenyl)pyrazine

1) Production of 2-(1-t-butoxycabonylpiperidin-4-yloxy)-5-bromopyrazine:

Cesium carbonate (372 mg) was added to a DMF solution (2 ml) of 2-bromo-5-hydroxypyrazine (100 mg) and 1-t-butoxycarbonyl-4-(methanesulfonyloxy)piperidine (192 mg), and stirred at 90° C. for 14 hours. The reaction mixture was cooled to room temperature, water was added thereto and extracted with ethyl acetate. The organic layer was washed with saturated saline solution, dried with anhydrous magnesium sulfate, and concentrated under reduced pressure. The residue was purified through silica gel column chromatography (C-300, hexane:ethyl acetate=1:11) to obtain the entitled compound (198 mg).

2) According to the same method as in Example 1-2), 3), 4) but using 2-(1-t-butoxycabonylpiperidin-4-yloxy)-5-bromopyrazine and 4-cyanophenylboronic acid, the entitled compound was obtained.
$^1$HNMR (300 MHz, CDCl$_3$, δ ppm): 1.42-1.62 (4H, m), 1.67-1.94 (6H, m), 2.08-2.13 (2H, m), 2.33-2.39 (2H, m), 2.52-2.57 (1H, m), 2.85-2.88 (2H, m), 5.09-5.12 (1H, m), 7.75 (2H, d, J=8.7 Hz), 8.03 (2H, d, J=8.7 Hz), 8.27 (1H, d, J=1.4 Hz), 8.52 (1H, d, J=1.4 Hz); mass spectrum (ESI): 349 (M+H)

Example 43:

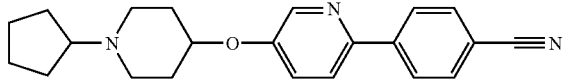

Production of 5-(1-cyclopentylpiperidin-4-yloxy)-2-(4-cyanophenyl)pyridine

1) Production of 2-(4-cyanophenyl)-2-bromopyridine:
According to the same method as in Example 42 but using 2-bromo-5-hydroxypyridine and 1-t-butoxycarbonyl-4-(methanesulfonyloxy)piperidine, the entitled compound was obtained.

2) According to the same method as in Example 1-2), 3), 4) but using 2-(4-cyanophenyl)-2-bromopyridine and 4-cyanophenylboronic acid, the entitled compound was obtained.
$^1$HNMR (300 MHz, CDCl$_3$, δ ppm): 1.39-1.73 (6H, m), 1.84-1.94 (4H, m), 2.03-2.10 (2H, m), 2.33-2.39 (2H, m), 2.52-2.57 (1H, m), 2.81-2.83 (2H, m), 4.41-4.44 (1H, m), 7.26-7.31 (1H, m), 7.68-7.74 (3H, m), 8.05 (2H, d, J=8.2 Hz), 8.40 (1H, d, J=2.9 Hz); mass spectrum (ESI): 348 (M+H)

Example 44:

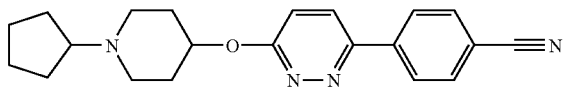

Production of 2-(1-cyclopentylpiperidin-4-yloxy)-5-(4-cyanophenyl)pyridazine

1) Production of 6-(4-cyanophenyl)-2H-pyridazin-3-one:
According to the method described in Synthesis (pp. 334-341, 1993) but using 4-cyanoacetophenone, the entitled compound was produced.

2) Production of 2-(1-t-butoxycarbonylpiperidin-4-yloxy)-5-(4-cyanophenyl)pyridazine:
Cesium carbonate (1.65 g) was added to a DMF solution (10 ml) of 6-(4-cyanophenyl)-2H-pyridazin-3-one (500 mg) and 1-t-butoxycarbonyl-4-(methanesulfonyloxy)piperidine (850 mg), and stirred at 105° C. for 4 hours. The reaction mixture was cooled to room temperature, and water was added thereto and extracted with ethyl acetate. The organic layer was washed with saturated saline solution, dried with anhydrous magnesium sulfate, and concentrated under reduced pressure. The residue was purified through silica gel column chromatography (C-200, hexane:ethyl acetate=7:3) to obtain the entitled compound (204 mg).

3) According to the same method as in Example 1-3), 4) but using 2-(1-t-butoxycarbonylpiperidin-4-yloxy)-5-(4-cyanophenyl)pyridazine, the entitled compound was obtained.
$^1$HNMR (300 MHz, CDCl$_3$, δ ppm): 1.51-1.76 (6H, m), 1.88-2.04 (4H, m), 2.17-2.33 (2H, m), 2.48-2.72 (3H, m), 2.96-3.02 (2H, m), 5.42-5.46 (1H, m), 7.08 (1H, d, J=9.3 Hz), 7.78-7.84 (3H, m), 8.13 (1H, d, J=8.2 Hz); mass spectrum (ESI): 349 (M+H)

Example 45:

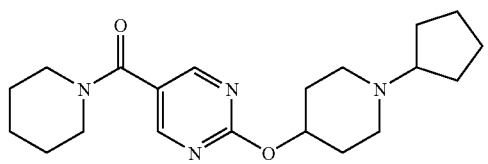

Production of 2-(1-cyclopentylpiperidin-4-yloxy)-5-(piperidin-1-ylcarbonyl)pyrimidine 1) Production of 2-(1-t-butoxycarbonylpiperidin-4-yloxy)-5-(phenoxycarbonyl)pyrimidine:
Palladium acetate (35 mg, 0.31 mmol), bis(diphenylphosphino)ferrocene (170 mg, 1.54 mmol), phenol (1.5 ml, 17.1 mmol), triethylamine (0.5 ml, 3.6 mmol) were added in that order to a toluene solution (1.0 ml) of 2-(1-t-butoxycarbonylpiperidin-4-yloxy)-5-bromopyridine (550 mg, 1.54 mmol), and stirred in a carbon monoxide atmosphere under normal pressure at 100° C. for 14 hours. The reaction mixture was cooled to room temperature, an aqueous saturated sodium bicarbonate solution was added thereto and extracted with ethyl acetate. The organic layer was washed with saturated saline solution, dried with anhydrous magnesium sulfate, and concentrated under reduced pressure. The residue was purified through silica gel column chromatography (C-200, hexane:ethyl acetate=7:3) to obtain the entitled compound (589 mg, 96%).

2) Production of 2-(1-t-butoxycarbonylpiperidin-4-yloxy)-5-(piperidin-1-carbonyl)pyrimidine:
Piperidine (0.02 ml, 0.20 mmol) was added to a dimethylformamide solution (1.0 ml) of 2-(1-t-butoxycarbonylpiperidin-4-yloxy)-5-(phenoxycarbonyl)pyrimidine (40 mg, 0.100 mmol), and stirred at room temperature for 12 hours. Water was added to the reaction mixture and extracted with ethyl acetate. The organic layer was washed with saturated saline solution, dried with anhydrous magnesium sulfate, and concentrated under reduced pressure. The residue was purified through partitioning thin-layer chromatography (hexane:ethyl acetate=3:7) to obtain the entitled compound (38 mg, 97%).

3) According to the same method as in Example 1-3), 4) but using 2-(1-t-butoxycarbonylpiperidin-4-yloxy)-5-(piperidin-1-carbonyl)pyrimidine (38 mg, 0.100 mmol), the entitled compound was obtained (17 mg, 43%).

¹HNMR (400 MHz, CDCl₃, δ ppm): 1.35-1.99 (20H, m), 2.03-2.15 (2H, m), 2.30-2.42 (2H, m), 2.48-2.58 (1H, m), 2.80-2.91 (2H, m), 5.02-5.14 (1H, m), 8.56 (2H, s); mass spectrum (ESI): 359 (M+H)

Example 46:

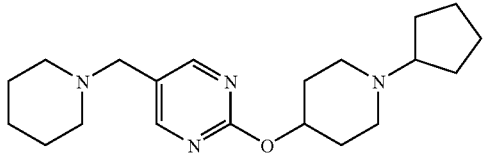

Production of 2-(1-ccylopentylpiperidin-4-yloxy)-5-(piperidin-1-ylmethyl)phenyl}pyrimidine The compound of Example 45 was reduced with aluminium lithium hydride and post-processed according to an ordinary method, and the resulting residue was purified through partitioning thin-layer chromatography (chloroform:methanol=10:1) to obtain the entitled compound (30 mg, 65%).

¹HNMR (400 MHz, CDCl₃, δ ppm): 1.33-2.12 (18H, m), 2.27-2.42 (6H, m), 2.46-2.57 (1H, m), 2.80-2.92 (2H, m), 3.36 (2H, s), 4.95-5.05 (1H, m), 8.37 (2H, s); mass spectrum (ESI): 345 (M+H)

Example 47:

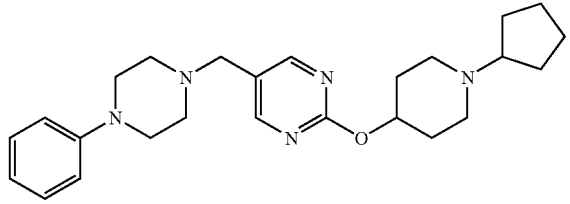

Production of 2-(1-cyclopentylpiperidin-4-yloxy)-5-(4-phenylpiperazin-1-ylmethyl)pyrimidine According to the same method as in Example 46, the entitled compound was obtained.

¹HNMR (400 MHz, CDCl₃, δ ppm): 1.37-1.97 (10H, m), 2.04-2.13 (2H, m), 2.31-2.42 (2H, m), 2.48-2.63 (5H, m), 2.81-2.91 (2H, m), 3.14-3.21 (4H, m), 3.47 (2H, s), 4.98-5.08 (1H, m), 6.80-6.92 (3H, m), 7.20-7.27 (2H, m), 8.43 (2H, s); mass spectrum (ESI): 422 (M+H)

Example 48:

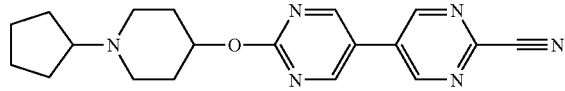

Production of 2-(1-cyclopentylpiperidin-4-yloxy)-5-(2-cyanopyrimidin-4-yl)pyrimidine 1) Production of 2-(1-t-butoxycarbonylpiperidin-4-yloxy)-5-(4,4,5,5-tetramethyl-1,3,2-dioxobororan-2-yl)pyrimidine:
Bis(pinacholato)diboron (160 mg, 0.63 mmol), bis(diphenylphosphino)ferrocene-palladium(II) dichloride, dichloromethane (14 mg, 0.017 mmol), potassium acetate (165 mg, 1.68 mmol) were added to a dimethylsulfoxide (4.0 ml) solution of 2-(1-t-butoxycarbonylpiperidin-4-yloxy)-5-bromopyrimidine (200 mg, 0.56 mmol), and stirred in a nitrogen atmosphere at 80° C. for 1 hour. The reaction mixture was cooled to room temperature, and extracted with ethyl acetate. The organic layer was washed with water and saturated saline solution, dried with anhydrous sodium sulfate and concentrated under reduced pressure. The residue was purified through silica gel column chromatography (C-300, chloroform:methanol=100:3) to obtain the entitled compound (86 mg, 38%).

2) Production of 2-(1-t-butoxycarbonylpiperidin-4-yloxy)-5-(2-cyanopyrimidin-5-yl)pyrimidine:
2-Cyano-5-bromopyrimidine (20 mg, 0.11 mmol), bis(diphenylphosphino)ferrocene-palladium(II) dichloride, dichloromethane (4.0 mg, 0.005 mmol), potassium phosphate (53 mg, 0.25 mmol) were added to a dimethylformamide (2.0 ml) solution of 2-(1-t-butoxycarbonylpiperidin-4-yloxy)-5-(4,4,5,5-tetramethyl-1,3,2-dioxobororan-2-yl)pyrimidine (20 mg, 0.049 mmol), and stirred in a nitrogen atmosphere at 80° C. for 1 hour. The reaction mixture was cooled to room temperature, and extracted with ethyl acetate. The organic layer was washed with water, saturated sodium bicarbonate solution and saturated saline solution in that order, dried with anhydrous sodium sulfate and concentrated under reduced pressure. The residue was purified through partitioning thin-layer column chromatography (ethyl acetate:hexane=1:1) to obtain the entitled compound (9.3 mg, 49%).

3) 2-(1-t-butoxycarbonylpiperidin-4-yloxy)-5-(2-cyanopyrimidin-5-yl)pyrimidine (9.3 mg, 0.024 mmol) was processed in the same manner as in Example 1-3), 4) to obtain the entitled compound (4.5 mg, 53%).

¹HNMR (300 MHz, DMSO-d₆, δ ppm): 1.40-1.80 (6H, m), 1.86-2.08 (4H, m), 2.09-2.22 (2H, m), 2.35-2.52 (2H, m), 2.52-2.65 (1H, m), 2.86-2.98 (2H, m), 5.12-5.21 (1H, m), 8.78 (2H, s), 9.03 (2H, s); mass spectrum (ESI): 351 (M+H)

Example 49:

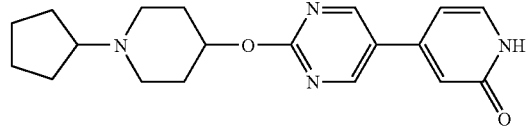

Production of 2-(1-cyclopentylpiperidin-4-yloxy)-5-(1H-pyridin-2-on-4-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1H-pyridin-2-one, the entitled compound was obtained.

¹HNMR (300 MHz, CDCl₃, δ ppm): 1.40-1.70 (6H, m), 1.84-2.01 (4H, m), 2.07-2.15 (2H, m), 2.34-2.41 (2H, m), 2.52-2.58 (1H, m), 2.85-2.89 (2H, m), 5.09-5.13 (1H, m), 6.48 (1H, dd, J=1.8, 6.8 Hz), 6.75 (1H, brs), 7.47 (1H, d, J=6.6 Hz), 8.73 (2H, s); mass spectrum (ESI): 341 (M+H)

Example 50:

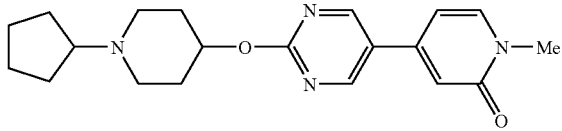

Production of 2-(1-cyclopentylpiperidin-4-yloxy)-5-(1-methyl-1H-pyridin-2-on-4-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-methyl-1H-pyridin-2-one, the entitled compound was obtained.

$^1$HNMR (300 MHz, CDCl$_3$, δ ppm): 1.39-1.72 (6H, m), 1.84-2.00 (4H, m), 2.06-2.14 (2H, m), 2.33-2.40 (2H, m), 2.52-2.57 (1H, m), 2.85-2.88 (2H, m), 3.59 (3H, s), 5.08-5.13 (1H, m), 6.34 (1H, dd, J=1.7, 6.9 Hz), 6.74 (1H, d, J=1.4 Hz), 7.39 (1H, d, J=7.2 Hz), 8.70 (2H, s); mass spectrum (ESI): 355 (M+H)

Example 51:

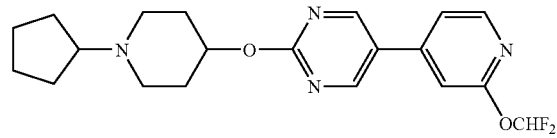

Production of 2-(1-cyclopentylpiperidin-4-yloxy)-5-{2-difluoromethoxypyridin-4-yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-2-(difluoromethoxy)pyridine, the entitled compound was obtained.

$^1$HNMR (300 MHz, CDCl$_3$, δ ppm): 1.36-1.70 (6H, m), 1.83-2.00 (4H, m), 2.08-2.16 (2H, m), 2.34-2.40 (2H, m), 2.51-2.57 (1H, m), 2.86-2.88 (2H, m), 5.10-5.14 (1H, m), 7.04 (1H, d, J=1.5 Hz), 7.24-7.26 (1H, m), 7.51 (1H, t, J=72.8 Hz), 8.27 (1H, d, J=5.3 Hz), 8.74 (2H, s); mass spectrum (ESI): 391 (M+H)

Example 52:

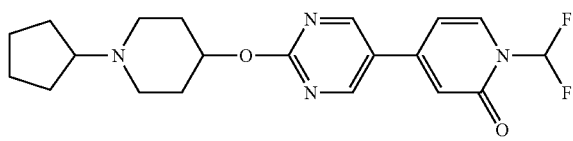

Production of 2-(1-cyclopentylpiperidin-4-yloxy)-5-(1-difluoromethyl-1H-pyridin-2-on-4-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-(difluoromethyl)-1H-pyridin-2-one, the entitled compound was obtained.

$^1$HNMR (300 MHz, CDCl$_3$, δ ppm): 1.41-1.71 (6H, m), 1.85-2.01 (4H, m), 2.02-2.13 (2H, m), 2.35-2.43 (2H, m), 2.54-2.60 (1H, m), 2.86-2.92 (2H, m), 5.11-5.16 (1H, m), 6.51 (1H, d, J=7.4 Hz), 6.73 (1H, s), 7.58 (1H, d, J=7.6 Hz), 7.72 (1H, t, J=61.2 Hz), 8.73 (2H, s); mass spectrum (ESI): 391 (M+H)

Example 53:

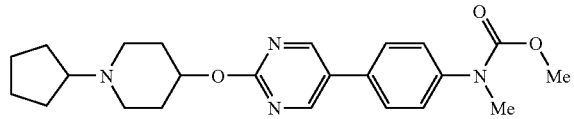

Production of 2-(1-cyclopentylpiperidin-4-yloxy)-5-{4-(N-methyl-N-methoxycarbonylamino)phenyl}pyrimidine 1) Production of 2-(1-(t-butoxycarbonylpiperidin-4-yloxy)-5-{4-(N-methyl-N-methoxycarbonylamino)phenyl}pyrimidine:

5-(4-aminophenyl)-2-(1-t-butoxycarbonylpiperidin-4-yloxy)pyrimidine obtained in Example 32-1) was reacted with methyl chlorocarbonate and then methyl iodide to obtain the entitled compound.

2) 2-(1-(t-butoxycarbonylpiperidin-4-yloxy)-5-{4-(N-methyl-N-methoxycarbonylamino)phenyl}pyrimidine was processed in the same manner as in Example 1-3), 4) to obtain the entitled compound.

$^1$HNMR (300 MHz, CDCl$_3$, δ ppm): 1.37-2.07 (10H, m), 2.07-2.23 (2H, m), 3.32-3.69 (3H, m), 2.84-2.98 (2H, m), 3.34 (3H, s), 3.75 (3H, s), 5.05-5.17 (1H, m), 7.36 (2H, d, J=8.4 Hz), 7.49 (2H, d, J=8.4 Hz), 8.69 (2H, s); mass spectrum (ESI): 411 (M+H)

Example 54:

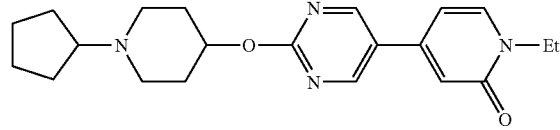

Production of 2-(1-cyclopentylpiperidin-4-yloxy)-5-(1-ethyl-1H-pyridin-2-on-4-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-ethyl-1H-pyridin-2-one, the entitled compound was obtained.

$^1$HNMR (300 MHz, CDCl$_3$, δ ppm): 1.37-1.72 (9H, m), 1.83-2.00 (4H, m), 2.07-2.14 (2H, m), 2.33-2.39 (2H, m), 2.51-2.57 (1H, m), 2.85-2.89 (2H, m), 4.03 (2H, q, J=7.3 Hz), 5.07-5.12 (1H, m), 6.35 (1H, dd, J=1.7, 7.1 Hz), 6.73 (1H, d, J=1.8 Hz), 7.38 (1H, d, J=7.2 Hz), 8.69 (2H, s); mass spectrum (ESI): 369 (M+H)

Example 55:

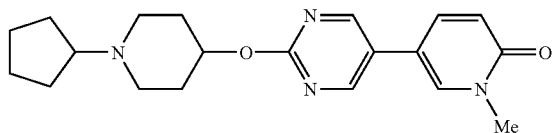

Production of 2-(1-cyclopentylpiperidin-4-yloxy)-5-(1-methyl-1H-pyridin-2-on-5-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 5-bromo-1-methyl-1H-pyridin-2-one, the entitled compound was obtained.

$^1$HNMR (300 MHz, CDCl$_3$, δ ppm): 1.39-1.72 (6H, m), 1.83-1.99 (4H, m), 2.07-2.13 (2H, m), 2.32-2.39 (2H, m), 2.51-2.56 (1H, m), 2.86-2.87 (2H, m), 3.63 (3H, s), 5.04-5.09 (1H, m), 6.70 (1H, d, J=9.5 Hz), 7.44 (1H, d, J=2.3 Hz), 7.50 (1H, dd, J=2.6, 9.3 Hz), 8.53 (2H, s); mass spectrum (ESI): 355 (M+H)

Example 56:

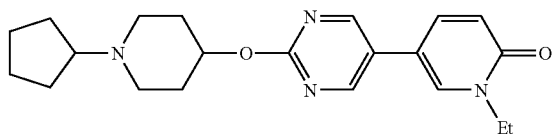

Production of 2-(1-cyclopentylpiperidin-4-yloxy)-5-(1-ethyl-1H-pyridin-2-on-5-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-ethyl-1H-pyridin-2-one, the entitled compound was obtained.

$^1$HNMR (300 MHz, CDCl$_3$, δ ppm): 1.39-1.72 (9H, m), 1.83-1.99 (4H, m), 2.07-2.12 (2H, m), 2.32-2.39 (2H, m), 2.51-2.56 (1H, m), 2.85-2.88 (2H, m), 4.06 (2H, q, J=7.2 Hz), 5.04-5.09 (1H, m), 6.69 (1H, d, J=9.4 Hz), 7.42 (1H, d, J=2.4 Hz), 7.48 (1H, dd, J=2.5, 9.2 Hz), 8.54 (2H, s); mass spectrum (ESI): 369 (M+H)

Example 57:

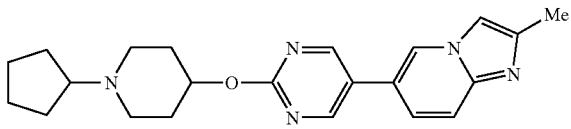

Production of 2-(1-cyclopentylpiperidin-4-yloxy)-5-{2-methylimidazo[1,2,a]pyridin-6-yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 6-bromo-2-methylimidazo[1,2,a]pyridine, the entitled compound was obtained.

$^1$HNMR (300 MHz, CDCl$_3$, δ ppm): 1.35-2.32 (12H, m), 2.32-2.73 (3H, m), 2.49 (3H, s), 2.80-3.04 (2H, m), 5.03-5.23 (1H, m), 7.25 (1H, d, J=9.2 Hz), 7.43 (1H, s), 7.62 (1H, d, J=9.2 Hz), 8.18 (1H, s), 8.68 (2H, s); mass spectrum (ESI): 378 (M+H)

Example 58:

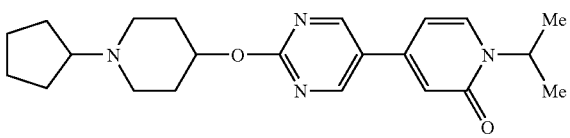

Production of 2-(1-cyclopentylpiperidin-4-yloxy)-5-(2-carbamoylpyridin-5-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-methyl-1H-pyridin-2-one, the entitled compound was obtained.

$^1$HNMR (300 MHz, CDCl$_3$, δ ppm): 1.34-1.73 (12H, m), 1.84-2.00 (4H, m), 2.07-2.14 (2H, m), 2.33-2.41 (2H, m), 2.52-2.58 (1H, m), 2.85-2.88 (2H, m), 5.08-5.13 (1H, m), 5.25-5.32 (1H, m), 6.40 (1H, dd, J=2.1, 7.3 Hz), 6.73 (1H, d, J=2.2 Hz), 7.43 (1H, d, J=7.3 Hz), 8.70 (2H, s); mass spectrum (ESI): 383 (M+H)

Example 59:

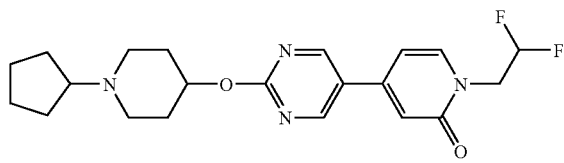

Production of 2-(1-cyclopentylpiperidin-4-yloxy)-5-{1-(2,2-difluoroethyl)-1H-pyridin-2-on-4yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-(2,2-difluoroethyl)-1H-pyridin-2-one, the entitled compound was obtained.

$^1$HNMR (300 MHz, CDCl$_3$, δ ppm): 1.36-1.69 (6H, m), 1.83-2.00 (4H, m), 2.06-2.13 (2H, m), 2.33-2.40 (2H, m), 2.51-2.60 (1H, m), 2.87-2.88 (2H, m), 4.28 (2H, dt, J=4.4, 13.4 Hz), 5.07-5.14 (1H, m), 6.15 (1H, tt, J=4.4, 56.0 Hz), 6.40 (1H, dd, J=1.9, 7.2 Hz), 6.75 (1H, d, J=1.9 Hz) 7.37 (1H, d, J=7.2 Hz), 8.71 (2H, s); mass spectrum (ESI): 374 (M+H)

Example 60:

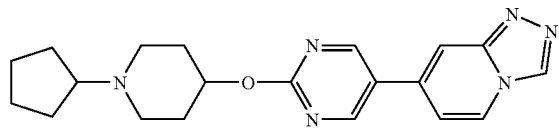

Production of 2-(1-cyclopentylpiperidin-4-yloxy)-5-(1,2,4-triazolo[4,3,a]pyridin-7-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 7-bromo-1,2,4-triazolo[4,3,a]pyridine, the entitled compound was obtained.

$^1$HNMR (300 MHz, CDCl$_3$, δ ppm): 1.32-2.20 (12H, m), 2.30-2.65 (3H, m), 2.82-2.98 (2H, m), 5.05-5.20 (1H, m), 7.07 (1H, d, J=6.9 Hz), 7.94 (1H, s), 8.24 (1H, d, J=6.9 Hz), 8.80 (2H, s), 8.87 (1H, s); mass spectrum (ESI): 365 (M+H)

Example 61:

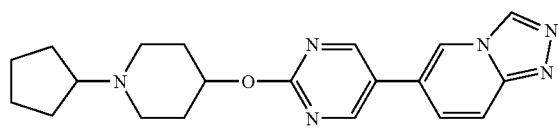

Production of 2-(1-cyclopentylpiperidin-4-yloxy)-5-(1 2,4-triazolo[4,3,a]pyridin-6-yl)pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 6-bromo-1,2,4-triazolo[4,3,a]pyridine, the entitled compound was obtained.

$^1$HNMR (300 MHz, CDCl$_3$, δ ppm): 1.32-2.20 (12H, m), 2.30-2.65 (3H, m), 2.82-2.98 (2H, m), 5.05-5.20 (1H, m), 7.44 (1H, d, J=9.5 Hz), 7.92 (1H, d, J=9.5 Hz), 8.32 (1H, s), 8.72 (2H, s), 8.94 (1H, s); mass spectrum (ESI): 365 (M+H)

Example 62:

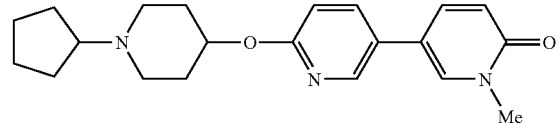

Production of 2-(1-cyclopentylpiperidin-4-yloxy)-5-(1-methyl-1H-pyridin-2-on-5-yl)pyridine 1) Production of 2-(1-t-butoxycarbonylpiperidin-4-yloxy)-5-(4,4,5,5-tetramethyl-1,3,2-dioxobororan-2-yl)pyridine:

According to the same method as in Example 48-1) but using 5-bromo-2-(1-t-butoxycarbonylpiperidin-4-yloxy)pyridine and bis(pinacholato)diboron, the entitled compound was obtained.

2) According to the same method as in Example 48-2), 3) but using the intermediate obtained in 1) and 4-bromo-1-methyl-1H-pyridin-2-one, the entitled compound was obtained.

$^1$HNMR (300 MHz, CDCl$_3$, δ ppm): 1.39-1.72 (6H, m), 1.81-1.89 (4H, m), 2.05-2.10 (2H, m), 2.31-2.37 (2H, m), 2.50-2.55 (1H, m), 2.82-2.87 (2H, m), 3.62 (3H, s), 5.06-5.08 (1H, m), 6.67 (1H, d, J=9.5 Hz), 6.76 (1H, d, J=8.6 Hz), 7.40 (1H, d, J=2.4 Hz), 7.52 (1H, dd, J=2.6, 9.5 Hz), 7.58 (1H, dd, J=2.6, 8.6 Hz), 8.16 (1H, d, J=2.5 Hz); mass spectrum (ESI): 354 (M+H)

Example 63:

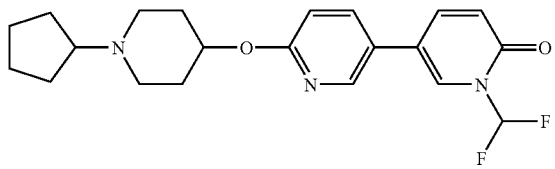

Production of 2-(1-cyclopentylpiperidin-4-yloxy)-5-(1-difluoromethyl-1H-pyridin-2-on-5-yl)pyridine According to the same method as in Example 48-2), 3) but using the intermediate obtained in Example 62-1) and 5-bromo-1-(difluoromethyl)-1H-pyridin-2-one, the entitled compound was obtained.

$^1$HNMR (300 MHz, CDCl$_3$, δ ppm): 1.40-1.69 (6H, m), 1.81-1.89 (4H, m), 2.06-2.10 (2H, m), 2.31-2.37 (2H, m), 2.50-2.56 (1H, m), 2.84-2.86 (2H, m), 5.07-5.11 (1H, m), 6.66 (1H, d, J=9.6 Hz), 6.78 (1H, d, J=8.6 Hz), 7.54-7.63 (3H, m), 7.74 (1H, d, J=60.1 Hz), 8.20 (1, d, J=2.6 Hz); mass spectrum (ESI): 390 (M+H)

Example 64:

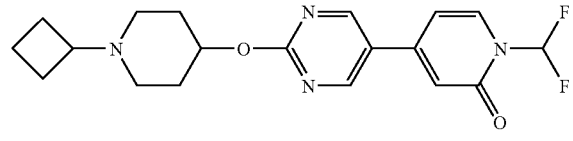

Production of 2-(1-cyclobutylpiperidin-4-yloxy)-5-{1-difluoromethyl-1H-pyridin-2-on-4-yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-(difluoromethyl)-1H-pyridin-2-one, the entitled compound was obtained.

$^1$HNMR (300 MHz, CDCl$_3$, δ ppm): 1.62-1.75 (2H, m), 1.88-2.20 (10H, m), 2.67-2.79 (3H, m), 5.12-5.15 (1H, m), 6.51 (1H, d, J=7.6 Hz), 6.73 (1H, s), 7.58 (1H, d, J=7.6 Hz), 7.72 (1H, t, J=60.3 Hz), 8.73 (2H, s); mass spectrum (ESI): 377 (M+H)

Example 65:

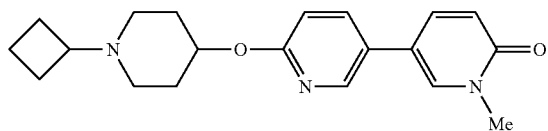

Production of 2-(1-cyclobutylpiperidin-4-yloxy)-5-{1-methyl-1H-pyridin-2-on-5-yl}pyridine According to the same method as in Example 48-2), 3) but using the intermediate obtained in Example 62-1) and 5-bromo-1-methyl-1H-pyridin-2-one, the entitled compound was obtained.

$^1$HNMR (300 MHz, CDCl$_3$, δ ppm): 1.64-1.93 (6H, m), 2.01-2.15 (6H, m), 2.65-2.74 (3H, m), 3.61 (3H, s), 5.06-5.09 (1H, m), 6.67 (1H, d, J=9.5 Hz), 6.76 (1H, d, J=8.6 Hz), 7.40 (1H, d, J=2.6 Hz), 7.52 (1H, dd, J=2.6, 9.5 Hz), 7.57 (1H, dd, J=2.6, 8.6 Hz), 8.16 (1H, d, J=2.6 Hz); mass spectrum (ESI): 340 (M+H)

Example 66:

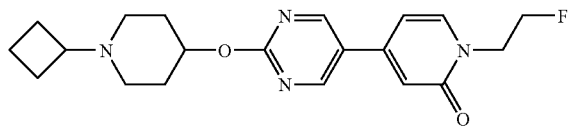

Production of 2-(1-cyclobutylpiperidin-4-yloxy)-5-{1-(2-fluoroethyl)-1H-pyridin-2-on-4-yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-(2-fluoroethyl)-1H-pyridin-2-one, the entitled compound was obtained.

$^1$HNMR (300 MHz, CDCl$_3$, δ ppm): 1.62-1.75 (2H, m), 1.88-2.20 (10H, m), 2.67-2.79 (3H, m), 5.12-5.15 (1H, m), 6.51 (1H, d, J=7.6 Hz), 6.73 (1H, s), 7.58 (1H, d, J=7.6 Hz), 7.72 (1H, t, J=60.3 Hz), 8.73 (2H, s); mass spectrum (ESI): 377 (M+H)

Example 67:

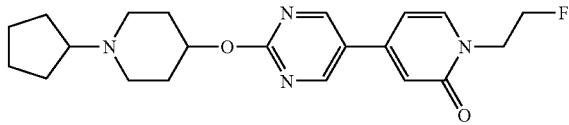

Production of 2-(1-cyclopentylpiperidin-4-yloxy)-5-1-(2-fluoroethyl)-1H-pyridin-2-on-4-yl}pyrimidine According to the same method as in Example 48-2), 3) but using 2-(1-t-butoxycarbonylpiperidin-4-yloxy)-5-(4,4,5,5-tetramethyl-1,3,2-dioxobororan-2-yl)pyrimidine obtained in Example 48-1) and 4-bromo-1-(2-fluoroethyl)-1H-pyridin-2-one, the entitled compound was obtained.

$^1$HNMR (300 MHz, CDCl$_3$, δ ppm): 1.38-1.76 (6H, m), 1.84-1.99 (4H, m), 2.07-2.13 (2H, m), 2.32-2.39 (2H, m), 2.50-2.56 (1H, m), 2.86-2.89 (2H, m), 4.28 (2H, dt, J=4.5, 27.7 Hz), 4.75 (2H, dt, J=4.5, 47.4 Hz), 5.08-5.11 (1H, m), 6.37 (1H, dd, J=2.0, 7.1 Hz), 6.74 (1H, d, J=1.8 Hz), 7.43 (1H, d, J=7.0 Hz), 8.70 (2H, s); mass spectrum (ESI): 387 (M+H)

Example 68:

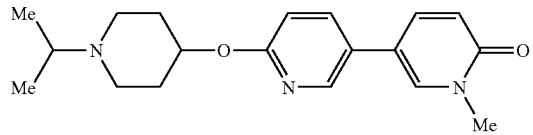

Production of 2-(1-isopropylpiperidin-4-yloxy)-5-{1-methyl-1H-pyridin-2-on-5-yl}pyridine According to the same method as in Example 48-2), 3) but using the intermediate obtained in Example 62-1) and 5-bromo-1-methyl-1H-pyridin-2-one, the entitled compound was obtained.

$^1$HNMR (300 MHz, CDCl$_3$, δ ppm): 1.09 (6H, d, J=6.6 Hz), 1.81-1.88 (2H, m), 2.10-2.18 (2H, m), 2.44-2.50 (2H, m), 2.78-2.87 (3H, m), 3.61 (3H, s), 5.05-5.08 (1H, m), 6.66 (1H, d, J=9.2 Hz), 6.76 (1H, dd, J=0.7, 8.7 Hz), 7.41 (1H, d, J=2.3 Hz), 7.52 (1H, dd, J=2.7, 9.4 Hz), 7.58 (1H, dd, J=2.6, 8.6 Hz), 8.16 (1H, d, J=2.7 Hz); mass spectrum (ESI): 328 (M+H)

Example 69:

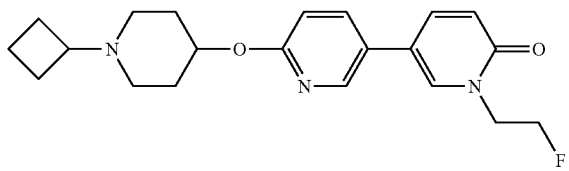

Production of 2-(1-cyclobutylpiperidin-4-yloxy)-5-{1-(2-fluoroethyl)-1H-pyridin-2-on-5-yl}pyridine According to the same method as in Example 48-2), 3) but using the intermediate obtained in Example 62-1) and 5-bromo-1-(2-fluoromethyl)-1H-pyridin-2-one, the entitled compound was obtained.

$^1$HNMR (300 MHz, CDCl$_3$, δ ppm): 1.55-1.93 (6H, m), 2.00-2.20 (6H, m), 2.55-2.77 (3H, m), 4.30 (2H, dt, J=4.4, 27.8 Hz), 4.76 (2H, dt, J=4.4, 47.3 Hz), 5.06-5.09 (1H, m), 6.69 (1H, d, J=9.6 Hz), 6.76 (1H, dd, J=0.7, 8.6 Hz), 7.44 (1H, d, J=2.6 Hz), 7.54-7.61 (2H, m), 8.17 (1H, d, J=1.9 Hz); mass spectrum (ESI): 372 (M+H)

Example 70:

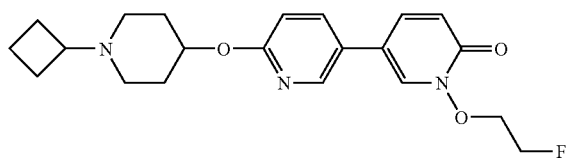

Production of 2-(1-cyclobutylpiperidin-4-yloxy)-5-{1-(2-fluoroethoxy-1H-pyridin-2-on-5-yl}pyridine According to the same method as in Example 48-2), 3) but using the intermediate obtained in Example 62-1) and 5-bromo-1-(2-fluoroethoxy)-1H-pyridin-2-one, the entitled compound was obtained.

$^1$HNMR (300 MHz, CDCl$_3$, δ ppm): 1.64-1.92 (6H, m), 2.00-2.15 (6H, m), 2.65-2.74 (3H, m), 4.56-4.81 (4H, m), 5.06-5.09 (1H, m), 6.75-6.78 (2H, m), 7.53 (1H, dd, J=2.6, 9.5 Hz), 7.59 (1H, dd, J=2.6, 8.6 Hz), 7.71 (1H, d, J=2.3 Hz), 8.17 (1H, d, J=2.3 Hz); mass spectrum (ESI): 388 (M+H)

Example 71:

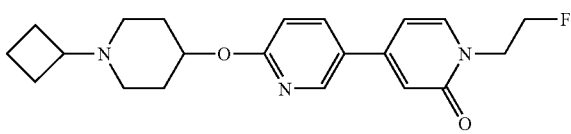

Production of 2-(1-cyclobutylpiperidin-4-yloxy)-5-{1-(2-fluoroethyl-1H-pyridin-2-on-4-yl}pyridine According to the same method as in Example 48-2), 3) but using the intermediate obtained in Example 62-1) and 4-bromo-1-(2-fluoroethoxy)-1H-pyridin-2-one, the entitled compound was obtained.

$^1$HNMR (300 MHz, CDCl$_3$, δ ppm): 1.59-1.93 (6H, m), 2.00-2.19 (6H, m), 2.64-2.77 (3H, m), 4.27 (2H, dt, J=4.5, 27.7 Hz), 4.75 (2H, dt, J=4.5, 47.3 Hz), 5.10-5.13 (1H, m), 6.39 (1H, dd, J=2.0, 7.1 Hz), 6.74 (1H, d, J=2.0 Hz), 6.79 (1H, dd, J=0.7, 8.6 Hz), 7.37 (1H, d, J=7.0 Hz), 7.75 (1H, dd, J=2.6, 8.6 Hz), 8.37 (1H, d, J=2.6 Hz); mass spectrum (ESI): 372 (M+H)

Example 72:

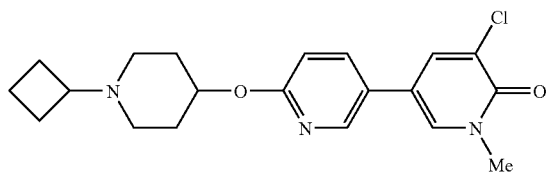

Production of 2-(1-cyclobutylpiperidin-4-yloxy)-5-{3-chloro-1-methyl-1H-pyridin-2-on-5-yl}pyridine According to the same method as in Example 48-2), 3) but using the intermediate obtained in Example 62-1) and 3-chloro-5-iodo-1-methyl-1H-pyridin-2-one, the entitled compound was obtained.

$^1$HNMR (300 MHz, CDCl$_3$, δ ppm): 1.62-1.92 (6H, m), 2.01-2.15 (6H, m), 2.65-2.74 (3H, m), 3.68 (3H, s), 5.06-5.09 (1H, m), 6.76 (1H, d, J=8.6 Hz), 7.36 (1H, d, J=2.4 Hz), 7.56 (1H, dd, J=2.6, 8.6 Hz), 7.72 (1H, d, J=2.4 Hz), 8.14 (1H, d, J=2.3 Hz); mass spectrum (ESI): 374 (M+H)

Example 73:

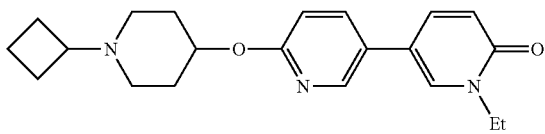

Production of 2-(1-cyclobutylpiperidin-4-yloxy)-5-{1-ethyl-1H-pyridin-2-on-5-yl}pyridine According to the same method as in Example 48-2), 3) but using the intermediate obtained in Example 62-1) and 5-bromo-1-ethyl-1H-pyridin-2-one, the entitled compound was obtained.

$^1$HNMR (300 MHz, CDCl$_3$, δ ppm): 1.49 (3H, t, J=7.2 Hz), 1.73-2.02 (6H, m), 2.09-2.28 (6H, m), 2.73-2.86 (3H, m), 4.14 (2H, q, J=7.2 Hz), 5.15-5.18 (1H, m), 6.75 (1H, d, J=9.2 Hz), 6.85 (1H, d, J=8.6 Hz), 7.48 (1H, d, J=2.6 Hz), 7.60 (1H, dd, J=2.6, 9.3 Hz), 7.67 (1H, dd, J=2.6, 8.6 Hz), 8.25 (1H, d, J=2.6 Hz); mass spectrum (ESI): 354 (M+H)

Example 74:

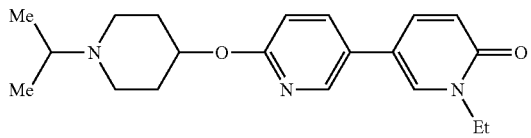

Production of 2-(1-isopropylpiperidin-4-yloxy)-5-{1-ethyl-1H-pyridin-2-on-5-yl}pyridin According to the same method as in Example 48-2), 3) but using the intermediate obtained in Example 62-1) and 5-bromo-1-ethyl-1H-pyridin-2-one, the entitled compound was obtained.

$^1$HNMR (300 MHz, CDCl$_3$, δ ppm): 1.07 (6H, d, J=6.6 Hz), 1.40 (3H, t, J=7.2 Hz), 1.79-1.88 (2H, m), 2.06-2.11 (2H, m), 2.41-2.48 (2H, m), 2.75-2.85 (3H, m), 4.05 (2H, q, J=7.2 Hz), 5.04-5.07 (1H, m), 6.65 (1H, d, J=9.4 Hz), 6.76 (1H, dd, J=0.7, 8.6 Hz), 7.39 (1H, d, J=2.6 Hz), 7.50 (1H, dd, J=2.6, 9.5 Hz), 7.58 (1H, dd, J=2.6, 8.6 Hz), 8.16 (1H, dd, J=0.7, 2.6 Hz); mass spectrum (ESI): 342 (M+H)

INDUSTRIAL APPLICABILITY

The heteroaryloxy-nitrogen-containing saturated heterocyclic derivatives of formula (I) and their pharmaceutically-acceptable salts of the invention have a strong histamine-H3 receptor agonistic or inverse-agonistic activity, and are useful for remedy and/or prevention of metabolic system diseases such as obesity, diabetes, hormone secretion disorder, hyperlipemia, gout, fatty liver; circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder; and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

The invention claimed is:
1. A compound of the formula (I):

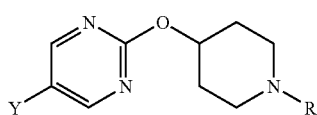
(I)

wherein:
R is selected from the group consisting of:
a linear or branched C$_{2-6}$alkyl group, and a cycloalkyl group having from 3 to 9 carbon atoms,
which is unsubstituted or substituted with a group selected from the group consisting of: a cyano group; a hydroxyl group; a lower alkyl group optionally substituted with a hydroxyl group, a halogen atom or an amino group; a lower alkoxy group optionally substituted with a halogen atom; a mono-lower alkylaminocarbonyloxy group; a di-lower alkylaminocarbonyloxy group; a mono-lower alkylcarbamoyl group; a di-lower alkylcarbamoyl group; a carbamoyl group; a cycloalkyliminocarbonyl group; and a trifluoromethyl group,
Y is selected from the group consisting of:
(1) a phenyl group, a pyridyl group and a pyrimidinyl group;
which may have 1 or 2 substituents selected from the group consisting of: a hydroxyl group; a lower alkyl group optionally substituted with a hydroxy group, a halogen atom or an amino group; a lower alkoxy group optionally substituted with a halogen atom; a lower alkylsulfonyl group; a cyclo-lower alkylsulfonyl group; a halogen atom; a mono-lower alkylaminocarbonyloxy group; a di-lower alkylaminocarbonyloxy group; a mono-lower alkylcarbamoyl group; a di-lower alkylcarbamoyl group; a cycloalkyliminocarbamoyl group; a lactam ring; a mono-lower alkylamino group; a di-lower alkylamino group; an alkanoyl group; an alkoxycarbonylamino group wherein the nitrogen atom optionally substituted with a lower alkyl group; an alkanoylamino group wherein the nitrogen atom is optionally substituted with a lower alkyl group; and an alkylsulfonylamino group wherein the nitrogen atom is optionally substituted with a lower alkyl group;
(2) a bi-cyclic condensed ring selected from a group consisting of:
naphthyl, quinolinyl, indolyl, [1,2,4]-triazolo[4,3-a]pyridine and dibenzo[b,d]furan;
which may have 1 or 2 substituents selected from the group consisting of: a hydroxyl group; a lower alkyl group optionally substituted with a hydroxy group, a halogen atom or an amino group; a lower alkoxy group optionally substituted with a halogen atom; a lower alkylsulfonyl group; a cyclo-lower alkylsulfonyl group; a halogen atom; a mono-lower alkylaminocarbonyloxy group; a di-lower alkylaminocarbonyloxy group; a mono-lower alkylcarbamoyl group; a di-lower alkylcarbamoyl group; a cycloalkyliminocarbamoyl group; a lactam ring; a mono-lower alkylamino group; a di-lower alkylamino group; an alkanoyl group; an alkoxycarbonylamino group wherein the nitrogen atom is optionally substituted with a lower alkyl group; an alkanoylamino group wherein the nitrogen atom is optionally substituted with a lower alkyl group; and an alkylsulfonylamino group wherein the nitrogen atom is optionally substituted with a lower alkyl group;
(3) a thienyl group;
which may have 1 or 2 substituents selected from the group consisting of: a hydroxyl group; a lower alkyl group optionally substituted with a hydroxy group, a halogen atom or an amino group; a lower alkoxy group optionally substituted with a halogen atom; a lower alkylsulfonyl group; a cyclo-lower alkylsulfonyl group; a halogen atom; a mono-lower alkylaminocarbonyloxy group; a di-lower alkylaminocarbonyloxy group; a mono-lower alkylcarbamoyl group; a di-lower alkylcarbamoyl group; a cycloalkyliminocarbamoyl group; a lactam ring; a mono-lower alkylamino group; a di-lower alkylamino group; an alkanoyl group; an alkoxycarbonylamino group wherein the nitrogen atom is optionally substituted with a lower alkyl group; an alkanoylamino group wherein the nitrogen atom is optionally substituted with a lower alkyl group; and an alkylsulfonylamino group wherein the nitrogen atom is optionally substituted with a lower alkyl group;
(4) a piperidinyl group;
which may have 1 or 2 substituents selected from the group consisting of: a hydroxyl group; a lower alkyl group optionally substituted with a hydroxy group, a halogen atom or an amino group; a lower alkoxy group optionally substituted with a halogen atom; a halogen atom; a mono-lower alkylaminocarbonyloxy group; a di-lower alkylaminocarbonyloxy group; a mono-lower alkylcarbamoyl group; a di-lower alkylcarbamoyl group; a cycloalkyliminocarbamoyl group; a lactam ring; a mono-lower alkylamino group; a di-lower alkylamino group; an alkanoyl group; an alkoxycarbonylamino group wherein the nitrogen atom is optionally substituted with a lower alkyl group; an alkanoylamino group wherein the nitrogen atom is optionally substituted with a lower alkyl group; and an alkylsulfonylamino group wherein the nitrogen atom is optionally substituted with a lower alkyl group;
(5) a group of the formula (IV-2):

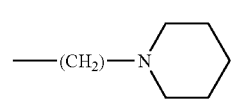
(IV-2)

and (6) a group of the formula (Q1-1):

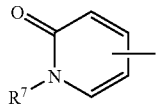

(Q1-1)

wherein $R^7$ represents a hydrogen atom, a lower alkyl group, a cyclo-lower alkyl group, a halo-lower alkyl group, or an aralkyl group;
or a pharmaceutically acceptable salt thereof.

2. The compound of claim 1, wherein R in formula (II) is a cycloalkyl group having from 3 to 9 carbon atoms;
which is unsubstituted or substituted with a group selected from the group consisting of: a cyano group; a hydroxy group; a lower alkyl group optionally substituted with a hydroxy group, a halogen atom or an amino group; a lower alkoxy group; a mono-lowere alkylaminocarbonyloxy group; and a di-lower alkylaminocarbonyloxy group.

3. The compound of claim 1 wherein R is selected from the group consisting of:
cyclopropyl, cyclobutyl, cyclopentyl and cyclohexyl.

4. The compound of claim 1 wherein Y is a group of the formula (Q1-1):

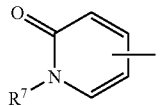

(Q1-1)

wherein $R^7$ represents a hydrogen atom, a lower alkyl group, a cyclo-lower alkyl group, a halo-lower alkyl group, or an aralkyl group.

5. The compound of claim 1 wherein Y is selected from the group consisting of:
1H-pyridin-2-on-5-yl,
1H-pyridin-2-on-1-yl,
1-cyclopentyl-1H-pyridin-2-on-3-yl,
1H-pyridin-2-on-4-yl,
1-methyl-1H-pyridin-2-on-4-yl,
1-difluoromethyl-1H-pyridin-2-on-4-yl,
1-ethyl-1H-pyridin-2-on-4-yl,
1-methyl-1H-pyridin-2-on-5-yl,
1-(2,2-difluoroethyl)-1H-pyridin-2-on-4-yl, and
1-(2-fluoroethyl)-1H-pyridin-2-on-4-yl.

6. A compound which is selected from the group consisting of:
2-(1-cyclopentylpiperidin-4-yloxy)-5-(4-cyanophenyl) pyrimidine,
2-(1-isopropylpiperidin-4-yloxy)-5-(4-cyanophenyl)pyrimidine,
2-(1-cyclopentylpiperidin-4-yloxy)-5-{(3-methyl-1,2,4-oxadiazol-5-yl)phenyl}pyrimidine,
2-(1-cyclopentylpiperidin-4-yloxy)-5-(4-cyanophenyl) pyrimidine,
2-(1-(cyclobutylpiperidin-4-yloxy)-5-(4-cyanophenyl)pyrimidine,
2-(1-cyclohexylpiperidin-4-yloxy)-5-(4-cyanophenyl)pyrimidine,
2-(1-cyclopropylpiperidin-4-yloxy)-5-(4-cyanophenyl) pyrimidine,
2-(1-ethylpiperidin-4-yloxy)-5-(4-cyanophenyl)pyrimidine,
2-(1-cyclopentylpiperidin-4-yloxy)-5-{4-(pyrrolidin-1-ylcarbonyl)phenyl}pyrimidine,
2-(1-cyclopentylpiperidin-4-yloxy)-5-{4-(dimethylcarbamoyl)phenyl}pyrimidine,
2-(1-cyclopentylpiperidin-4-yloxy)-5-{4-(morpholin-4-ylcarbonyl)phenyl}pyrimidine,
2-(1-cyclopentylpiperidin-4-yloxy)-5-{4-(phenoxy) phenyl}pyrimidine,
2-(1-cyclopentylpiperidin-4-yloxy)-5-(3-quinolinyl)pyrimidine,
2-(1-cyclopentylpiperidin-4-yloxy)-5-(5-indolyl)pyrimidine,
2-(1-cyclopentylpiperidin-4-yloxy)-5-(1H-pyridin-2-on-1-yl)pyrimidine,
2-(1-cyclopentylpiperidin-4-yloxy)-5-(piperidin-2-on-1-yl)pyrimidine,
2-(1-cyclopentylpiperidin-4-yloxy)-5-(8-quinolinyl)pyrimidine,
2-(1-cyclopentylpiperidin-4-yloxy)-5-(4-phenyl-4-hydroxypiperidin-1-yl)pyrimidine,
2-(1-cyclopentylpiperidin-4-yloxy)-5-(2-methoxypyridin-5-yl)pyrimidine,
2-(1-cyclopentylpiperidin-4-yloxy)-5-(4-chlorophenyl) pyrimidine,
2-(1-cyclopentylpiperidin-4-yloxy)-5-(4-trifluoromethylphenyl)pyrimidine,
2-(1-cyclopentylpiperidin-4-yloxy)-5-(pyridin-3-yl)pyrimidine,
2-(1-cyclopentylpiperidin-4-yloxy)-5-(4-methoxyphenyl) pyrimidine,
2-(1-cyclopentylpiperidin-4-yloxy)-5-(dibenzofuran-4-yl)pyrimidine,
2-(1-cyclopentylpiperidin-4-yloxy)-5-(2-cyclopentyloxypyridin-5-yl)pyrimidine,
2-(1-cyclopentylpiperidin-4-yloxy)-5-(1H-pyridin-2-on-5-yl)pyrimidine,
2-(1-cyclopentylpiperidin-4-yloxy)-5-(1-cyclopentyl-1H-pyridin-2-on-3-yl)pyrimidine,
2-(1-cyclopentylpiperidin-4-yloxy)-5-{2-(pyrrolidin-1-ylcarbonyl)pyridin-5- yl}pyrimidine,
2-(1-cyclopentylpiperidin-4-yloxy)-5-(2-cyano-5-thienyl) pyrimidine,
2-(1-cyclopentylpiperidin-4-yloxy)-5-{4-(morpholin-3-on-4-yl)phenyl}pyrimidine,
2-(1-cyclopentylpiperidin-4-yloxy)-5-{4-(2-oxazolidin-3-yl)phenyl}pyrimidine,
2-(1-cyclopentylpiperidin-4-yloxy)-5-(2-methylpyridin-5-yl)pyrimidine,
2-(1-cyclopentylpiperidin-4-yloxy)-5-(2-fluoropyridin-5-yl)pyrimidine,
2-(1-cyclopentylpiperidin-4-yloxy)-5-{4-(1H-pyridin-2-on-1-yl)phenyl}pyrimidine,
2-(1-cyclopentylpiperidin-4-yloxy)-5-{4-(methylsulfonyl)phenyl}pyrimidine,
2-(1-cyclopentylpiperidin-4-yloxy)-5-{4-acetylphenyl}pyrimidine,
2-(1-cyclopentylpiperidin-4-yloxy)-5-(4-trifluoromethoxyphenyl)pyrimidine,
2-(1-cyclopentylpiperidin-4-yloxy)-5-{4-(2-hydroxy-2-propyl)phenyl}pyrimidine,
2-(1-cyclopentylpiperidin-4-yloxy)-5-(2-ethylpyridin-5-yl)pyrimidine, 2-(1-cyclopentylpiperidin-4-yloxy)-5-(piperidin-1-ylcarbonyl)pyrimidine,
2-(1-cyclopentylpiperidin-4-yloxy)-5-(piperidin-1-ylmethyl)phenyl}pyrimidine,
2-(1-cyclopentylpiperidin-4-yloxy)-5-(4-phenylpiperazin-1-ylmethyl)pyrimidine,
2-(1-cyclopentylpiperidin-4-yloxy)-5-(2-cyanopyrimidin-5-yl)pyrimidine,
2-(1-cyclopentylpiperidin-4-yloxy)-5-(1H-pyridin-2-on-4-yl)pyrimidine,
2-(1-cyclopentylpiperidin-4-yloxy)-5-(1-methyl-1H-pyridin-2-on-4-yl)pyrimidine,
2-(1-cyclopentylpiperidin-4-yloxy)-5-(2-difluoromethoxypyridin-4-yl)pyrimidine,
2-(1-cyclopentylpiperidin-4-yloxy)-5-(1-difluoromethyl-1H-pyridin-2-on-4-yl)pyrimidine,
2-(1-cyclopentylpiperidin-4-yloxy)-5-{4-(N-methyl-N-methoxycarbonylamino)phenyl}-pyrimidine,
2-(1-cyclopentylpiperidin-4-yloxy)-5-(1-ethyl-1H-pyridin-2-on-4-yl)pyrimidine,
2-(1-cyclopentylpiperidin-4-yloxy)-5-(1-methyl-1H-pyridin-2-on-5-yl)pyrimidine,
2-(1-cyclopentylpiperidin-4-yloxy)-5-(1-ethyl-1H-pyridin-2-on-5-yl)pyrimidine,
2-(1-cyclopentylpiperidin-4-yloxy)-5-(2-methylimidazo[1,2,a]pyridin-6-yl)pyrimidine,
2-(1-cyclopentylpiperidin-4-yloxy)-5-(2-carbamoylpyridin-5-yl)pyrimidine,
2-(1-cyclopentylpiperidin-4-yloxy)-5-{1-(2,2-difluoroethyl)-1H-pyridin-2-on-4-yl}pyrimidine,
2-(1-cyclopentylpiperidin-4-yloxy)-5-(1,2,4-triazolo[4,3,a]pyridin-7-yl)pyrimidine,
2-(1-cyclopentylpiperidin-4-yloxy)-5-(1,2,4-triazolo[4,3,a]pyridin-6-yl)pyrimidine,
2-(1-cyclobutylpiperidin-4-yloxy)-5-(1-difluoromethyl-1H-pyridin-2-on-4-yl)pyrimidine,
2-(1-cyclobutylpiperidin-4-yloxy)-5-{1-(2-fluoroethyl)-1H-pyridin-2-on-4-yl}pyrimidine,
2-(1-cyclopentylpiperidin-4-yloxy)-5-{1-(2-fluoroethyl)-1H-pyridin-2-on-4-yl}pyrimidine,
or a pharmaceutically acceptable salt thereof.

7. A pharmaceutical composition which comprises an inert carrier and the compound of claim 1, or a pharmaceutically acceptable salt thereof.

8. A pharmaceutical composition which comprises an inert carrier and the compound of claim 6, or a pharmaceutically acceptable salt thereof.

* * * * *

UNITED STATES PATENT AND TRADEMARK OFFICE
CERTIFICATE OF CORRECTION

PATENT NO. : 7,595,316 B2  Page 1 of 1
APPLICATION NO. : 10/561115
DATED : September 29, 2009
INVENTOR(S) : Ohtake et al.

It is certified that error appears in the above-identified patent and that said Letters Patent is hereby corrected as shown below:

On the Title Pg

Item [*] Notice:   Subject to any disclaimer, the term of this patent is extended or adjusted under 35 USC 154(b) by 271 days Delete the phrase "by 271 days" and insert -- by 346 days --

Signed and Sealed this

Twenty-fifth Day of May, 2010

David J. Kappos
*Director of the United States Patent and Trademark Office*